United States Patent
Saris et al.

(10) Patent No.: US 7,348,162 B2
(45) Date of Patent: Mar. 25, 2008

(54) NUCLEIC ACIDS ENCODING FIBROBLAST GROWTH FACTOR RECEPTOR-LIKE PROTEINS AND USES THEREOF

(75) Inventors: Christiaan M. Saris, Newbury Park, CA (US); Sharon X. Mu, Thousand Oaks, CA (US); Min Xia, Newbury Park, CA (US); Thomas Charles Boone, Newbury Park, CA (US); Todd Covey, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 199 days.

(21) Appl. No.: 09/815,108

(22) Filed: Mar. 22, 2001

(65) Prior Publication Data
US 2002/0009776 A1  Jan. 24, 2002

Related U.S. Application Data

(60) Provisional application No. 60/191,379, filed on Mar. 22, 2000.

(51) Int. Cl.
  *C12P 21/06* (2006.01)
  *C12N 5/00* (2006.01)
  *C07H 21/02* (2006.01)

(52) U.S. Cl. ............... 435/69.1; 435/70.1; 435/325; 536/23.1

(58) Field of Classification Search ........... 435/69.1, 435/70.1, 320.1, 325, 243; 536/23.1, 23.51, 536/24.31
See application file for complete search history.

(56) References Cited

U.S. PATENT DOCUMENTS 6,242,419 B1 *  6/2001  Strachan et al. ............ 514/12

FOREIGN PATENT DOCUMENTS

| WO | WO 99/63088 A | 12/1999 |
| WO | WO 00/24756 A | 5/2000 |
| WO | WO 00/58463 A | 10/2000 |

OTHER PUBLICATIONS

Ngo et al., 1994, Computational Complexity, Protein Structure prediction, and the Levinthal Paradox, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Wiedemann et al., "Characterization of a Novel Protein (FGFR1) from Human Carilage Related to FGF Receptors." *Genomics*, 2000, 69:275-279.
Wiedemann et al., "The Mouse Fgfr;1 Gene Coding for a Novel FGF Receptor-Like Protein," *Biochemica et Biophysica Acta*, 2001, 1520:247-250.
Sleeman et al., "Identification of a New Fibroblast Growth Factor Receptor, FGFR5," *Gene*, 2001, 271:171-182.
GENEBANK Acc. No. AI 245701.
Kim et al., A Novel Fibroblast Growth Factor Receptor-5 Preferentially Expressed in the Pancreas., Biochim. Biophys. Acta, 2001 1518:152-156.

* cited by examiner

*Primary Examiner*—Christine J. Saoud
*Assistant Examiner*—Jegatheesan Seharaseyon
(74) *Attorney, Agent, or Firm*—McDonnell Boehnen Hulbert & Berghoff LLP

(57) ABSTRACT

The present invention provides Fibroblast Growth Factor Receptor-Like (FGFR-L) polypeptides and nucleic acid molecules encoding the same. The invention also provides selective binding agents, vectors, host cells, and methods for producing FGFR-L polypeptides. The invention further provides pharmaceutical compositions and methods for the diagnosis, treatment, amelioration, and/or prevention of diseases, disorders, and conditions associated with FGFR-L polypeptides.

11 Claims, 30 Drawing Sheets

FIG. 1A

```
gacctgggtc ttgcgggcct gagccctgag tggcgtccag tccagctccc agtgaccgcg    60 ccctgcttc aggtccgacc ggcgag atg acg cgg agc ccc gcg ctg ctg ctg    113
                            Met Thr Arg Ser Pro Ala Leu Leu Leu
                             1               5 ctg cta ttg ggg gcc ctc ccg tcg gct gag gcg gcg cga gga ccc cca    161
Leu Leu Leu Gly Ala Leu Pro Ser Ala Glu Ala Ala Arg Gly Pro Pro
 10              15                  20                  25 aga atg gca gac aaa gtg gtc cca cgg cag gtg gcc cgc ctg ggc cgc    209
Arg Met Ala Asp Lys Val Val Pro Arg Gln Val Ala Arg Leu Gly Arg
             30                  35                  40 act gtg cgg cta cag tgc cca gtg gag ggg gac cca cca ccg ttg acc    257
Thr Val Arg Leu Gln Cys Pro Val Glu Gly Asp Pro Pro Pro Leu Thr
                 45                  50                  55 atg tgg acc aaa gat ggc cgc aca atc cac agt ggc tgg agc cgc ttc    305
Met Trp Thr Lys Asp Gly Arg Thr Ile His Ser Gly Trp Ser Arg Phe
             60                  65                  70 cgt gtg ctg ccc cag ggt ctg aag gtg aag gag gtg gag gcc gag gat    353
Arg Val Leu Pro Gln Gly Leu Lys Val Lys Glu Val Glu Ala Glu Asp
 75                  80                  85 gcc ggt gtt tat gtg tgc aag gcc acc aat ggc ttt ggc agc ctc agc    401
Ala Gly Val Tyr Val Cys Lys Ala Thr Asn Gly Phe Gly Ser Leu Ser
 90                  95                 100                 105 gtc aac tac act ctc atc atc atg gat gat att agt cca ggg aag gag    449
Val Asn Tyr Thr Leu Ile Ile Met Asp Asp Ile Ser Pro Gly Lys Glu
                110                 115                 120 agc cct ggg cca ggt ggt tct tcg ggg ggc cag gag gac cca gcc agc    497
Ser Pro Gly Pro Gly Gly Ser Ser Gly Gly Gln Glu Asp Pro Ala Ser
                125                 130                 135 cag cag tgg gca cgg cct cgc ttc aca cag ccc tcc aag atg agg cgc    545
Gln Gln Trp Ala Arg Pro Arg Phe Thr Gln Pro Ser Lys Met Arg Arg
            140                 145                 150 cga gtg att gca cgg cct gtg ggt agc tct gtg cgg ctc aag tgt gtg    593
Arg Val Ile Ala Arg Pro Val Gly Ser Ser Val Arg Leu Lys Cys Val
            155                 160                 165 gcc agt ggg cac cca cgg cca gac atc atg tgg atg aag gat gac cag    641
Ala Ser Gly His Pro Arg Pro Asp Ile Met Trp Met Lys Asp Asp Gln
170                 175                 180                 185 acc ttg acg cat cta gag gct agt gaa cac aga aag aag aag tgg aca    689
Thr Leu Thr His Leu Glu Ala Ser Glu His Arg Lys Lys Lys Trp Thr
                190                 195                 200
```

FIG. 1B

| | | | | | | | | | | | | | | | |
|---|---|---|---|---|---|---|---|---|---|---|---|---|---|---|---|
| ctg | agc | ttg | aag | aac | ctg | aag | cct | gaa | gac | agt | ggc | aag | tac | acg | tgc | 737 |
| Leu | Ser | Leu | Lys | Asn | Leu | Lys | Pro | Glu | Asp | Ser | Gly | Lys | Tyr | Thr | Cys | |
| | | | 205 | | | | 210 | | | | | 215 | | | | | cgt gta tct aac aag gcc ggt gcc atc aac gcc acc tac aaa gtg gat    785
Arg Val Ser Asn Lys Ala Gly Ala Ile Asn Ala Thr Tyr Lys Val Asp
         220             225             230 gta atc cag cgg act cgt tcc aag cct gtg ctc aca ggg aca cac cct    833
Val Ile Gln Arg Thr Arg Ser Lys Pro Val Leu Thr Gly Thr His Pro
         235             240             245 gtg aac aca acg gtg gac ttc ggt ggg aca acg tcc ttc cag tgc aag    881
Val Asn Thr Thr Val Asp Phe Gly Gly Thr Thr Ser Phe Gln Cys Lys
250             255             260             265 gtg cgc agt gac gtg aag cct gtg atc cag tgg ctg aag cgg gtg gag    929
Val Arg Ser Asp Val Lys Pro Val Ile Gln Trp Leu Lys Arg Val Glu
         270             275             280 tac ggc tcc gag gga cgc cac aac tcc acc att gat gtg ggt ggc cag    977
Tyr Gly Ser Glu Gly Arg His Asn Ser Thr Ile Asp Val Gly Gly Gln
         285             290             295 aag ttt gtg gtg ttg ccc acg ggt gat gtg tgg tca cgg cct gat ggc   1025
Lys Phe Val Val Leu Pro Thr Gly Asp Val Trp Ser Arg Pro Asp Gly
         300             305             310 tcc tac ctc aac aag ctg ctc atc tct cgg gcc cgc cag gat gat gct   1073
Ser Tyr Leu Asn Lys Leu Leu Ile Ser Arg Ala Arg Gln Asp Asp Ala
         315             320             325 ggc atg tac atc tgc cta ggt gca aat acc atg ggc tac agt ttc cgt   1121
Gly Met Tyr Ile Cys Leu Gly Ala Asn Thr Met Gly Tyr Ser Phe Arg
330             335             340             345 agc gcc ttc ctc act gta tta cca gac ccc aaa cct cca ggg cct cct   1169
Ser Ala Phe Leu Thr Val Leu Pro Asp Pro Lys Pro Pro Gly Pro Pro
         350             355             360 atg gct tct tca tcg tca tcc aca agc ctg cca tgg cct gtg gtg atc   1217
Met Ala Ser Ser Ser Ser Thr Ser Leu Pro Trp Pro <u>Val Val Ile</u>
         365             370             375 ggc atc cca gct ggt gct gtc ttc atc cta ggc act gtg ctg ctc tgg   1265
<u>Gly Ile Pro Ala Gly Ala Val Phe Ile Leu Gly Thr Val Leu Leu Trp</u>
         380             385             390 ctt tgc cag acc aag aag aag cca tgt gcc cca gca tct aca ctt cct   1313
<u>Leu Cys</u> Gln Thr Lys Lys Lys Pro Cys Ala Pro Ala Ser Thr Leu Pro
         395             400             405

FIG. 1C

```
gtg cct ggg cat cgt ccc cca ggg aca tcc cga gaa cgc agt ggt gac    1361
Val Pro Gly His Arg Pro Pro Gly Thr Ser Arg Glu Arg Ser Gly Asp
410                 415                 420                 425 aag gac ctg ccc tca ttg gct gtg ggc ata tgt gag gag cat gga tcc    1409
Lys Asp Leu Pro Ser Leu Ala Val Gly Ile Cys Glu Glu His Gly Ser
            430                 435                 440 gcc atg gcc ccc cag cac atc ctg gcc tct ggc tca act gct ggc ccc    1457
Ala Met Ala Pro Gln His Ile Leu Ala Ser Gly Ser Thr Ala Gly Pro
                445                 450                 455 aag ctg tac ccc aag cta tac aca gat gtg cac aca cac aca cat aca    1505
Lys Leu Tyr Pro Lys Leu Tyr Thr Asp Val His Thr His Thr His Thr
            460                 465                 470 cac acc tgc act cac acg ctc tca tgt gga ggg caa ggt tca tca aca    1553
His Thr Cys Thr His Thr Leu Ser Cys Gly Gly Gln Gly Ser Ser Thr
    475                 480                 485 cca gca tgt cca cta tca gtg cta aat aca gcg aat ctc caa gca ctg    1601
Pro Ala Cys Pro Leu Ser Val Leu Asn Thr Ala Asn Leu Gln Ala Leu
490                 495                 500                 505 tgt cct gag gta ggc ata tgg ggg cca agg caa cag gtt ggg aga att    1649
Cys Pro Glu Val Gly Ile Trp Gly Pro Arg Gln Gln Val Gly Arg Ile
                510                 515                 520 gag aac aat gga gga aga gta tct tag ggtgccttat ggtggacact          1696
Glu Asn Asn Gly Gly Arg Val Ser
                525                 530 cacaaacttg gccatataga tgtatgtact accagatgaa cagccagcca gattcacaca  1756
cgcacatgtt taaacgtgta aacgtgtgca caactgcaca cacaacctga gaaaccttca  1816
ggaggatttg tggtgtgact ttgcagtgac atgtagcgat ggctagttga aggaatctcc  1876
ctcatgtctt agtggtcatg gccacttccc caccoctgcc catctgtgtt cctgcctggc  1936
cttggtgtgc ttccgtgtgc cctgggtatc aggagcctat catcaacctg actggggtga  1996
gcagtgcagc catgcctgga ggtttgagcc accctcccct tgctagagag aagggcctca  2056
atatttatat ttaagaaatg aaataatatt aataataatg taaggagggc tgggacacag  2116
ggactctggc cttccctggg gcctgggacc tgcctggcct tgtggttaca ttgggtaccc  2176
tcactgtcca tggctgcctg gtctctgtaa ttttatatag agtttgagct gaagcctcgt  2236
atatttaatt tattttgtta aacaagaaaa aaaaaaaaa a                      2277
```

FIG. 2A

```
gcggccgcga ccccaggtcc ggacaggccg ag atg acg ccg agc ccc ctg ttg    53
                                    Met Thr Pro Ser Pro Leu Leu
                                     1               5 ctg ctc ctg ctg ccg ccg ctg ctg ctg ggg gcc ttc cca ccg gcc gcc   101
Leu Leu Leu Leu Pro Pro Leu Leu Leu Gly Ala Phe Pro Pro Ala Ala
            10                  15                  20 gcc gcc cga ggc ccc cca aag atg gcg gac aag gtg gtc cca cgg cag   149
Ala Ala Arg Gly Pro Pro Lys Met Ala Asp Lys Val Val Pro Arg Gln
        25                  30                  35 gtg gcc cgg ctg ggc cgc act gtg cgg ctg cag tgc cca gtg gag ggg   197
Val Ala Arg Leu Gly Arg Thr Val Arg Leu Gln Cys Pro Val Glu Gly
 40                  45                  50                  55 gac ccg ccg ccg ctg acc atg tgg acc aag gat ggc cgc acc atc cac   245
Asp Pro Pro Pro Leu Thr Met Trp Thr Lys Asp Gly Arg Thr Ile His
                60                  65                  70 agc ggc tgg agc cgc ttc cgc gtg ctg ccg cag ggg ctg aag gtg aag   293
Ser Gly Trp Ser Arg Phe Arg Val Leu Pro Gln Gly Leu Lys Val Lys
            75                  80                  85 cag gtg gag cgg gag gat gcc ggc gtg tac gtg tgc aag gcc acc aac   341
Gln Val Glu Arg Glu Asp Ala Gly Val Tyr Val Cys Lys Ala Thr Asn
        90                  95                 100 ggc ttc ggc agc ctg agc gtc aac tac acc ctc gtc gtg ctg gat gac   389
Gly Phe Gly Ser Leu Ser Val Asn Tyr Thr Leu Val Val Leu Asp Asp
       105                 110                 115 att agc cca ggg aag gag agc ctg ggg ccc gac agc tcc tct ggg ggt   437
Ile Ser Pro Gly Lys Glu Ser Leu Gly Pro Asp Ser Ser Ser Gly Gly
120                 125                 130                 135 caa gag gac ccc gcc agc cag cag tgg gca cga ccg cgc ttc aca cag   485
Gln Glu Asp Pro Ala Ser Gln Gln Trp Ala Arg Pro Arg Phe Thr Gln
                140                 145                 150 ccc tcc aag atg agg cgc cgg gtg atc gca cgg ccc gtg ggt agc tcc   533
Pro Ser Lys Met Arg Arg Arg Val Ile Ala Arg Pro Val Gly Ser Ser
            155                 160                 165 gtg cgg ctc aag tgc gtg gcc agc ggg cac cct cgg ccc gac atc acg   581
Val Arg Leu Lys Cys Val Ala Ser Gly His Pro Arg Pro Asp Ile Thr
        170                 175                 180 tgg atg aag gac gac cag gcc ttg acg cgc cca gag gcc gct gag ccc   629
Trp Met Lys Asp Asp Gln Ala Leu Thr Arg Pro Glu Ala Ala Glu Pro
185                 190                 195
```

FIG. 2B

```
agg aag aag aag tgg aca ctg agc ctg aag aac ctg cgg ccg gag gac    677
Arg Lys Lys Lys Trp Thr Leu Ser Leu Lys Asn Leu Arg Pro Glu Asp
200             205             210             215 agc ggc aaa tac acc tgc cgc gtg tcg aac cgc gcg ggc gcc atc aac    725
Ser Gly Lys Tyr Thr Cys Arg Val Ser Asn Arg Ala Gly Ala Ile Asn
        220             225             230 gcc acc tac aag gtg gat gtg atc cag cgg acc cgt tcc aag ccc gtg    773
Ala Thr Tyr Lys Val Asp Val Ile Gln Arg Thr Arg Ser Lys Pro Val
            235             240             245 ctc aca ggc acg cac ccc gtg aac acg acg gtg gac ttc ggg ggg acc    821
Leu Thr Gly Thr His Pro Val Asn Thr Thr Val Asp Phe Gly Gly Thr
        250             255             260 acg tcc ttc cag tgc aag gtg cgc agc gac gtg aag ccg gtg atc cag    869
Thr Ser Phe Gln Cys Lys Val Arg Ser Asp Val Lys Pro Val Ile Gln
265             270             275 tgg ctg aag cgc gtg gag tac ggc gct gag ggc cgc cac aac tcc acc    917
Trp Leu Lys Arg Val Glu Tyr Gly Ala Glu Gly Arg His Asn Ser Thr
280             285             290             295 atc gat gtg ggc ggc cag aag ttt gtg gtg ctg ccc acg ggt gac gtg    965
Ile Asp Val Gly Gly Gln Lys Phe Val Val Leu Pro Thr Gly Asp Val
            300             305             310 tgg tcg cgg ccc gac ggc tcc tac ctc aat aag ctg ctc atc acc cgt   1013
Trp Ser Arg Pro Asp Gly Ser Tyr Leu Asn Lys Leu Leu Ile Thr Arg
        315             320             325 gcc cgc cag gac gat gcg ggc atg tac atc tgc ctt ggc gcc aac acc   1061
Ala Arg Gln Asp Asp Ala Gly Met Tyr Ile Cys Leu Gly Ala Asn Thr
        330             335             340 atg ggc tac agc ttc cgc agc gcc ttc ctc acc gtg ctg cca gac cca   1109
Met Gly Tyr Ser Phe Arg Ser Ala Phe Leu Thr Val Leu Pro Asp Pro
345             350             355 aaa ccg cca ggg cca cct gtg gcc tcc tcg tcc tcg gcc act agc ctg   1157
Lys Pro Pro Gly Pro Pro Val Ala Ser Ser Ser Ser Ala Thr Ser Leu
360             365             370             375 ccg tgg ccc gtg gtc atc ggc atc cca gcc ggc gct gtc ttc atc ctg   1205
Pro Trp Pro Val Val Ile Gly Ile Pro Ala Gly Ala Val Phe Ile Leu
            380             385             390 ggc acc ctg ctc ctg tgg ctt tgc cag gcc cag aag aag ccg tgc acc   1253
Gly Thr Leu Leu Leu Trp Leu Cys Gln Ala Gln Lys Lys Pro Cys Thr
        395             400             405
```

FIG. 2C

```
ccc gcg cct gcc cct ccc ctg cct ggg cac cgc ccg ccg ggg acg gcc    1301
Pro Ala Pro Ala Pro Pro Leu Pro Gly His Arg Pro Pro Gly Thr Ala
        410                 415                 420 cgc gac cgc agc gga gac aag gac ctt ccc tcg ttg gcc gcc ctc agc    1349
Arg Asp Arg Ser Gly Asp Lys Asp Leu Pro Ser Leu Ala Ala Leu Ser
        425                 430                 435 gct ggc cct ggt gtg ggg ctg tgt gag gag cat ggg tct ccg gca gcc    1397
Ala Gly Pro Gly Val Gly Leu Cys Glu Glu His Gly Ser Pro Ala Ala
440                 445                 450                 455 ccc cag cac tta ctg ggc cca ggc cca gtt gct ggc cct aag ttg tac    1445
Pro Gln His Leu Leu Gly Pro Gly Pro Val Ala Gly Pro Lys Leu Tyr
                460                 465                 470 ccc ta                                                              1450
Pro
```

FIG. 3A

```
muFGFR-L   1   ..............MTRSPALLLLLLGALPSAEAARGPP.....RMADKV   31
               ||  ||||  ||  |  .  ||  |       :|: |
neFGFR-4   1   MGVQKDSRDIRWNRTTRPLALLLCGLLAFSALSCARTLPEGRKANLAELV   50 muFGFR-L   32  VPRQVARL...GRTVRLQCPVEGDPPPLTMWTKDGRTIHSGWSRFRVLPQ   78
               :   |   |  .|| |    .:|.  | ||  | | |.
neFGFR-4   51  SEEEEHFLLDPGNALRLFCDT.NQTTIVNWYTESTRLQHGG..RIRLTDT   97 muFGFR-L   79  GLKVKEVEAEDAGVYVCKATNGFGSLSVNYTLIIMDDISPG...KESPGP   125
               |.: :|  ||.|.|.|   | |  :  |:|: :.|  :. |     | |
neFGFR-4   98  VLEIADVTYEDSGLYLC.VVPGTGHILRNFTISVVDSLASGDDDDEDHGR   146 muFGFR-L   126 GGSSG..GQEDPASQQWARPRFTQPSKMRRRVIARPVGSSVRLKCVASGH   173
               |.|  |::  |  |   |  ..|| :|  ::.  |  |  ..|: :|  ..|.
neFGFR-4   147 EDSAGDMGEDPPYSTSYRAPFWSQPQRMDKKLYAVPAGNTVKFRCPSAGN   196 muFGFR-L   174 PRPDIMWMKDDQTL...THLEASEHRKKKWTLSLKNLKPEDSGKYTCRVS   220
               | | |  |:|..       :         |  .|.|  :...| | | ||| |
neFGFR-4   197 PTPGIRWLKNGREFGGEHRIGGIRLRHQHWSLVMESVVPSDRGNYTCLVE   246 muFGFR-L   221 NKAGAINATYKVDVIQRTRSKPVLTGTHPVNTTVDFGGTTSFQCKVRSDV   270
               ||  |.|.  .|  .|.||::|.    :|:|      | |||  |   | ||| ||
neFGFR-4   247 NKFGSISYSYLLDVLERSPHRPILQAGLPANTTAMLGSDVQFFCKVYSDA   296 muFGFR-L   271 KPVIQWLKRVEYGSEGRHNSTIDVGGQKFV.VLPTGDVWSRPDGSYLNKL   319
               .| |||||  :|     .|    |    | || || | |:   .| . |
neFGFR-4   297 QPHIQWLKHIEV.....NGSRYGPDGVPFVQVLKTADI....NSSEVEVL   337 muFGFR-L   320 LISRARQDDAGMYICLGANTMGYSFRSAFLTVLPDPKPPGPPMASSSSST   369
               :    :||| | ||  |..| |:.||.|||||:         .|
neFGFR-4   338 YLHNVSFEDAGEYTCLAGNSIGLSYQSAWLTVLPEEDFAKEAEGPETRYT   387 muFGFR-L   370 SLPWPVVIGIPAGAVFILGTVLLWLCQTKKKPCAPASTLPVPGHRPPGTS   419
               ::|         ::   |:. ||. .               |  |  ||
neFGFR-4   388 D....IIIYTSGSLALLMAAVIVVLCRMQLP........PTKTHLEPATV   425 muFGFR-L   420 RERSGDKDLPSLAVGICEEHGSAMAPQHILASGSTAGPKLYPKLYTDVHT   469
               . |   :  ..     |..  :   |. | | | |.
neFGFR-4   426 HKLSRFPLMRQFSLESSSSGKSSTSLVRVTRLSSSCTPMLPGVLEFDLPL   475
```

FIG. 3B

```
muFGFR-L  470 HTHTHTCTHTLSCGGQGSSTPACPLSVLNTANLQALCPEVGIWGPRQQVG 519
                | |                  :     |:  |         .:
neFGFR-4  476 DSKWEFPRERLVLGKPLGEGCFGQVVRAEAYGINKDQPDKAI.TVAIKIV 524 muFGFR-L  520 RIENNGGRVS*................................. 530
                :  .    .|
neFGFR-4  525 KDKGTDKELSDLISEMELMKLMGKHKNIINLLGVCTQDGPLYMIVEYASK 574
```

FIG. 4

```
  1 MTPSPLLLLLLPPLLLGAFPPAAAARGPPKMADKVVPRQVARLGRTVRLQ  50
    || || |||    ||||| |  |||||||:|||||||||||||||||||
  1 MTRSPALLL....LLLGALPSAEAARGPPRMADKVVPRQVARLGRTVRLQ  46

51 CPVEGDPPPLTMWTKDGRTIHSGWSRFRVLPQGLKVKQVEREDAGVYVCK 100
    |||||||||||||||||||||||||||||||||||||:|| ||||||||
 47 CPVEGDPPPLTMWTKDGRTIHSGWSRFRVLPQGLKVKEVEAEDAGVYVCK  96

101 ATNGFGSLSVNYTLVVLDDISPGKESLGPDSSSGGQEDPASQQWARPRFT 150
    |||||||||||||:::|||||||||| || |||||||||||||||||||
 97 ATNGFGSLSVNYTLIIMDDISPGKESPGPGGSSGGQEDPASQQWARPRFT 146

151 QPSKMRRRVIARPVGSSVRLKCVASGHPRPDITWMKDDQALTRPEAAEPR 200
    |||||||||||||||||||||||||||||||| |||||| ||  ||·| |
147 QPSKMRRRVIARPVGSSVRLKCVASGHPRPDIMWMKDDQTLTHLEASEHR 196

201 KKKWTLSLKNLRPEDSGKYTCRVSNRAGAINATYKVDVIQRTRSKPVLTG 250
    ||||||||||:||||||||||||||:|||||||||||||||||||||||
197 KKKWTLSLKNLKPEDSGKYTCRVSNKAGAINATYKVDVIQRTRSKPVLTG 246

251 THPVNTTVDFGGTTSFQCKVRSDVKPVIQWLKRVEYGAEGRHNSTIDVGG 300
    ||||||||||||||||||||||||||||||||||||| ·|||||||||||
247 THPVNTTVDFGGTTSFQCKVRSDVKPVIQWLKRVEYGSEGRHNSTIDVGG 296

301 QKFVVLPTGDVWSRPDGSYLNKLLITRARQDDAGMYICLGANTMGYSFRS 350
    |||||||||||||||||||||||||·||||||||||||||||||||||||
297 QKFVVLPTGDVWSRPDGSYLNKLLISRARQDDAGMYICLGANTMGYSFRS 346

351 AFLTVLPDPKPPGPPVASSSSATSLPWPVVIGIPAGAVFILGTLLLWLCQ 400
    ||||||||||||||·|||||·||||||||||||||||||||||·|||||
347 AFLTVLPDPKPPGPPMASSSSSTSLPWPVVIGIPAGAVFILGTVLLWLCQ 396

401 AQKKPCTPAPAPPLPGHRPPGTARDRSGDKDLPSLAALSAGPGVGLCEEH 450
        ·|||| ||   |·||||||||·|:||||||||||  ||:||||
397 TKKKPCAPASTLPVPGHRPPGTSRERSGDKDLPSLA.......VGICEEH 439

451 GSPAAPQHLLGPGPVAGPKLYPKLYTDIHTHTHTHSHTHSHVEGKVHQHI 500
    || ||||:|   | ||||||||||||:||||||· ||·
440 GSAMAPQHILASGSTAGPKLYPKLYTDVHTHTHTHTCTHTLSCGGQGSST 489

501 HYQC* 504

490 PACPLSVLNTANLQALCPEVGIWGPRQQVGRIENNGGRVS* 529
```

FIG. 18

CHO FRL/ECD-Fc
E. Coli FRL/ECD

— 200 kD

— 97 kD
— 69 kD

— 46 kD

— 30 kD

SEQUENCE LISTING

```
<160> NUMBER OF SEQ ID NOS: 22

<210> SEQ ID NO 1
<211> LENGTH: 2277
<212> TYPE: DNA
<213> ORGANISM: Mus musculus
<220> FEATURE:
<221> NAME/KEY: CDS
<222> LOCATION: (87)..(1673)
<221> NAME/KEY: sig_peptide
<222> LOCATION: (87)..(146)
<221> NAME/KEY: misc_feature
<222> LOCATION: (1208)..(1271)
<223> OTHER INFORMATION: predicted transmembrane domain

<400> SEQUENCE: 1
gacctgggtc ttgcgggcct gagccctgag tggcgtccag tccagctccc agtgaccgcg      60
cccctgcttc aggtccgacc ggcgag atg acg cgg agc ccc gcg ctg ctg ctg     113
                             Met Thr Arg Ser Pro Ala Leu Leu Leu
                               1               5 ctg cta ttg ggg gcc ctc ccg tcg gct gag gcg gcg cga gga ccc cca     161
Leu Leu Leu Gly Ala Leu Pro Ser Ala Glu Ala Ala Arg Gly Pro Pro
 10              15                  20                  25 aga atg gca gac aaa gtg gtc cca cgg cag gtg gcc cgc ctg ggc cgc     209
Arg Met Ala Asp Lys Val Val Pro Arg Gln Val Ala Arg Leu Gly Arg
                 30                  35                  40 act gtg cgg cta cag tgc cca gtg gag ggg gac cca cca ccg ttg acc     257
Thr Val Arg Leu Gln Cys Pro Val Glu Gly Asp Pro Pro Pro Leu Thr
             45                  50                  55 atg tgg acc aaa gat ggc cgc aca atc cac agt ggc tgg agc cgc ttc     305
Met Trp Thr Lys Asp Gly Arg Thr Ile His Ser Gly Trp Ser Arg Phe
         60                  65                  70 cgt gtg ctg ccc cag ggt ctg aag gtg aag gag gtg gag gcc gag gat     353
Arg Val Leu Pro Gln Gly Leu Lys Val Lys Glu Val Glu Ala Glu Asp
     75                  80                  85
```

```
gcc ggt gtt tat gtg tgc aag gcc acc aat ggc ttt ggc agc ctc agc    401
Ala Gly Val Tyr Val Cys Lys Ala Thr Asn Gly Phe Gly Ser Leu Ser
 90              95                 100                 105 gtc aac tac act ctc atc atc atg gat gat att agt cca ggg aag gag    449
Val Asn Tyr Thr Leu Ile Ile Met Asp Asp Ile Ser Pro Gly Lys Glu
                 110                 115                 120 agc cct ggg cca ggt ggt tct tcg ggg ggc cag gag gac cca gcc agc    497
Ser Pro Gly Pro Gly Gly Ser Ser Gly Gly Gln Glu Asp Pro Ala Ser
             125                 130                 135 cag cag tgg gca cgg cct cgc ttc aca cag ccc tcc aag atg agg cgc    545
Gln Gln Trp Ala Arg Pro Arg Phe Thr Gln Pro Ser Lys Met Arg Arg
         140                 145                 150 cga gtg att gca cgg cct gtg ggt agc tct gtg cgg ctc aag tgt gtg    593
Arg Val Ile Ala Arg Pro Val Gly Ser Ser Val Arg Leu Lys Cys Val
155                 160                 165 gcc agt ggg cac cca cgg cca gac atc atg tgg atg aag gat gac cag    641
Ala Ser Gly His Pro Arg Pro Asp Ile Met Trp Met Lys Asp Asp Gln
170                 175                 180                 185 acc ttg acg cat cta gag gct agt gaa cac aga aag aag aag tgg aca    689
Thr Leu Thr His Leu Glu Ala Ser Glu His Arg Lys Lys Lys Trp Thr
                 190                 195                 200 ctg agc ttg aag aac ctg aag cct gaa gac agt ggc aag tac acg tgc    737
Leu Ser Leu Lys Asn Leu Lys Pro Glu Asp Ser Gly Lys Tyr Thr Cys
             205                 210                 215 cgt gta tct aac aag gcc ggt gcc atc aac gcc acc tac aaa gtg gat    785
Arg Val Ser Asn Lys Ala Gly Ala Ile Asn Ala Thr Tyr Lys Val Asp
         220                 225                 230 gta atc cag cgg act cgt tcc aag cct gtg ctc aca ggg aca cac cct    833
Val Ile Gln Arg Thr Arg Ser Lys Pro Val Leu Thr Gly Thr His Pro
235                 240                 245 gtg aac aca acg gtg gac ttc ggt ggg aca acg tcc ttc cag tgc aag    881
Val Asn Thr Thr Val Asp Phe Gly Gly Thr Thr Ser Phe Gln Cys Lys
250                 255                 260                 265 gtg cgc agt gac gtg aag cct gtg atc cag tgg ctg aag cgg gtg gag    929
Val Arg Ser Asp Val Lys Pro Val Ile Gln Trp Leu Lys Arg Val Glu
                 270                 275                 280 tac ggc tcc gag gga cgc cac aac tcc acc att gat gtg ggt ggc cag    977
Tyr Gly Ser Glu Gly Arg His Asn Ser Thr Ile Asp Val Gly Gly Gln
             285                 290                 295 aag ttt gtg gtg ttg ccc acg ggt gat gtg tgg tca cgg cct gat ggc    1025
Lys Phe Val Val Leu Pro Thr Gly Asp Val Trp Ser Arg Pro Asp Gly
         300                 305                 310 tcc tac ctc aac aag ctc ctc atc tct cgg gcc cgc cag gat gat gct    1073
Ser Tyr Leu Asn Lys Leu Leu Ile Ser Arg Ala Arg Gln Asp Asp Ala
315                 320                 325 ggc atg tac atc tgc cta ggt gca aat acc atg ggc tac agt ttc cgt    1121
Gly Met Tyr Ile Cys Leu Gly Ala Asn Thr Met Gly Tyr Ser Phe Arg
330                 335                 340                 345 agc gcc ttc ctc act gta tta cca gac ccc aaa cct cca ggg cct cct    1169
Ser Ala Phe Leu Thr Val Leu Pro Asp Pro Lys Pro Pro Gly Pro Pro
                 350                 355                 360 atg gct tct tca tcg tca tcc aca agc ctg cca tgg cct gtg gtg atc    1217
Met Ala Ser Ser Ser Ser Ser Thr Ser Leu Pro Trp Pro Val Val Ile
             365                 370                 375 ggc atc cca gct ggt gct gtc ttc atc cta ggc act gtg ctg ctc tgg    1265
Gly Ile Pro Ala Gly Ala Val Phe Ile Leu Gly Thr Val Leu Leu Trp
         380                 385                 390 ctt tgc cag acc aag aag aag cca tgt gcc cca gca tct aca ctt cct    1313
Leu Cys Gln Thr Lys Lys Lys Pro Cys Ala Pro Ala Ser Thr Leu Pro
395                 400                 405
```

-continued

```
gtg cct ggg cat cgt ccc cca ggg aca tcc cga gaa cgc agt ggt gac    1361
Val Pro Gly His Arg Pro Pro Gly Thr Ser Arg Glu Arg Ser Gly Asp
410                 415                 420                 425 aag gac ctg ccc tca ttg gct gtg ggc ata tgt gag gag cat gga tcc    1409
Lys Asp Leu Pro Ser Leu Ala Val Gly Ile Cys Glu Glu His Gly Ser
            430                 435                 440 gcc atg gcc ccc cag cac atc ctg gcc tct ggc tca act gct ggc ccc    1457
Ala Met Ala Pro Gln His Ile Leu Ala Ser Gly Ser Thr Ala Gly Pro
        445                 450                 455 aag ctg tac ccc aag cta tac aca gat gtg cac aca cac aca cat aca    1505
Lys Leu Tyr Pro Lys Leu Tyr Thr Asp Val His Thr His Thr His Thr
    460                 465                 470 cac acc tgc act cac acg ctc tca tgt gga ggg caa ggt tca tca aca    1553
His Thr Cys Thr His Thr Leu Ser Cys Gly Gly Gln Gly Ser Ser Thr
475                 480                 485 cca gca tgt cca cta tca gtg cta aat aca gcg aat ctc caa gca ctg    1601
Pro Ala Cys Pro Leu Ser Val Leu Asn Thr Ala Asn Leu Gln Ala Leu
490                 495                 500                 505 tgt cct gag gta ggc ata tgg ggg cca agg caa cag gtt ggg aga att    1649
Cys Pro Glu Val Gly Ile Trp Gly Pro Arg Gln Gln Val Gly Arg Ile
            510                 515                 520 gag aac aat gga gga aga gta tct tagggtgcct tatggtggac actcacaaac  1703
Glu Asn Asn Gly Gly Arg Val Ser
        525 ttggccatat agatgtatgt actaccagat gaacagccag ccagattcac acacgcacat  1763
gtttaaacgt gtaaacgtgt gcacaactgc acacacaacc tgagaaacct tcaggaggat  1823
ttgtggtgtg actttgcagt gacatgtagc gatggctagt tgaaggaatc tccctcatgt  1883
cttagtggtc atggccactt ccccacccct gcccatctgt gttcctgcct ggccttggtg  1943
tgcttccgtg tgccctgggt atcaggagcc tatcatcaac ctgactgggg tgagcagtgc  2003
agccatgcct ggaggtttga gccacccctcc ccttgctaga gagaagggcc tcaatattta  2063
tatttaagaa atgaaataat attaataata atgtaaggag ggctgggaca cagggactct  2123
ggccttccct ggggcctggg acctgcctgg ccttgtggtt acattgggta ccctcactgt  2183
ccatggctgc ctggtctctg taattttata tagagtttga gctgaagcct cgtatattta  2243
atttattttg ttaaacaaga aaaaaaaaa aaaa                                2277
```

<210> SEQ ID NO 2
<211> LENGTH: 529
<212> TYPE: PRT
<213> ORGANISM: Mus musculus

<400> SEQUENCE: 2

```
Met Thr Arg Ser Pro Ala Leu Leu Leu Leu Leu Gly Ala Leu Pro
  1               5                  10                  15

Ser Ala Glu Ala Ala Arg Gly Pro Pro Arg Met Ala Asp Lys Val Val
                 20                  25                  30

Pro Arg Gln Val Ala Arg Leu Gly Arg Thr Val Arg Leu Gln Cys Pro
             35                  40                  45

Val Glu Gly Asp Pro Pro Leu Thr Met Trp Thr Lys Asp Gly Arg
         50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95
```

-continued

```
Ala Thr Asn Gly Phe Gly Ser Leu Ser Val Asn Tyr Thr Leu Ile Ile
            100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Ala Arg Pro Arg
            130                 135                 140

Phe Thr Gln Pro Ser Lys Met Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Trp Thr Leu Ser Leu Lys Asn Leu Lys
            195                 200                 205

Pro Glu Asp Ser Gly Lys Tyr Thr Cys Arg Val Ser Asn Lys Ala Gly
            210                 215                 220

Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
            260                 265                 270

Val Ile Gln Trp Leu Lys Arg Val Glu Tyr Gly Ser Glu Gly Arg His
            275                 280                 285

Asn Ser Thr Ile Asp Val Gly Gly Gln Lys Phe Val Val Leu Pro Thr
            290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
            340                 345                 350

Pro Asp Pro Lys Pro Pro Gly Pro Pro Met Ala Ser Ser Ser Ser
            355                 360                 365

Thr Ser Leu Pro Trp Pro Val Val Ile Gly Ile Pro Ala Gly Ala Val
            370                 375                 380

Phe Ile Leu Gly Thr Val Leu Leu Trp Leu Cys Gln Thr Lys Lys Lys
385                 390                 395                 400

Pro Cys Ala Pro Ala Ser Thr Leu Pro Val Pro Gly His Arg Pro Pro
                405                 410                 415

Gly Thr Ser Arg Glu Arg Ser Gly Asp Lys Asp Leu Pro Ser Leu Ala
            420                 425                 430

Val Gly Ile Cys Glu Glu His Gly Ser Ala Met Ala Pro Gln His Ile
            435                 440                 445

Leu Ala Ser Gly Ser Thr Ala Gly Pro Lys Leu Tyr Pro Lys Leu Tyr
            450                 455                 460

Thr Asp Val His Thr His Thr His Thr Cys Thr His Thr Leu
465                 470                 475                 480

Ser Cys Gly Gly Gln Gly Ser Ser Thr Pro Ala Cys Pro Leu Ser Val
                485                 490                 495

Leu Asn Thr Ala Asn Leu Gln Ala Leu Cys Pro Glu Val Gly Ile Trp
            500                 505                 510

Gly Pro Arg Gln Gln Val Gly Arg Ile Glu Asn Asn Gly Gly Arg Val
```

-continued

```
                 515                 520                 525
Ser

<210> SEQ ID NO 3
<211> LENGTH: 509
<212> TYPE: PRT
<213> ORGANISM: Mus musculus
<220> FEATURE:
<221> NAME/KEY: TRANSMEM
<222> LOCATION: (355)..(375)

<400> SEQUENCE: 3

Ala Arg Gly Pro Pro Arg Met Ala Asp Lys Val Val Pro Arg Gln Val
 1               5                  10                  15

Ala Arg Leu Gly Arg Thr Val Arg Leu Gln Cys Pro Val Glu Gly Asp
            20                  25                  30

Pro Pro Leu Thr Met Trp Thr Lys Asp Gly Arg Thr Ile His Ser
        35                  40                  45

Gly Trp Ser Arg Phe Arg Val Leu Pro Gln Gly Leu Lys Val Lys Glu
     50                  55                  60

Val Glu Ala Glu Asp Ala Gly Val Tyr Val Cys Lys Ala Thr Asn Gly
 65                  70                  75                  80

Phe Gly Ser Leu Ser Val Asn Tyr Thr Leu Ile Ile Met Asp Asp Ile
                85                  90                  95

Ser Pro Gly Lys Glu Ser Pro Gly Pro Gly Ser Ser Gly Gly Gln
            100                 105                 110

Glu Asp Pro Ala Ser Gln Gln Trp Ala Arg Pro Arg Phe Thr Gln Pro
        115                 120                 125

Ser Lys Met Arg Arg Val Ile Ala Arg Pro Val Gly Ser Ser Val
    130                 135                 140

Arg Leu Lys Cys Val Ala Ser Gly His Pro Arg Pro Asp Ile Met Trp
145                 150                 155                 160

Met Lys Asp Asp Gln Thr Leu Thr His Leu Glu Ala Ser Glu His Arg
                165                 170                 175

Lys Lys Lys Trp Thr Leu Ser Leu Lys Asn Leu Lys Pro Glu Asp Ser
            180                 185                 190

Gly Lys Tyr Thr Cys Arg Val Ser Asn Lys Ala Gly Ala Ile Asn Ala
        195                 200                 205

Thr Tyr Lys Val Asp Val Ile Gln Arg Thr Arg Ser Lys Pro Val Leu
    210                 215                 220

Thr Gly Thr His Pro Val Asn Thr Thr Val Asp Phe Gly Gly Thr Thr
225                 230                 235                 240

Ser Phe Gln Cys Lys Val Arg Ser Asp Val Lys Pro Val Ile Gln Trp
                245                 250                 255

Leu Lys Arg Val Glu Tyr Gly Ser Glu Gly Arg His Asn Ser Thr Ile
            260                 265                 270

Asp Val Gly Gly Gln Lys Phe Val Val Leu Pro Thr Gly Asp Val Trp
        275                 280                 285

Ser Arg Pro Asp Gly Ser Tyr Leu Asn Lys Leu Leu Ile Ser Arg Ala
    290                 295                 300

Arg Gln Asp Asp Ala Gly Met Tyr Ile Cys Leu Gly Ala Asn Thr Met
305                 310                 315                 320

Gly Tyr Ser Phe Arg Ser Ala Phe Leu Thr Val Leu Pro Asp Pro Lys
                325                 330                 335

Pro Pro Gly Pro Pro Met Ala Ser Ser Ser Ser Thr Ser Leu Pro
```

```
                340             345             350
Trp Pro Val Val Ile Gly Ile Pro Ala Gly Ala Val Phe Ile Leu Gly
            355                 360                 365
Thr Val Leu Leu Trp Leu Cys Gln Thr Lys Lys Lys Pro Cys Ala Pro
        370                 375                 380
Ala Ser Thr Leu Pro Val Pro Gly His Arg Pro Gly Thr Ser Arg
385                 390                 395                 400
Glu Arg Ser Gly Asp Lys Asp Leu Pro Ser Leu Ala Val Gly Ile Cys
                405                 410                 415
Glu Glu His Gly Ser Ala Met Ala Pro Gln His Ile Leu Ala Ser Gly
            420                 425                 430
Ser Thr Ala Gly Pro Lys Leu Tyr Pro Lys Leu Tyr Thr Asp Val His
        435                 440                 445
Thr His Thr His Thr His Thr Cys Thr His Thr Leu Ser Cys Gly Gly
        450                 455                 460
Gln Gly Ser Ser Thr Pro Ala Cys Pro Leu Ser Val Leu Asn Thr Ala
465                 470                 475                 480
Asn Leu Gln Ala Leu Cys Pro Glu Val Gly Ile Trp Gly Pro Arg Gln
                485                 490                 495
Gln Val Gly Arg Ile Glu Asn Asn Gly Gly Arg Val Ser
                500                 505

<210> SEQ ID NO 4
<211> LENGTH: 1450
<212> TYPE: DNA
<213> ORGANISM: Homo sapiens
<220> FEATURE:
<221> NAME/KEY: CDS
<222> LOCATION: (33)..(1448)
<221> NAME/KEY: sig_peptide
<222> LOCATION: (33)..(104)
<221> NAME/KEY: misc_feature
<222> LOCATION: (1167)..(1229)

<400> SEQUENCE: 4
gcggccgcga ccccaggtcc ggacaggccg ag atg acg ccg agc ccc ctg ttg        53
                                   Met Thr Pro Ser Pro Leu Leu
                                     1               5 ctg ctc ctg ctg ccg ccg ctg ctg ctg ggg gcc ttc cca ccg gcc gcc       101
Leu Leu Leu Leu Pro Pro Leu Leu Leu Gly Ala Phe Pro Pro Ala Ala
            10                  15                  20 gcc gcc cga ggc ccc cca aag atg gcg gac aag gtg gtc cca cgg cag       149
Ala Ala Arg Gly Pro Pro Lys Met Ala Asp Lys Val Val Pro Arg Gln
 25                  30                  35 gtg gcc cgg ctg ggc cgc act gtg cgg ctg cag tgc cca gtg gag ggg       197
Val Ala Arg Leu Gly Arg Thr Val Arg Leu Gln Cys Pro Val Glu Gly
 40                  45                  50                  55 gac ccg ccg ccg ctg acc atg tgg acc aag gat ggc cgc acc atc cac       245
Asp Pro Pro Pro Leu Thr Met Trp Thr Lys Asp Gly Arg Thr Ile His
                60                  65                  70 agc ggc tgg agc cgc ttc cgc gtg ctg ccg cag ggg ctg aag gtg aag       293
Ser Gly Trp Ser Arg Phe Arg Val Leu Pro Gln Gly Leu Lys Val Lys
            75                  80                  85 cag gtg gag cgg gag gat gcc ggc gtg tac gtg tgc aag gcc acc aac       341
Gln Val Glu Arg Glu Asp Ala Gly Val Tyr Val Cys Lys Ala Thr Asn
        90                  95                 100 ggc ttc ggc agc ctg agc gtc aac tac acc ctc gtc gtg ctg gat gac       389
Gly Phe Gly Ser Leu Ser Val Asn Tyr Thr Leu Val Val Leu Asp Asp
    105                 110                 115
```

-continued

| | | |
|---|---|---|
| att agc cca ggg aag gag agc ctg ggg ccc gac agc tcc tct ggg ggt<br>Ile Ser Pro Gly Lys Glu Ser Leu Gly Pro Asp Ser Ser Ser Gly Gly<br>120               125               130               135 | | 437 |
| caa gag gac ccc gcc agc cag cag tgg gca cga ccg cgc ttc aca cag<br>Gln Glu Asp Pro Ala Ser Gln Gln Trp Ala Arg Pro Arg Phe Thr Gln<br>            140               145               150 | | 485 |
| ccc tcc aag atg agg cgc cgg gtg atc gca cgg ccc gtg ggt agc tcc<br>Pro Ser Lys Met Arg Arg Arg Val Ile Ala Arg Pro Val Gly Ser Ser<br>            155               160               165 | | 533 |
| gtg cgg ctc aag tgc gtg gcc agc ggg cac cct cgg ccc gac atc acg<br>Val Arg Leu Lys Cys Val Ala Ser Gly His Pro Arg Pro Asp Ile Thr<br>170               175               180 | | 581 |
| tgg atg aag gac gac cag gcc ttg acg cgc cca gag gcc gct gag ccc<br>Trp Met Lys Asp Asp Gln Ala Leu Thr Arg Pro Glu Ala Ala Glu Pro<br>           185               190               195 | | 629 |
| agg aag aag aag tgg aca ctg agc ctg aag aac ctg cgg ccg gag gac<br>Arg Lys Lys Lys Trp Thr Leu Ser Leu Lys Asn Leu Arg Pro Glu Asp<br>200               205               210               215 | | 677 |
| agc ggc aaa tac acc tgc cgc gtg tcg aac cgc gcg ggc gcc atc aac<br>Ser Gly Lys Tyr Thr Cys Arg Val Ser Asn Arg Ala Gly Ala Ile Asn<br>               220               225               230 | | 725 |
| gcc acc tac aag gtg gat gtg atc cag cgg acc cgt tcc aag ccc gtg<br>Ala Thr Tyr Lys Val Asp Val Ile Gln Arg Thr Arg Ser Lys Pro Val<br>            235               240               245 | | 773 |
| ctc aca ggc acg cac ccc gtg aac acg acg gtg gac ttc ggg ggg acc<br>Leu Thr Gly Thr His Pro Val Asn Thr Thr Val Asp Phe Gly Gly Thr<br>               250               255               260 | | 821 |
| acg tcc ttc cag tgc aag gtg cgc agc gac gtg aag ccg gtg atc cag<br>Thr Ser Phe Gln Cys Lys Val Arg Ser Asp Val Lys Pro Val Ile Gln<br>265               270               275 | | 869 |
| tgg ctg aag cgc gtg gag tac ggc gct gag ggc cgc cac aac tcc acc<br>Trp Leu Lys Arg Val Glu Tyr Gly Ala Glu Gly Arg His Asn Ser Thr<br>280               285               290               295 | | 917 |
| atc gat gtg ggc ggc cag aag ttt gtg gtg ctg ccc acg ggt gac gtg<br>Ile Asp Val Gly Gly Gln Lys Phe Val Val Leu Pro Thr Gly Asp Val<br>               300               305               310 | | 965 |
| tgg tcg cgg ccc gac ggc tcc tac ctc aat aag ctg ctc atc acc cgt<br>Trp Ser Arg Pro Asp Gly Ser Tyr Leu Asn Lys Leu Leu Ile Thr Arg<br>            315               320               325 | | 1013 |
| gcc cgc cag gac gat gcg ggc atg tac atc tgc ctt ggc gcc aac acc<br>Ala Arg Gln Asp Asp Ala Gly Met Tyr Ile Cys Leu Gly Ala Asn Thr<br>               330               335               340 | | 1061 |
| atg ggc tac agc ttc cgc agc gcc ttc ctc acc gtg ctg cca gac cca<br>Met Gly Tyr Ser Phe Arg Ser Ala Phe Leu Thr Val Leu Pro Asp Pro<br>345               350               355 | | 1109 |
| aaa ccg cca ggg cca cct gtg gcc tcc tcg tcc tcg gcc act agc ctg<br>Lys Pro Pro Gly Pro Pro Val Ala Ser Ser Ser Ser Ala Thr Ser Leu<br>360               365               370               375 | | 1157 |
| ccg tgg ccc gtg gtc atc ggc atc cca gcc ggc gct gtc ttc atc ctg<br>Pro Trp Pro Val Val Ile Gly Ile Pro Ala Gly Ala Val Phe Ile Leu<br>            380               385               390 | | 1205 |
| ggc acc ctg ctc ctg tgg ctt tgc cag gcc cag aag aag ccg tgc acc<br>Gly Thr Leu Leu Leu Trp Leu Cys Gln Ala Gln Lys Lys Pro Cys Thr<br>               395               400               405 | | 1253 |
| ccc gcg cct gcc cct ccc ctg cct ggg cac cgc ccg ggg acg gcc<br>Pro Ala Pro Ala Pro Pro Leu Pro Gly His Arg Pro Pro Gly Thr Ala<br>            410               415               420 | | 1301 |
| cgc gac cgc agc gga gac aag gac ctt ccc tcg ttg gcc gcc ctc agc<br>Arg Asp Arg Ser Gly Asp Lys Asp Leu Pro Ser Leu Ala Ala Leu Ser<br>425               430               435 | | 1349 |

-continued

```
gct ggc cct ggt gtg ggg ctg tgt gag gag cat ggg tct ccg gca gcc      1397
Ala Gly Pro Gly Val Gly Leu Cys Glu Glu His Gly Ser Pro Ala Ala
440             445                 450                 455 ccc cag cac tta ctg ggc cca ggc cca gtt gct ggc cct aag ttg tac      1445
Pro Gln His Leu Leu Gly Pro Gly Pro Val Ala Gly Pro Lys Leu Tyr
                460                 465                 470 ccc ta                                                                1450
Pro
```

<210> SEQ ID NO 5
<211> LENGTH: 472
<212> TYPE: PRT
<213> ORGANISM: Homo sapiens

<400> SEQUENCE: 5

```
Met Thr Pro Ser Pro Leu Leu Leu Leu Leu Pro Pro Leu Leu Leu
 1               5                  10                  15

Gly Ala Phe Pro Ala Ala Ala Arg Gly Pro Pro Lys Met Ala
            20                  25                  30

Asp Lys Val Val Pro Arg Gln Val Ala Arg Leu Gly Arg Thr Val Arg
            35                  40                  45

Leu Gln Cys Pro Val Glu Gly Asp Pro Pro Leu Thr Met Trp Thr
 50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
            115                 120                 125

Pro Asp Ser Ser Gly Gly Gln Glu Asp Pro Ala Ser Gln Gln Trp
130                 135                 140

Ala Arg Pro Arg Phe Thr Gln Pro Ser Lys Met Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
            180                 185                 190

Arg Pro Glu Ala Ala Glu Pro Arg Lys Lys Lys Trp Thr Leu Ser Leu
        195                 200                 205

Lys Asn Leu Arg Pro Glu Asp Ser Gly Lys Tyr Thr Cys Arg Val Ser
210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
            260                 265                 270

Asp Val Lys Pro Val Ile Gln Trp Leu Lys Arg Val Glu Tyr Gly Ala
        275                 280                 285

Glu Gly Arg His Asn Ser Thr Ile Asp Val Gly Gly Gln Lys Phe Val
    290                 295                 300

Val Leu Pro Thr Gly Asp Val Trp Ser Arg Pro Asp Gly Ser Tyr Leu
305                 310                 315                 320
```

```
Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
            340                 345                 350

Leu Thr Val Leu Pro Asp Pro Lys Pro Pro Gly Pro Pro Val Ala Ser
        355                 360                 365

Ser Ser Ser Ala Thr Ser Leu Pro Trp Pro Val Val Ile Gly Ile Pro
370                 375                 380

Ala Gly Ala Val Phe Ile Leu Gly Thr Leu Leu Leu Trp Leu Cys Gln
385                 390                 395                 400

Ala Gln Lys Lys Pro Cys Thr Pro Ala Pro Ala Pro Pro Leu Pro Gly
                405                 410                 415

His Arg Pro Pro Gly Thr Ala Arg Asp Arg Ser Gly Asp Lys Asp Leu
            420                 425                 430

Pro Ser Leu Ala Ala Leu Ser Ala Gly Pro Gly Val Gly Leu Cys Glu
        435                 440                 445

Glu His Gly Ser Pro Ala Ala Pro Gln His Leu Leu Gly Pro Gly Pro
    450                 455                 460

Val Ala Gly Pro Lys Leu Tyr Pro
465                 470

<210> SEQ ID NO 6
<211> LENGTH: 448
<212> TYPE: PRT
<213> ORGANISM: Homo sapiens
<220> FEATURE:
<221> NAME/KEY: TRANSMEM
<222> LOCATION: (355)..(375)

<400> SEQUENCE: 6

Ala Arg Gly Pro Pro Lys Met Ala Asp Lys Val Val Pro Arg Gln Val
1               5                   10                  15

Ala Arg Leu Gly Arg Thr Val Arg Leu Gln Cys Pro Val Glu Gly Asp
            20                  25                  30

Pro Pro Pro Leu Thr Met Trp Thr Lys Asp Gly Arg Thr Ile His Ser
        35                  40                  45

Gly Trp Ser Arg Phe Arg Val Leu Pro Gln Gly Leu Lys Val Lys Gln
    50                  55                  60

Val Glu Arg Glu Asp Ala Gly Val Tyr Val Cys Lys Ala Thr Asn Gly
65                  70                  75                  80

Phe Gly Ser Leu Ser Val Asn Tyr Thr Leu Val Val Leu Asp Asp Ile
            85                  90                  95

Ser Pro Gly Lys Glu Ser Leu Gly Pro Asp Ser Ser Gly Gly Gln
        100                 105                 110

Glu Asp Pro Ala Ser Gln Gln Trp Ala Arg Pro Arg Phe Thr Gln Pro
    115                 120                 125

Ser Lys Met Arg Arg Arg Val Ile Ala Arg Pro Val Gly Ser Ser Val
130                 135                 140

Arg Leu Lys Cys Val Ala Ser Gly His Pro Arg Pro Asp Ile Thr Trp
145                 150                 155                 160

Met Lys Asp Asp Gln Ala Leu Thr Arg Pro Glu Ala Ala Glu Pro Arg
            165                 170                 175

Lys Lys Lys Trp Thr Leu Ser Leu Lys Asn Leu Arg Pro Glu Asp Ser
        180                 185                 190

Gly Lys Tyr Thr Cys Arg Val Ser Asn Arg Ala Gly Ala Ile Asn Ala
```

-continued

```
                195                 200                 205
Thr Tyr Lys Val Asp Val Ile Gln Arg Thr Arg Ser Lys Pro Val Leu
    210                 215                 220

Thr Gly Thr His Pro Val Asn Thr Thr Val Asp Phe Gly Gly Thr Thr
225                 230                 235                 240

Ser Phe Gln Cys Lys Val Arg Ser Asp Val Lys Pro Val Ile Gln Trp
            245                 250                 255

Leu Lys Arg Val Glu Tyr Gly Ala Glu Gly Arg His Asn Ser Thr Ile
                260                 265                 270

Asp Val Gly Gln Lys Phe Val Leu Pro Thr Gly Asp Val Trp
            275                 280                 285

Ser Arg Pro Asp Gly Ser Tyr Leu Asn Lys Leu Leu Ile Thr Arg Ala
    290                 295                 300

Arg Gln Asp Asp Ala Gly Met Tyr Ile Cys Leu Gly Ala Asn Thr Met
305                 310                 315                 320

Gly Tyr Ser Phe Arg Ser Ala Phe Leu Thr Val Leu Pro Asp Pro Lys
                325                 330                 335

Pro Pro Gly Pro Pro Val Ala Ser Ser Ser Ala Thr Ser Leu Pro
            340                 345                 350

Trp Pro Val Val Ile Gly Ile Pro Ala Gly Ala Val Phe Ile Leu Gly
                355                 360                 365

Thr Leu Leu Leu Trp Leu Cys Gln Ala Gln Lys Lys Pro Cys Thr Pro
    370                 375                 380

Ala Pro Ala Pro Pro Leu Pro Gly His Arg Pro Pro Gly Thr Ala Arg
385                 390                 395                 400

Asp Arg Ser Gly Asp Lys Asp Leu Pro Ser Leu Ala Ala Leu Ser Ala
                405                 410                 415

Gly Pro Gly Val Gly Leu Cys Glu Glu His Gly Ser Pro Ala Ala Pro
            420                 425                 430

Gln His Leu Leu Gly Pro Gly Pro Val Ala Gly Pro Lys Leu Tyr Pro
    435                 440                 445

<210> SEQ ID NO 7
<211> LENGTH: 574
<212> TYPE: PRT
<213> ORGANISM: Pleurodeles waltlii

<400> SEQUENCE: 7

Met Gly Val Gln Lys Asp Ser Arg Asp Ile Arg Trp Asn Arg Thr Thr
1               5                   10                  15

Arg Pro Leu Ala Leu Leu Leu Cys Gly Leu Leu Ala Phe Ser Ala Leu
                20                  25                  30

Ser Cys Ala Arg Thr Leu Pro Glu Gly Arg Lys Ala Asn Leu Ala Glu
            35                  40                  45

Leu Val Ser Glu Glu Glu His Phe Leu Leu Asp Pro Gly Asn Ala
        50                  55                  60

Leu Arg Leu Phe Cys Asp Thr Asn Gln Thr Thr Ile Val Asn Trp Tyr
65                  70                  75                  80

Thr Glu Ser Thr Arg Leu Gln His Gly Gly Arg Ile Arg Leu Thr Asp
                85                  90                  95

Thr Val Leu Glu Ile Ala Asp Val Thr Tyr Glu Asp Ser Gly Leu Tyr
                100                 105                 110

Leu Cys Val Val Pro Gly Thr Gly His Ile Leu Arg Asn Phe Thr Ile
            115                 120                 125
```

-continued

```
Ser Val Val Asp Ser Leu Ala Ser Gly Asp Asp Asp Glu Asp His
    130                 135                 140
Gly Arg Glu Asp Ser Ala Gly Asp Met Gly Glu Asp Pro Pro Tyr Ser
145                 150                 155                 160
Thr Ser Tyr Arg Ala Pro Phe Trp Ser Gln Pro Gln Arg Met Asp Lys
                165                 170                 175
Lys Leu Tyr Ala Val Pro Ala Gly Asn Thr Val Lys Phe Arg Cys Pro
            180                 185                 190
Ser Ala Gly Asn Pro Thr Pro Gly Ile Arg Trp Leu Lys Asn Gly Arg
        195                 200                 205
Glu Phe Gly Gly Glu His Arg Ile Gly Gly Ile Arg Leu Arg His Gln
    210                 215                 220
His Trp Ser Leu Val Met Glu Ser Val Val Pro Ser Asp Arg Gly Asn
225                 230                 235                 240
Tyr Thr Cys Leu Val Glu Asn Lys Phe Gly Ser Ile Ser Tyr Ser Tyr
                245                 250                 255
Leu Leu Asp Val Leu Glu Arg Ser Pro His Arg Pro Ile Leu Gln Ala
            260                 265                 270
Gly Leu Pro Ala Asn Thr Thr Ala Met Leu Gly Ser Asp Val Gln Phe
        275                 280                 285
Phe Cys Lys Val Tyr Ser Asp Ala Gln Pro His Ile Gln Trp Leu Lys
    290                 295                 300
His Ile Glu Val Asn Gly Ser Arg Tyr Gly Pro Asp Gly Val Pro Phe
305                 310                 315                 320
Val Gln Val Leu Lys Thr Ala Asp Ile Asn Ser Ser Glu Val Glu Val
                325                 330                 335
Leu Tyr Leu His Asn Val Ser Phe Glu Asp Ala Gly Glu Tyr Thr Cys
            340                 345                 350
Leu Ala Gly Asn Ser Ile Gly Leu Ser Tyr Gln Ser Ala Trp Leu Thr
        355                 360                 365
Val Leu Pro Glu Glu Asp Phe Ala Lys Glu Ala Glu Gly Pro Glu Thr
    370                 375                 380
Arg Tyr Thr Asp Ile Ile Ile Tyr Thr Ser Gly Ser Leu Ala Leu Leu
385                 390                 395                 400
Met Ala Ala Val Ile Val Val Leu Cys Arg Met Gln Leu Pro Pro Thr
                405                 410                 415
Lys Thr His Leu Glu Pro Ala Thr Val His Lys Leu Ser Arg Phe Pro
            420                 425                 430
Leu Met Arg Gln Phe Ser Leu Glu Ser Ser Ser Ser Gly Lys Ser Ser
        435                 440                 445
Thr Ser Leu Val Arg Val Thr Arg Leu Ser Ser Ser Cys Thr Pro Met
    450                 455                 460
Leu Pro Gly Val Leu Glu Phe Asp Leu Pro Leu Asp Ser Lys Trp Glu
465                 470                 475                 480
Phe Pro Arg Glu Arg Leu Val Leu Gly Lys Pro Leu Gly Glu Gly Cys
                485                 490                 495
Phe Gly Gln Val Val Arg Ala Glu Ala Tyr Gly Ile Asn Lys Asp Gln
            500                 505                 510
Pro Asp Lys Ala Ile Thr Val Ala Ile Lys Ile Val Lys Asp Lys Gly
        515                 520                 525
Thr Asp Lys Glu Leu Ser Asp Leu Ile Ser Glu Met Glu Leu Met Lys
    530                 535                 540
Leu Met Gly Lys His Lys Asn Ile Ile Asn Leu Leu Gly Val Cys Thr
```

-continued

```
               545                 550                 555                 560
Gln Asp Gly Pro Leu Tyr Met Ile Val Glu Tyr Ala Ser Lys
                565                 570

<210> SEQ ID NO 8
<211> LENGTH: 504
<212> TYPE: PRT
<213> ORGANISM: Artificial Sequence
<220> FEATURE:
<223> OTHER INFORMATION: Description of Artificial Sequence: virtual
      human FGFR-L amino acid sequence comprising residues
      1-472 of SEQ ID NO: 5 and residues 473-504 of
      GenBank accession no. AJ277437

<400> SEQUENCE: 8

Met Thr Pro Ser Pro Leu Leu Leu Leu Leu Pro Pro Leu Leu Leu
  1               5                  10                  15

Gly Ala Phe Pro Pro Ala Ala Ala Arg Gly Pro Pro Lys Met Ala
                 20                  25                  30

Asp Lys Val Val Pro Arg Gln Val Ala Arg Leu Gly Arg Thr Val Arg
                 35                  40                  45

Leu Gln Cys Pro Val Glu Gly Asp Pro Pro Leu Thr Met Trp Thr
         50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
                115                 120                 125

Pro Asp Ser Ser Gly Gly Gln Glu Asp Pro Ala Ser Gln Gln Trp
        130                 135                 140

Ala Arg Pro Arg Phe Thr Gln Pro Ser Lys Met Arg Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
                180                 185                 190

Arg Pro Glu Ala Ala Glu Pro Arg Lys Lys Lys Trp Thr Leu Ser Leu
                195                 200                 205

Lys Asn Leu Arg Pro Glu Asp Ser Gly Lys Tyr Thr Cys Arg Val Ser
        210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
                260                 265                 270

Asp Val Lys Pro Val Ile Gln Trp Leu Lys Arg Val Glu Tyr Gly Ala
                275                 280                 285

Glu Gly Arg His Asn Ser Thr Ile Asp Val Gly Gly Gln Lys Phe Val
        290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
```

-continued

```
                325                 330                 335
Ile Cys Leu Gly Ala Asn Thr Met Gly Tyr Ser Phe Arg Ser Ala Phe
            340                 345                 350
Leu Thr Val Leu Pro Asp Pro Lys Pro Pro Gly Pro Val Ala Ser
        355                 360                 365
Ser Ser Ser Ala Thr Ser Leu Pro Trp Pro Val Val Ile Gly Ile Pro
    370                 375                 380
Ala Gly Ala Val Phe Ile Leu Gly Thr Leu Leu Leu Trp Leu Cys Gln
385                 390                 395                 400
Ala Gln Lys Lys Pro Cys Thr Pro Ala Pro Ala Pro Pro Leu Pro Gly
                405                 410                 415
His Arg Pro Pro Gly Thr Ala Arg Asp Arg Ser Gly Asp Lys Asp Leu
            420                 425                 430
Pro Ser Leu Ala Ala Leu Ser Ala Gly Pro Gly Val Gly Leu Cys Glu
        435                 440                 445
Glu His Gly Ser Pro Ala Ala Pro Gln His Leu Leu Gly Pro Gly Pro
    450                 455                 460
Val Ala Gly Pro Lys Leu Tyr Pro Lys Leu Tyr Thr Asp Ile His Thr
465                 470                 475                 480
His Thr His Thr His Ser His Thr His Ser His Val Glu Gly Lys Val
                485                 490                 495
His Gln His Ile His Tyr Gln Cys
            500

<210> SEQ ID NO 9
<211> LENGTH: 11
<212> TYPE: PRT
<213> ORGANISM: Human immunodeficiency virus type 1

<400> SEQUENCE: 9

Tyr Gly Arg Lys Lys Arg Arg Gln Arg Arg Arg
 1               5                  10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:
      internalizing domain derived from HIV tat protein

<400> SEQUENCE: 10

Gly Gly Gly Gly Tyr Gly Arg Lys Lys Arg Arg Gln Arg Arg Arg
 1               5                  10                  15

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: predicted
      signal peptide of murine FGFR-L polypeptide

<400> SEQUENCE: 11

Met Thr Arg Ser Pro Ala Leu Leu Leu Leu Leu Gly Ala Leu Pro
 1               5                  10                  15

Ser Ala Glu Ala
            20

<210> SEQ ID NO 12
```

```
<211> LENGTH: 25
<212> TYPE: PRT
<213> ORGANISM: Artificial Sequence
<220> FEATURE:
<223> OTHER INFORMATION: Description of Artificial Sequence: predicted
      transmmebrane domain for murine FRL polypeptide

<400> SEQUENCE: 12

Leu Pro Trp Pro Val Val Ile Gly Ile Pro Ala Gly Ala Val Phe Ile
 1               5                  10                  15

Leu Gly Thr Val Leu Leu Trp Leu Cys
            20                  25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      oligonucleotide; PCR primer

<400> SEQUENCE: 13
cgctgaccat gtggaccaag gatg                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      oligonucleotide; PCR primer

<400> SEQUENCE: 14
cttgacccca gaaggagctg tcgg                                            24

<210> SEQ ID NO 15
<211> LENGTH: 504
<212> TYPE: PRT
<213> ORGANISM: Homo sapiens

<400> SEQUENCE: 15

Met Thr Pro Ser Pro Leu Leu Leu Leu Leu Pro Leu Leu Leu
 1               5                  10                  15

Gly Ala Phe Pro Pro Ala Ala Ala Arg Gly Pro Pro Lys Met Ala
            20                  25                  30

Asp Lys Val Val Pro Arg Gln Val Ala Arg Leu Gly Arg Thr Val Arg
        35                  40                  45

Leu Gln Cys Pro Val Glu Gly Asp Pro Pro Leu Thr Met Trp Thr
    50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
            100                 105                 110

Thr Leu Val Val Leu Asp Asp Ile Ser Pro Gly Lys Glu Ser Leu Gly
        115                 120                 125

Pro Asp Ser Ser Ser Gly Gly Gln Glu Asp Pro Ala Ser Gln Gln Trp
    130                 135                 140

Ala Arg Pro Arg Phe Thr Gln Pro Ser Lys Met Arg Arg Arg Val Ile
145                 150                 155                 160
```

-continued

```
Ala Arg Pro Val Gly Ser Ser Val Arg Leu Lys Cys Val Ala Ser Gly
            165                 170                 175

His Pro Arg Pro Asp Ile Thr Trp Met Lys Asp Asp Gln Ala Leu Thr
            180                 185                 190

Arg Pro Glu Ala Ala Glu Pro Arg Lys Lys Lys Trp Thr Leu Ser Leu
            195                 200                 205

Lys Asn Leu Arg Pro Glu Asp Ser Gly Lys Tyr Thr Cys Arg Val Ser
210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
            245                 250                 255

Thr Val Asp Phe Gly Gly Thr Thr Ser Phe Gln Cys Lys Val Arg Ser
            260                 265                 270

Asp Val Lys Pro Val Ile Gln Trp Leu Lys Arg Val Glu Tyr Gly Ala
            275                 280                 285

Glu Gly Arg His Asn Ser Thr Ile Asp Val Gly Gly Gln Lys Phe Val
            290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
            325                 330                 335

Ile Cys Leu Gly Ala Asn Thr Met Gly Tyr Ser Phe Arg Ser Ala Phe
            340                 345                 350

Leu Thr Val Leu Pro Asp Pro Lys Pro Gly Pro Pro Val Ala Ser
            355                 360                 365

Ser Ser Ser Ala Thr Ser Leu Pro Trp Pro Val Val Ile Gly Ile Pro
            370                 375                 380

Ala Gly Ala Val Phe Ile Leu Gly Thr Leu Leu Leu Trp Leu Cys Gln
385                 390                 395                 400

Ala Gln Lys Lys Pro Cys Thr Pro Ala Pro Ala Pro Pro Leu Pro Gly
            405                 410                 415

His Arg Pro Pro Gly Thr Ala Arg Asp Arg Ser Gly Asp Lys Asp Leu
            420                 425                 430

Pro Ser Leu Ala Ala Leu Ser Ala Gly Pro Gly Val Gly Leu Cys Glu
            435                 440                 445

Glu His Gly Ser Pro Ala Ala Pro Gln His Leu Leu Gly Pro Gly Pro
            450                 455                 460

Val Ala Gly Pro Lys Leu Tyr Pro Lys Leu Tyr Thr Asp Ile His Thr
465                 470                 475                 480

His Thr His Thr His Ser His Thr His Ser His Val Glu Gly Lys Val
            485                 490                 495

His Gln His Ile His Tyr Gln Cys
            500
```

<210> SEQ ID NO 16
<211> LENGTH: 3112
<212> TYPE: DNA
<213> ORGANISM: Homo sapiens
<220> FEATURE:
<221> NAME/KEY: CDS
<222> LOCATION: (25)..(1536)

<400> SEQUENCE: 16

```
gaccccaggt ccggacaggc cgag atg acg ccg agc ccc ctg ttg ctg ctc      51
                          Met Thr Pro Ser Pro Leu Leu Leu Leu
```

-continued

```
              1                   5
ctg ctg ccg ccg ctg ctg ctg ggg gcc ttc cca ccg gcc gcc gcc     99
Leu Leu Pro Pro Leu Leu Leu Gly Ala Phe Pro Pro Ala Ala Ala
 10              15                  20                  25 cga ggc ccc cca aag atg gcg gac aag gtg gtc cca cgg cag gtg gcc    147
Arg Gly Pro Pro Lys Met Ala Asp Lys Val Val Pro Arg Gln Val Ala
         30                  35                  40 cgg ctg ggc cgc act gtg cgg ctg cag tgc cca gtg gag ggg gac ccg    195
Arg Leu Gly Arg Thr Val Arg Leu Gln Cys Pro Val Glu Gly Asp Pro
             45                  50                  55 ccg ccg ctg acc atg tgg acc aag gat ggc cgc acc atc cac agc ggc    243
Pro Pro Leu Thr Met Trp Thr Lys Asp Gly Arg Thr Ile His Ser Gly
         60                  65                  70 tgg agc cgc ttc cgc gtg ctg ccg cag ggg ctg aag gtg aag cag gtg    291
Trp Ser Arg Phe Arg Val Leu Pro Gln Gly Leu Lys Val Lys Gln Val
     75                  80                  85 gag cgg gag gat gcc ggc gtg tac gtg tgc aag gcc acc aac ggc ttc    339
Glu Arg Glu Asp Ala Gly Val Tyr Val Cys Lys Ala Thr Asn Gly Phe
 90                  95                 100                 105 ggc agc ctt agc gtc aac tac acc ctc gtc gtg ctg gat gac att agc    387
Gly Ser Leu Ser Val Asn Tyr Thr Leu Val Val Leu Asp Asp Ile Ser
             110                 115                 120 cca ggg aag gag agc ctg ggg ccc gac agc tcc tct ggg ggt caa gag    435
Pro Gly Lys Glu Ser Leu Gly Pro Asp Ser Ser Ser Gly Gly Gln Glu
         125                 130                 135 gac ccc gcc agc cag cag tgg gca cga ccg cgc ttc aca cag ccc tcc    483
Asp Pro Ala Ser Gln Gln Trp Ala Arg Pro Arg Phe Thr Gln Pro Ser
         140                 145                 150 aag atg agg cgc cgg gtg atc gca cgg ccc gtg ggt agc tcc gtg cgg    531
Lys Met Arg Arg Arg Val Ile Ala Arg Pro Val Gly Ser Ser Val Arg
         155                 160                 165 ctc aag tgc gtg gcc agc ggg cac cct cgg ccc gac atc acg tgg atg    579
Leu Lys Cys Val Ala Ser Gly His Pro Arg Pro Asp Ile Thr Trp Met
170                 175                 180                 185 aag gac gac cag gcc ttg acg cgc cca gag gcc gct gag ccc agg aag    627
Lys Asp Asp Gln Ala Leu Thr Arg Pro Glu Ala Ala Glu Pro Arg Lys
             190                 195                 200 aag aag tgg aca ctg agc ctg aag aac ctg cgg ccg gag gac agc ggc    675
Lys Lys Trp Thr Leu Ser Leu Lys Asn Leu Arg Pro Glu Asp Ser Gly
         205                 210                 215 aaa tac acc tgc cgc gtg tcg aac cgc gcg ggc gcc atc aac gcc acc    723
Lys Tyr Thr Cys Arg Val Ser Asn Arg Ala Gly Ala Ile Asn Ala Thr
         220                 225                 230 tac aag gtg gat gtg atc cag cgg acc cgt tcc aag ccc gtg ctc aca    771
Tyr Lys Val Asp Val Ile Gln Arg Thr Arg Ser Lys Pro Val Leu Thr
     235                 240                 245 ggc acg cac ccc gtg aac acg acg gtg gac ttc ggg ggg acc acg tcc    819
Gly Thr His Pro Val Asn Thr Thr Val Asp Phe Gly Gly Thr Thr Ser
250                 255                 260                 265 ttc cag tgc aag gtg cgc agc gac gtg aag ccg gtg atc cag tgg ctg    867
Phe Gln Cys Lys Val Arg Ser Asp Val Lys Pro Val Ile Gln Trp Leu
             270                 275                 280 aag cgc gtg gag tac ggc gcc gag ggc cgc cac aac tcc acc atc gat    915
Lys Arg Val Glu Tyr Gly Ala Glu Gly Arg His Asn Ser Thr Ile Asp
             285                 290                 295 gtg ggc ggc cag aag ttt gtg gtg ctg ccc acg ggt gac gtg tgg tcg    963
Val Gly Gly Gln Lys Phe Val Val Leu Pro Thr Gly Asp Val Trp Ser
         300                 305                 310 cgg ccc gac ggc tcc tac ctc aat aag ctg ctc atc acc cgt gcc cgc    1011
```

```
                                                    -continued

Arg Pro Asp Gly Ser Tyr Leu Asn Lys Leu Leu Ile Thr Arg Ala Arg
    315                 320                 325 cag gac gat gcg ggc atg tac atc tgc ctt ggc gcc aac acc atg ggc      1059
Gln Asp Asp Ala Gly Met Tyr Ile Cys Leu Gly Ala Asn Thr Met Gly
330                 335                 340                 345 tac agc ttc cgc agc gcc ttc ctc acc gtg ctg cca gac cca aaa ccg      1107
Tyr Ser Phe Arg Ser Ala Phe Leu Thr Val Leu Pro Asp Pro Lys Pro
                350                 355                 360 caa ggg cca cct gtg gcc tcc tcg tcc tcg gcc act agc ctg ccg tgg      1155
Gln Gly Pro Pro Val Ala Ser Ser Ser Ser Ala Thr Ser Leu Pro Trp
            365                 370                 375 ccc gtg gtc atc ggc atc cca gcc ggc gct gtc ttc atc ctg ggc acc      1203
Pro Val Val Ile Gly Ile Pro Ala Gly Ala Val Phe Ile Leu Gly Thr
        380                 385                 390 ctg ctc ctg tgg ctt tgc cag gcc cag aag aag ccg tgc acc ccc gcg      1251
Leu Leu Leu Trp Leu Cys Gln Ala Gln Lys Lys Pro Cys Thr Pro Ala
    395                 400                 405 cct gcc cct ccc ctg cct ggg cac cgc ccg ccg ggg acg gcc ctc gac      1299
Pro Ala Pro Pro Leu Pro Gly His Arg Pro Pro Gly Thr Ala Leu Asp
410                 415                 420                 425 cgc agc gga gac aag gac ctt ccc tcg ttg gcc gcc ctc agc gct ggc      1347
Arg Ser Gly Asp Lys Asp Leu Pro Ser Leu Ala Ala Leu Ser Ala Gly
                430                 435                 440 cct ggt gtg ggg ctg tgt gag gag cat ggg tct ccg gca gcc ccc cag      1395
Pro Gly Val Gly Leu Cys Glu Glu His Gly Ser Pro Ala Ala Pro Gln
            445                 450                 455 cac tta ctg ggc cca ggc cca gtt gct ggc cct aag ttg tac ccc aaa      1443
His Leu Leu Gly Pro Gly Pro Val Ala Gly Pro Lys Leu Tyr Pro Lys
        460                 465                 470 ctc tac aca gac atc cac aca cac aca cac aca cac tct cac aca cac      1491
Leu Tyr Thr Asp Ile His Thr His Thr His Thr His Ser His Thr His
    475                 480                 485 tca cac gtg gag ggc aag gtc cac cag cac atc cac tat cag tgc          1536
Ser His Val Glu Gly Lys Val His Gln His Ile His Tyr Gln Cys
490                 495                 500 tagacggcac cgtatctgca gtgggcacgg ggggccggc cagacaggca gactgggagg    1596
atggaggacg gagctgcaga cgaaggcagg ggacccatgg cgaggaggaa tggccagcac    1656
cccaggcagt ctgtgtgtga ggcatagccc ctggacacac acacacagac acacacacta    1716
cctggatgca tgtatgcaca cacatgcgcg cacacgtgct ccctgaaggc acacgtacgc    1776
acacacgcac atgcacagat atgccgcctg gcacacagta taagctgccc aaatgcacgc    1836
acacgcacag agacatgcca gaacatacaa ggacatgctg cctgaacata cacacgcaca    1896
cccatgcgca gatgtgctgc ctggacacac acacacacac ggatatgctg tctggacgca    1956
cacacgtgca gatatggtat ccggacacac acgtgcacag atatgctgcc tggacacaca    2016
gataatgctg ccttgacaca cacatgcacg gatattgcct ggacacacac acacacacgc    2076
gtgcacagat atgctgtctg gacaggcaca catgcagata tgctgcctg gacacacac     2136 ttccagacac acgtgcacag gcgcagatat gctgcctgga cacacgcaga tatgctgtct    2196
agtcacacac acacgcagac atgctgtccg gacacacaca cgcatgcaca gatatgctgt    2256
ccggacacac acacgcacgc agatatgctg cctggacaca cacacagata tgctgcctc    2316 aacactcaca cacgtgcaga tattgcctgg acacacacat gtgcacagat atgctgtctg    2376
gacatgcaca cacgtgcaga tatgctgtcc ggatacacac gcacgcacac atgcagatat    2436
gctgcctggg cacacacttc cggacacaca tgcacacaca ggtgcagata tgctgcctgg    2496
```

-continued

```
acacacgcag actgacgtgc ttttgggagg gtgtgccgtg aagcctgcag tacgtgtgcc   2556
gtgaggctca tagttgatga gggactttcc ctgctccacc gtcactcccc caactctgcc   2616
cgcctctgtc cccgcctcag tccccgcctc catccccgcc tctgtcccct ggccttggcg   2676 gctattttg ccacctgcct tgggtgccca ggagtcccct actgctgtgg gctggggttg    2736
ggggcacagc agccccaagc ctgagaggct ggagcccatg gctagtggct catccccact   2796
gcattctccc cctgacacag agaagggggcc ttggtattta tatttaagaa atgaagataa  2856
tattaataat gatggaagga agactgggtt gcagggactg tggtctctcc tggggcccgg   2916
gacccgcctg gtctttcagc catgctgatg accacacccc gtccaggcca gacaccaccc   2976
cccaccccac tgtcgtggtg gccccagatc tctgtaattt tatgtagagt ttgagctgaa   3036
gccccgtata tttaatttat tttgttaaac atgaaagtgc atcctttccc tccaaaaaaa   3096
aaaaaaaaaa aaaaaa                                                   3112
```

<210> SEQ ID NO 17
<211> LENGTH: 504
<212> TYPE: PRT
<213> ORGANISM: Homo sapiens

<400> SEQUENCE: 17

```
Met Thr Pro Ser Pro Leu Leu Leu Leu Leu Pro Pro Leu Leu Leu
 1               5                  10                  15

Gly Ala Phe Pro Pro Ala Ala Ala Arg Gly Pro Pro Lys Met Ala
                20                  25                  30

Asp Lys Val Val Pro Arg Gln Val Ala Arg Leu Gly Arg Thr Val Arg
                35                  40                  45

Leu Gln Cys Pro Val Glu Gly Asp Pro Pro Leu Thr Met Trp Thr
 50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
                115                 120                 125

Pro Asp Ser Ser Gly Gly Gln Glu Asp Pro Ala Ser Gln Gln Trp
                130                 135                 140

Ala Arg Pro Arg Phe Thr Gln Pro Ser Lys Met Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Gln Ala Leu Thr
                180                 185                 190

Arg Pro Glu Ala Ala Glu Pro Arg Lys Lys Trp Thr Leu Ser Leu
                195                 200                 205

Lys Asn Leu Arg Pro Glu Asp Ser Gly Lys Tyr Thr Cys Arg Val Ser
                210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
```

-continued

```
             260                 265                 270
Asp Val Lys Pro Val Ile Gln Trp Leu Lys Arg Val Glu Tyr Gly Ala
            275                 280                 285

Glu Gly Arg His Asn Ser Thr Ile Asp Val Gly Gly Gln Lys Phe Val
        290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
            340                 345                 350

Leu Thr Val Leu Pro Asp Pro Lys Pro Gln Gly Pro Pro Val Ala Ser
        355                 360                 365

Ser Ser Ser Ala Thr Ser Leu Pro Trp Pro Val Val Ile Gly Ile Pro
370                 375                 380

Ala Gly Ala Val Phe Ile Leu Gly Thr Leu Leu Leu Trp Leu Cys Gln
385                 390                 395                 400

Ala Gln Lys Lys Pro Cys Thr Pro Ala Pro Ala Pro Pro Leu Pro Gly
                405                 410                 415

His Arg Pro Pro Gly Thr Ala Leu Asp Arg Ser Gly Asp Lys Asp Leu
            420                 425                 430

Pro Ser Leu Ala Ala Leu Ser Ala Gly Pro Gly Val Gly Leu Cys Glu
        435                 440                 445

Glu His Gly Ser Pro Ala Ala Pro Gln His Leu Leu Gly Pro Gly Pro
    450                 455                 460

Val Ala Gly Pro Lys Leu Tyr Pro Lys Leu Tyr Thr Asp Ile His Thr
465                 470                 475                 480

His Thr His Thr His Ser His Thr His Ser His Val Glu Gly Lys Val
                485                 490                 495

His Gln His Ile His Tyr Gln Cys
            500

<210> SEQ ID NO 18
<211> LENGTH: 3080
<212> TYPE: DNA
<213> ORGANISM: Homo sapiens
<220> FEATURE:
<221> NAME/KEY: CDS
<222> LOCATION: (23)..(1534)

<400> SEQUENCE: 18
ccccaggtcc ggacaggccg ag atg acg ccg agc ccc ctg ttg ctg ctc ctg       52
                         Met Thr Pro Ser Pro Leu Leu Leu Leu Leu
                           1               5                  10 ctg ccg ccg ctg ctg ctg ggg gcc ttc cca ccg gcc gcc gcc cga            100
Leu Pro Pro Leu Leu Leu Gly Ala Phe Pro Pro Ala Ala Ala Arg
                 15                  20                  25 ggc ccc cca aag atg gcg gac aag gtg gtc cca cgg cag gtg gcc cgg       148
Gly Pro Pro Lys Met Ala Asp Lys Val Val Pro Arg Gln Val Ala Arg
             30                  35                  40 ctg ggc cgc act gtg cgg ctg cag tgc cca gtg gag ggg gac ccg ccg       196
Leu Gly Arg Thr Val Arg Leu Gln Cys Pro Val Glu Gly Asp Pro Pro
         45                  50                  55 ccg ctg acc atg tgg acc aag gat ggc cgc acc atc cac agc ggc tgg       244
Pro Leu Thr Met Trp Thr Lys Asp Gly Arg Thr Ile His Ser Gly Trp
     60                  65                  70 agc cgc ttc cgc gtg ctg ccg cag ggg ctg aag gtg aag cag gtg gag       292
```

-continued

| | | |
|---|---|---|
| Ser Arg Phe Arg Val Leu Pro Gln Gly Leu Lys Val Lys Gln Val Glu<br>75                          80                                    85                              90 | |
| cgg gag gat gcc ggc gtg tac gtg tgc aag gcc acc aac ggc ttc ggc<br>Arg Glu Asp Ala Gly Val Tyr Val Cys Lys Ala Thr Asn Gly Phe Gly<br>                        95                                 100                             105 | 340 |
| agc ctt agc gtc aac tac acc ctc gtc gtg ctg gat gac att agc cca<br>Ser Leu Ser Val Asn Tyr Thr Leu Val Val Leu Asp Asp Ile Ser Pro<br>                      110                             115                             120 | 388 |
| ggg aag gag agc ctg ggg ccc gac agc tcc tct ggg ggt caa gag gac<br>Gly Lys Glu Ser Leu Gly Pro Asp Ser Ser Ser Gly Gly Gln Glu Asp<br>        125                             130                             135 | 436 |
| ccc gcc agc cag cag tgg gca cga ccg cgc ttc aca cag ccc tcc aag<br>Pro Ala Ser Gln Gln Trp Ala Arg Pro Arg Phe Thr Gln Pro Ser Lys<br>140                          145                             150 | 484 |
| atg agg cgc cgg gtg atc gca cgg ccc gtg ggt agc tcc gtg cgg ctc<br>Met Arg Arg Arg Val Ile Ala Arg Pro Val Gly Ser Ser Val Arg Leu<br>155                          160                             165                        170 | 532 |
| aag tgc gtg gcc agc ggg cac cct cgg ccc gac atc acg tgg atg aag<br>Lys Cys Val Ala Ser Gly His Pro Arg Pro Asp Ile Thr Trp Met Lys<br>                      175                             180                             185 | 580 |
| gac gac cag gcc ttg acg cgc cca gag gcc gct gag ccc agg aag aag<br>Asp Asp Gln Ala Leu Thr Arg Pro Glu Ala Ala Glu Pro Arg Lys Lys<br>                190                             195                             200 | 628 |
| aag tgg aca ctg agc ctg aag aac ctg cgg ccg gag gac agc ggc aaa<br>Lys Trp Thr Leu Ser Leu Lys Asn Leu Arg Pro Glu Asp Ser Gly Lys<br>        205                           210                             215 | 676 |
| tac acc tgc cgc gtg tcg aac cgc gcg ggc gcc atc aac gcc acc tac<br>Tyr Thr Cys Arg Val Ser Asn Arg Ala Gly Ala Ile Asn Ala Thr Tyr<br>220                          225                             230 | 724 |
| aag gtg gat gtg atc cag cgg acc cgt tcc aag ccc gtg ctc aca ggc<br>Lys Val Asp Val Ile Gln Arg Thr Arg Ser Lys Pro Val Leu Thr Gly<br>235                          240                             245                        250 | 772 |
| acg cac ccc gtg aac acg acg gtg gac ttc ggg ggg acc acg tcc ttc<br>Thr His Pro Val Asn Thr Thr Val Asp Phe Gly Gly Thr Thr Ser Phe<br>                      255                             260                             265 | 820 |
| cag tgc aag gtg cgc agc gac gtg aag ccg gtg atc cag tgg ctg aag<br>Gln Cys Lys Val Arg Ser Asp Val Lys Pro Val Ile Gln Trp Leu Lys<br>                270                             275                             280 | 868 |
| cgc gtg gag tac ggc gcc gag ggc cgc cac aac tcc acc atc gat gtg<br>Arg Val Glu Tyr Gly Ala Glu Gly Arg His Asn Ser Thr Ile Asp Val<br>        285                           290                           295 | 916 |
| ggc ggc cag aag ttt gtg gtg ctg ccc acg ggt gac gtg tgg tcg cgg<br>Gly Gly Gln Lys Phe Val Val Leu Pro Thr Gly Asp Val Trp Ser Arg<br>300                          305                             310 | 964 |
| ccc gac ggc tcc tac ctc aat aag ctg ctc atc acc cgt gcc cgc cag<br>Pro Asp Gly Ser Tyr Leu Asn Lys Leu Leu Ile Thr Arg Ala Arg Gln<br>315                        320                             325                        330 | 1012 |
| gac gat gcg ggc atg tac atc tgc ctt ggc gcc aac acc atg ggc tac<br>Asp Asp Ala Gly Met Tyr Ile Cys Leu Gly Ala Asn Thr Met Gly Tyr<br>                      335                             340                             345 | 1060 |
| agc ttc cgc agc gcc ttc ctc acc gtg ctg cca gac cca aaa ccg caa<br>Ser Phe Arg Ser Ala Phe Leu Thr Val Leu Pro Asp Pro Lys Pro Gln<br>        350                           355                             360 | 1108 |
| ggg cca cct gtg gcc tcc tcg tcc tcg gcc act agc ctg ccg tgg ccc<br>Gly Pro Pro Val Ala Ser Ser Ser Ser Ala Thr Ser Leu Pro Trp Pro<br>365                          370                             375 | 1156 |
| gtg gtc atc ggc atc cca gcc ggc gct gtc ttc atc ctg ggc acc ctg<br>Val Val Ile Gly Ile Pro Ala Gly Ala Val Phe Ile Leu Gly Thr Leu<br>380                          385                             390 | 1204 |

```
ctc ctg tgg ctt tgc cag gcc cag aag aag ccg tgc acc ccc gcg cct      1252
Leu Leu Trp Leu Cys Gln Ala Gln Lys Lys Pro Cys Thr Pro Ala Pro
395             400                 405                 410 gcc cct ccc ctg cct ggg cac cgc ccg ccg ggg acg gcc cgc gac cgc      1300
Ala Pro Pro Leu Pro Gly His Arg Pro Pro Gly Thr Ala Arg Asp Arg
            415                 420                 425 agc gga gac aag gac ctt ccc tcg ttg gcc gcc ctc agc gct ggc cct      1348
Ser Gly Asp Lys Asp Leu Pro Ser Leu Ala Ala Leu Ser Ala Gly Pro
        430                 435                 440 ggt gtg ggg ctg tgt gag gag cat ggg tct ccg gca gcc ccc cag cac      1396
Gly Val Gly Leu Cys Glu Glu His Gly Ser Pro Ala Ala Pro Gln His
    445                 450                 455 tta ctg ggc cca ggc cca gtt gct ggc cct aag ttg tac ccc aaa ctc      1444
Leu Leu Gly Pro Gly Pro Val Ala Gly Pro Lys Leu Tyr Pro Lys Leu
460                 465                 470 tac aca gac atc cac aca cac aca cac aca cac tct cac aca cac tca      1492
Tyr Thr Asp Ile His Thr His Thr His Thr His Ser His Thr His Ser
475             480                 485                 490 cac gtg gag ggc aag gtc cac cag cac atc cac tat cag tgc              1534
His Val Glu Gly Lys Val His Gln His Ile His Tyr Gln Cys
                495                 500 tagacggcac cgtatctgca gtgggcacgg gggggccggc cagacaggca gactgggagg    1594
atggaggacg gagctgcaga cgaaggcagg ggacccatgg cgaggaggaa tggccagcac    1654
cccaggcagt ctgtgtgtga ggcatagccc ctggacacac acacagac   acacacacta    1714
cctggatgca tgtatgcaca cacatgcgcg cacacgtgct ccctgaaggc acacgtacgc    1774
acacacgcac atgcacagat atgccgcctg ggcacacaga taagctgccc aaatgcacgc    1834
acacgcacag agacatgcca gaacatacaa ggacatgctg cctgaacata cacacgcaca    1894
cccatgcgca gatgtgctgc ctggacacac acacacacac ggatatgctg tctggacgca    1954
cacacgtgca gatatggtat ccggacacac acgtgcacag atatgctgcc tggacacaca    2014
gataatgctg ccttgacaca cacatgcacg gatattgcct ggacacacac acacacacgc    2074
gtgcacagat atgctgtctg gacaggcaca cacatgcaga tatgctgcct ggacacacac    2134
ttccagacac acgtgcacag gcgcagatat gctgcctgga cacacgcaga tatgctgtct    2194
agtcacacac acacgcagac atgctgtccg gacacacaca cgcatgcaca gatatgctgt    2254
ccggacacac acacgcacgc agatatgctg cctggacaca cacacagata atgctgcctc    2314
aacactcaca cacgtgcaga tattgcctgg acacacacat gtgcacagat atgctgtctg    2374
gacatgcaca cacgtgcaga tatgctgtcc ggatacacac gcacgcacac atgcagatat    2434
gctgcctggg cacacacttc cggacacaca tgcacacaca ggtgcagata tgctgcctgg    2494
acacacgcag actgacgtgc ttttgggagg gtgtgccgtg aagcctgcag tacgtgtgcc    2554
gtgaggctca tagttgatga gggactttcc ctgctccacc gtcactcccc caactctgcc    2614
cgcctctgtc cccgcctcag tccccgcctc catccccgcc tctgtcccct ggccttggcg    2674
gctattttg ccacctgcct tgggtgccca ggagtcccct actgctgtgg gctggggttg     2734
ggggcacagc agcccaagc ctgagaggct ggagcccatg gctagtggct catcccact      2794
gcattctccc cctgacacag agaagggcc ttggtattta tatttaagaa atgaagataa     2854
tattaataat gatggaagga agactgggtt gcagggactg tggtctctcc tggggccgg     2914
gacccgcctg gtctttcagc catgctgatg accacacccc gtccaggcca gacaccaccc    2974
cccacccac tgtcgtggtg ccccagatc tctgtaattt tatgtagagt ttgagctgaa      3034
gccccgtata tttaatttat tttgttaaac atgaaagtgc atcctt                   3080
```

<210> SEQ ID NO 19
<211> LENGTH: 504
<212> TYPE: PRT
<213> ORGANISM: Homo sapiens

<400> SEQUENCE: 19

```
Met Thr Pro Ser Pro Leu Leu Leu Leu Leu Pro Pro Leu Leu Leu
 1               5                  10                  15

Gly Ala Phe Pro Pro Ala Ala Ala Arg Gly Pro Pro Lys Met Ala
                 20                  25                  30

Asp Lys Val Val Pro Arg Gln Val Ala Arg Leu Gly Arg Thr Val Arg
             35                  40                  45

Leu Gln Cys Pro Val Glu Gly Asp Pro Pro Leu Thr Met Trp Thr
         50                  55                  60

Lys Asp Gly Arg Thr Ile His Ser Gly Trp Ser Arg Phe Arg Val Leu
     65                  70                  75                  80

Pro Gln Gly Leu Lys Val Lys Gln Val Glu Arg Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
         115                 120                 125

Pro Asp Ser Ser Ser Gly Gly Gln Glu Asp Pro Ala Ser Gln Gln Trp
     130                 135                 140

Ala Arg Pro Arg Phe Thr Gln Pro Ser Lys Met Arg Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
                180                 185                 190

Arg Pro Glu Ala Ala Glu Pro Arg Lys Lys Trp Thr Leu Ser Leu
             195                 200                 205

Lys Asn Leu Arg Pro Glu Asp Ser Gly Lys Tyr Thr Cys Arg Val Ser
        210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
                260                 265                 270

Asp Val Lys Pro Val Ile Gln Trp Leu Lys Arg Val Glu Tyr Gly Ala
            275                 280                 285

Glu Gly Arg His Asn Ser Thr Ile Asp Val Gly Gly Gln Lys Phe Val
        290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
                340                 345                 350

Leu Thr Val Leu Pro Asp Pro Lys Pro Gln Gly Pro Val Ala Ser
            355                 360                 365

Ser Ser Ser Ala Thr Ser Leu Pro Trp Pro Val Val Ile Gly Ile Pro
```

```
                    370                 375                 380
Ala Gly Ala Val Phe Ile Leu Gly Thr Leu Leu Trp Leu Cys Gln
385                 390                 395                 400

Ala Gln Lys Lys Pro Cys Thr Pro Ala Pro Ala Pro Leu Pro Gly
                405                 410                 415

His Arg Pro Pro Gly Thr Ala Arg Asp Arg Ser Gly Asp Lys Asp Leu
                420                 425                 430

Pro Ser Leu Ala Ala Leu Ser Ala Gly Pro Gly Val Gly Leu Cys Glu
                435                 440                 445

Glu His Gly Ser Pro Ala Ala Pro Gln His Leu Leu Gly Pro Gly Pro
            450                 455                 460

Val Ala Gly Pro Lys Leu Tyr Pro Lys Leu Tyr Thr Asp Ile His Thr
465                 470                 475                 480

His Thr His Thr His Ser His Thr His Ser His Val Glu Gly Lys Val
                485                 490                 495

His Gln His Ile His Tyr Gln Cys
            500
```

<210> SEQ ID NO 20
<211> LENGTH: 342
<212> TYPE: PRT
<213> ORGANISM: Mus musculus

<400> SEQUENCE: 20

```
Met Ala Asp Lys Val Val Pro Arg Gln Val Ala Arg Leu Gly Arg Thr
1               5                   10                  15

Val Arg Leu Gln Cys Pro Val Glu Gly Asp Pro Pro Leu Thr Met
                20                  25                  30

Trp Thr Lys Asp Gly Arg Thr Ile His Ser Gly Trp Ser Arg Phe Arg
                35                  40                  45

Val Leu Pro Gln Gly Leu Lys Val Lys Glu Val Glu Ala Glu Asp Ala
            50                  55                  60

Gly Val Tyr Val Cys Lys Ala Thr Asn Gly Phe Gly Ser Leu Ser Val
65                  70                  75                  80

Asn Tyr Thr Leu Ile Ile Met Asp Asp Ile Ser Pro Gly Lys Glu Ser
                85                  90                  95

Pro Gly Pro Gly Gly Ser Ser Gly Gly Gln Glu Asp Pro Ala Ser Gln
                100                 105                 110

Gln Trp Ala Arg Pro Arg Phe Thr Gln Pro Ser Lys Met Arg Arg Arg
            115                 120                 125

Val Ile Ala Arg Pro Val Gly Ser Ser Val Arg Leu Lys Cys Val Ala
            130                 135                 140

Ser Gly His Pro Arg Pro Asp Ile Met Trp Met Lys Asp Asp Gln Thr
145                 150                 155                 160

Leu Thr His Leu Glu Ala Ser Glu His Arg Lys Lys Trp Thr Leu
                165                 170                 175

Ser Leu Lys Asn Leu Lys Pro Glu Asp Ser Gly Lys Tyr Thr Cys Arg
                180                 185                 190

Val Ser Asn Lys Ala Gly Ala Ile Asn Ala Thr Tyr Lys Val Asp Val
            195                 200                 205

Ile Gln Arg Thr Arg Ser Lys Pro Val Leu Thr Gly Thr His Pro Val
        210                 215                 220

Asn Thr Thr Val Asp Phe Gly Gly Thr Thr Ser Phe Gln Cys Lys Val
225                 230                 235                 240
```

```
Arg Ser Asp Val Lys Pro Val Ile Gln Trp Leu Lys Arg Val Glu Tyr
            245                 250                 255

Gly Ser Glu Gly Arg His Asn Ser Thr Ile Asp Val Gly Gly Gln Lys
            260                 265                 270

Phe Val Val Leu Pro Thr Gly Asp Val Trp Ser Arg Pro Asp Gly Ser
            275                 280                 285

Tyr Leu Asn Lys Leu Leu Ile Ser Arg Ala Arg Gln Asp Asp Ala Gly
            290                 295                 300

Met Tyr Ile Cys Leu Gly Ala Asn Thr Met Gly Tyr Ser Phe Arg Ser
305                 310                 315                 320

Ala Phe Leu Thr Val Leu Pro Asp Pro Lys Pro Pro Gly Pro Pro Met
            325                 330                 335

Ala Ser Ser Ser Ser Ser
            340

<210> SEQ ID NO 21
<211> LENGTH: 1788
<212> TYPE: DNA
<213> ORGANISM: Artificial Sequence
<220> FEATURE:
<223> OTHER INFORMATION: Description of Artificial Sequence: murine
      FGFR-L extracellular domain-Fc fusion polypeptide
<221> NAME/KEY: CDS
<222> LOCATION: (1)..(1782)

<400> SEQUENCE: 21
```

| | | | | | | | | | | | | | | | | |
|---|---|---|---|---|---|---|---|---|---|---|---|---|---|---|---|---|
| atg | acg | cgg | agc | ccc | gcg | ctg | ctg | ctg | cta | ttg | ggg | gcc | ctc | ccg | | 48 |
| Met | Thr | Arg | Ser | Pro | Ala | Leu | Leu | Leu | Leu | Leu | Gly | Ala | Leu | Pro | | |
| 1 | | | | 5 | | | | | 10 | | | | | 15 | | |
| tcg | gct | gag | gcg | gcg | cga | gga | ccc | cca | aga | atg | gca | gac | aaa | gtg | gtc | 96 |
| Ser | Ala | Glu | Ala | Ala | Arg | Gly | Pro | Pro | Arg | Met | Ala | Asp | Lys | Val | Val | |
| | | | 20 | | | | | 25 | | | | | 30 | | | |
| cca | cgg | cag | gtg | gcc | cgc | ctg | ggc | cgc | act | gtg | cgg | cta | cag | tgc | cca | 144 |
| Pro | Arg | Gln | Val | Ala | Arg | Leu | Gly | Arg | Thr | Val | Arg | Leu | Gln | Cys | Pro | |
| | | 35 | | | | | 40 | | | | | 45 | | | | |
| gtg | gag | ggg | gac | cca | cca | ccg | ttg | acc | atg | tgg | acc | aaa | gat | ggc | cgc | 192 |
| Val | Glu | Gly | Asp | Pro | Pro | Pro | Leu | Thr | Met | Trp | Thr | Lys | Asp | Gly | Arg | |
| 50 | | | | | 55 | | | | | 60 | | | | | | |
| aca | atc | cac | agt | ggc | tgg | agc | cgc | ttc | cgt | gtg | ctg | ccc | cag | ggt | ctg | 240 |
| Thr | Ile | His | Ser | Gly | Trp | Ser | Arg | Phe | Arg | Val | Leu | Pro | Gln | Gly | Leu | |
| 65 | | | | 70 | | | | | 75 | | | | | 80 | | |
| aag | gtg | aag | gag | gtg | gag | gcc | gag | gat | gcc | ggt | gtt | tat | gtg | tgc | aag | 288 |
| Lys | Val | Lys | Glu | Val | Glu | Ala | Glu | Asp | Ala | Gly | Val | Tyr | Val | Cys | Lys | |
| | | | | 85 | | | | | 90 | | | | | 95 | | |
| gcc | acc | aat | ggc | ttt | ggc | agc | ctc | agc | gtc | aac | tac | act | ctc | atc | atc | 336 |
| Ala | Thr | Asn | Gly | Phe | Gly | Ser | Leu | Ser | Val | Asn | Tyr | Thr | Leu | Ile | Ile | |
| | | | 100 | | | | | 105 | | | | | 110 | | | |
| atg | gat | gat | att | agt | cca | ggg | aag | gag | agc | cct | ggg | cca | ggt | ggt | tct | 384 |
| Met | Asp | Asp | Ile | Ser | Pro | Gly | Lys | Glu | Ser | Pro | Gly | Pro | Gly | Gly | Ser | |
| | | 115 | | | | | 120 | | | | | 125 | | | | |
| tcg | ggg | ggc | cag | gag | gac | cca | gcc | agc | cag | cag | tgg | gca | cgg | cct | cgc | 432 |
| Ser | Gly | Gly | Gln | Glu | Asp | Pro | Ala | Ser | Gln | Gln | Trp | Ala | Arg | Pro | Arg | |
| | 130 | | | | | 135 | | | | | 140 | | | | | |
| ttc | aca | cag | ccc | tcc | aag | atg | agg | cgc | cga | gtg | att | gca | cgg | cct | gtg | 480 |
| Phe | Thr | Gln | Pro | Ser | Lys | Met | Arg | Arg | Arg | Val | Ile | Ala | Arg | Pro | Val | |
| 145 | | | | | 150 | | | | | 155 | | | | | 160 | |
| ggt | agc | tct | gtg | cgg | ctc | aag | tgt | gtg | gcc | agt | ggg | cac | cca | cgg | cca | 528 |
| Gly | Ser | Ser | Val | Arg | Leu | Lys | Cys | Val | Ala | Ser | Gly | His | Pro | Arg | Pro | |
| | | | | 165 | | | | | 170 | | | | | 175 | | |
| gac | atc | atg | tgg | atg | aag | gat | gac | cag | acc | ttg | acg | cat | cta | gag | gct | 576 |

```
Asp Ile Met Trp Met Lys Asp Asp Gln Thr Leu Thr His Leu Glu Ala
            180                 185                 190 agt gaa cac aga aag aag aag tgg aca ctg agc ttg aag aac ctg aag        624
Ser Glu His Arg Lys Lys Lys Trp Thr Leu Ser Leu Lys Asn Leu Lys
        195                 200                 205 cct gaa gac agt ggc aag tac acg tgc cgt gta tct aac aag gcc ggt        672
Pro Glu Asp Ser Gly Lys Tyr Thr Cys Arg Val Ser Asn Lys Ala Gly
    210                 215                 220 gcc atc aac gcc acc tac aaa gtg gat gta atc cag cgg act cgt tcc        720
Ala Ile Asn Ala Thr Tyr Lys Val Asp Val Ile Gln Arg Thr Arg Ser
225                 230                 235                 240 aag cct gtg ctc aca ggg aca cac cct gtg aac aca acg gtg gac ttc        768
Lys Pro Val Leu Thr Gly Thr His Pro Val Asn Thr Thr Val Asp Phe
                245                 250                 255 ggt ggg aca acg tcc ttc cag tgc aag gtg cgc agt gac gtg aag cct        816
Gly Gly Thr Thr Ser Phe Gln Cys Lys Val Arg Ser Asp Val Lys Pro
            260                 265                 270 gtg atc cag tgg ctg aag cgg gtg gag tac ggc tcc gag gga cgc cac        864
Val Ile Gln Trp Leu Lys Arg Val Glu Tyr Gly Ser Glu Gly Arg His
        275                 280                 285 aac tcc acc att gat gtg ggt ggc cag aag ttt gtg gtg ttg ccc acg        912
Asn Ser Thr Ile Asp Val Gly Gly Gln Lys Phe Val Val Leu Pro Thr
    290                 295                 300 ggt gat gtg tgg tca cgg cct gat ggc tcc tac ctc aac aag ctg ctc        960
Gly Asp Val Trp Ser Arg Pro Asp Gly Ser Tyr Leu Asn Lys Leu Leu
305                 310                 315                 320 atc tct cgg gcc cgc cag gat gat gct ggc atg tac atc tgc cta ggt       1008
Ile Ser Arg Ala Arg Gln Asp Asp Ala Gly Met Tyr Ile Cys Leu Gly
                325                 330                 335 gca aat acc atg ggc tac agt ttc cgt agc gcc ttc ctc act gta tta       1056
Ala Asn Thr Met Gly Tyr Ser Phe Arg Ser Ala Phe Leu Thr Val Leu
            340                 345                 350 cca gac ccc aaa cct cca ggg cct cct atg gct tct tca tcg gtc gac       1104
Pro Asp Pro Lys Pro Pro Gly Pro Pro Met Ala Ser Ser Ser Val Asp
        355                 360                 365 aaa act cac aca tgc cca ccg tgc cca gca cct gaa ctc ctg ggg gga       1152
Lys Thr His Thr Cys Pro Pro Cys Pro Ala Pro Glu Leu Leu Gly Gly
    370                 375                 380 ccg tca gtc ttc ctc ttc ccc cca aaa ccc aag gac acc ctc atg atc       1200
Pro Ser Val Phe Leu Phe Pro Pro Lys Pro Lys Asp Thr Leu Met Ile
385                 390                 395                 400 tcc cgg acc cct gag gtc aca tgc gtg gtg gtg gac gtg agc cac gaa       1248
Ser Arg Thr Pro Glu Val Thr Cys Val Val Val Asp Val Ser His Glu
                405                 410                 415 gac cct gag gtc aag ttc aac tgg tac gtg gac ggc gtg gag gtg cat       1296
Asp Pro Glu Val Lys Phe Asn Trp Tyr Val Asp Gly Val Glu Val His
            420                 425                 430 aat gcc aag aca aag ccg cgg gag gag cag tac aac agc acg tac cgt       1344
Asn Ala Lys Thr Lys Pro Arg Glu Glu Gln Tyr Asn Ser Thr Tyr Arg
        435                 440                 445 gtg gtc agc gtc ctc acc gtc ctg cac cag gac tgg ctg aat ggc aag       1392
Val Val Ser Val Leu Thr Val Leu His Gln Asp Trp Leu Asn Gly Lys
    450                 455                 460 gag tac aag tgc aag gtc tcc aac aaa gcc ctc cca gcc ccc atc gag       1440
Glu Tyr Lys Cys Lys Val Ser Asn Lys Ala Leu Pro Ala Pro Ile Glu
465                 470                 475                 480 aaa acc atc tcc aaa gcc aaa ggg cag ccc cga gaa cca cag gtg tac       1488
Lys Thr Ile Ser Lys Ala Lys Gly Gln Pro Arg Glu Pro Gln Val Tyr
                485                 490                 495
```

```
acc ctg ccc cca tcc cgg gat gag ctg acc aag aac cag gtc agc ctg      1536
Thr Leu Pro Pro Ser Arg Asp Glu Leu Thr Lys Asn Gln Val Ser Leu
        500                 505                 510 acc tgc ctg gtc aaa ggc ttc tat ccc agc gac atc gcc gtg gag tgg      1584
Thr Cys Leu Val Lys Gly Phe Tyr Pro Ser Asp Ile Ala Val Glu Trp
        515                 520                 525 gag agc aat ggg cag ccg gag aac aac tac aag acc acg cct ccc gtg      1632
Glu Ser Asn Gly Gln Pro Glu Asn Asn Tyr Lys Thr Thr Pro Pro Val
530                 535                 540 ctg gac tcc gac ggc tcc ttc ttc ctc tac agc aag ctc acc gtg gac      1680
Leu Asp Ser Asp Gly Ser Phe Phe Leu Tyr Ser Lys Leu Thr Val Asp
545                 550                 555                 560 aag agc agg tgg cag cag ggg aac gtc ttc tca tgc tcc gtg atg cat      1728
Lys Ser Arg Trp Gln Gln Gly Asn Val Phe Ser Cys Ser Val Met His
            565                 570                 575 gag gct ctg cac aac cac tac acg cag aag agc ctc tcc ctg tct ccg      1776
Glu Ala Leu His Asn His Tyr Thr Gln Lys Ser Leu Ser Leu Ser Pro
        580                 585                 590 ggt aaa tgataa                                                        1788
Gly Lys <210> SEQ ID NO 22
<211> LENGTH: 594
<212> TYPE: PRT
<213> ORGANISM: Artificial Sequence
<220> FEATURE:
<223> OTHER INFORMATION: Description of Artificial Sequence: murine
      FGFR-L extracellular domain-Fc fusion polypeptide

<400> SEQUENCE: 22

Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Pro Leu Thr Met Trp Thr Lys Asp Gly Arg
     50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Ala Arg Pro Arg
        130                 135                 140

Phe Thr Gln Pro Ser Lys Met Arg Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
        195                 200                 205

Pro Glu Asp Ser Gly Lys Tyr Thr Cys Arg Val Ser Asn Lys Ala Gly
    210                 215                 220
```

-continued

```
Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
            260                 265                 270

Val Ile Gln Trp Leu Lys Arg Val Glu Tyr Gly Ser Glu Gly Arg His
        275                 280                 285

Asn Ser Thr Ile Asp Val Gly Gly Gln Lys Phe Val Val Leu Pro Thr
    290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
                340                 345                 350

Pro Asp Pro Lys Pro Pro Gly Pro Pro Met Ala Ser Ser Ser Val Asp
                355                 360                 365

Lys Thr His Thr Cys Pro Pro Cys Pro Ala Pro Glu Leu Leu Gly Gly
    370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Asn Trp Tyr Val Asp Gly Val Glu Val His
                420                 425                 430

Asn Ala Lys Thr Lys Pro Arg Glu Glu Gln Tyr Asn Ser Thr Tyr Arg
            435                 440                 445

Val Val Ser Val Leu Thr Val Leu His Gln Asp Trp Leu Asn Gly Lys
        450                 455                 460

Glu Tyr Lys Cys Lys Val Ser Asn Lys Ala Leu Pro Ala Pro Ile Glu
465                 470                 475                 480

Lys Thr Ile Ser Lys Ala Lys Gly Gln Pro Arg Glu Pro Gln Val Tyr
                485                 490                 495

Thr Leu Pro Pro Ser Arg Asp Glu Leu Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Asn Gly Gln Pro Glu Asn Asn Tyr Lys Thr Thr Pro Pro Val
530                 535                 540

Leu Asp Ser Asp Gly Ser Phe Phe Leu Tyr Ser Lys Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly Lys
```

US 7,348,162 B2

NUCLEIC ACIDS ENCODING FIBROBLAST GROWTH FACTOR RECEPTOR-LIKE PROTEINS AND USES THEREOF

This application is a continuation of U.S. Provisional Patent Application No. 60/191,379, filed on Mar. 22, 2000, the disclosure of which is explicitly incorporated by reference herein.

FIELD OF THE INVENTION

The present invention relates to Fibroblast Growth Factor Receptor-Like (FGFR-L) polypeptides and nucleic acid molecules encoding the same. The invention also relates to selective binding agents, vectors, host cells, and methods for producing FGFR-L polypeptides. The invention further relates to pharmaceutical compositions and methods for the diagnosis, treatment, amelioration, and/or prevention of diseases, disorders, and conditions associated with FGFR-L polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

SUMMARY OF THE INVENTION

The present invention relates to novel FGFR-L nucleic acid molecules and encoded polypeptides.

The invention provides for an isolated nucleic acid molecule comprising a nucleotide sequence selected from the group consisting of:

(a) the nucleotide sequence as set forth in either SEQ ID NO: 1 or SEQ ID NO: 4;

(b) the nucleotide sequence of the DNA insert in ATCC Deposit No. PTA-1062;

(c) a nucleotide sequence encoding the polypeptide as set forth in either SEQ ID NO: 2 or SEQ ID NO: 5;

(d) a nucleotide sequence which hybridizes under moderately or highly stringent conditions to the complement of any of (a)-(c); and (e) a nucleotide sequence complementary to any of (a)-(c).

The invention also provides for an isolated nucleic acid molecule comprising a nucleotide sequence selected from the group consisting of:

(a) a nucleotide sequence encoding a polypeptide which is at least about 70 percent identical to the polypeptide as set forth in either SEQ ID NO: 2 or SEQ ID NO: 5, wherein the encoded polypeptide has an activity of the polypeptide set forth in either SEQ ID NO: 2 or SEQ ID NO: 5;

(b) a nucleotide sequence encoding an allelic variant or splice variant of the nucleotide sequence as set forth in either SEQ ID NO: 1 or SEQ ID NO: 4, the nucleotide sequence of the DNA insert in ATCC Deposit No. PTA-1062, or (a);

(c) a region of the nucleotide sequence of either SEQ ID NO: 1 or SEQ ID NO: 4, the DNA insert in ATCC Deposit No. PTA-1062, (a), or (b) encoding a polypeptide fragment of at least about 25 amino acid residues, wherein the polypeptide fragment has an activity of the polypeptide set forth in either SEQ ID NO: 2 or SEQ ID NO: 5, or is antigenic;

(d) a region of the nucleotide sequence of either SEQ ID NO: 1 or SEQ ID NO: 4, the DNA insert in ATCC Deposit No. PTA-1062, or any of (a)-(c) comprising a fragment of at least about 16 nucleotides;

(e) a nucleotide sequence which hybridizes under moderately or highly stringent conditions to the complement of any of (a)-(d); and (f) a nucleotide sequence complementary to any of (a)-(d).

The invention further provides for an isolated nucleic acid molecule comprising a nucleotide sequence selected from the group consisting of:

(a) a nucleotide sequence encoding a polypeptide as set forth in either SEQ ID NO: 2 or SEQ ID NO: 5 with at least one conservative amino acid substitution, wherein the encoded polypeptide has an activity of the polypeptide set forth in either SEQ ID NO: 2 or SEQ ID NO: 5;

(b) a nucleotide sequence encoding a polypeptide as set forth in either SEQ ID NO: 2 or SEQ ID NO: 5 with at least one amino acid insertion, wherein the encoded polypeptide has an activity of the polypeptide set forth in either SEQ ID NO: 2 or SEQ ID NO: 5;

(c) a nucleotide sequence encoding a polypeptide as set forth in either SEQ ID NO: 2 or SEQ ID NO: 5 with at least one amino acid deletion, wherein the encoded polypeptide has an activity of the polypeptide set forth in either SEQ ID NO: 2 or SEQ ID NO: 5;

(d) a nucleotide sequence encoding a polypeptide as set forth in either SEQ ID NO: 2 or SEQ ID NO: 5 which has a C- and/or N-terminal truncation, wherein the encoded polypeptide has an activity of the polypeptide set forth in either SEQ ID NO: 2 or SEQ ID NO: 5;

(e) a nucleotide sequence encoding a polypeptide as set forth in either SEQ ID NO: 2 or SEQ ID NO: 5 with at least one modification selected from the group consisting of amino acid substitutions, amino acid insertions, amino acid deletions, C-terminal truncation, and N-terminal truncation, wherein the encoded polypeptide has an activity of the polypeptide set forth in either SEQ ID NO: 2 or SEQ ID NO: 5;

(f) a nucleotide sequence of any of (a)-(e) comprising a fragment of at least about 16 nucleotides;

(g) a nucleotide sequence which hybridizes under moderately or highly stringent conditions to the complement of any of (a)-(f); and (h) a nucleotide sequence complementary to any of (a)-(e).

The present invention provides for an isolated polypeptide comprising an amino acid sequence selected from the group consisting of:

(a) the amino acid sequence as set forth in either SEQ ID NO: 2 or SEQ ID NO: 5; and (b) the amino acid sequence encoded by the DNA insert in ATCC Deposit No. PTA-1062.

The invention also provides for an isolated polypeptide comprising the amino acid sequence selected from the group consisting of (a) the amino acid sequence as set forth in SEQ ID NO: 3 or SEQ ID NO: 6, optionally further comprising an amino-terminal methionine;

(b) an amino acid sequence for an ortholog of either SEQ ID NO: 2 or SEQ ID NO: 5;

(c) an amino acid sequence which is at least about 70 percent identical to the amino acid sequence of either SEQ ID NO: 2 or SEQ ID NO: 5, wherein the polypeptide has an activity of the polypeptide set forth in either SEQ ID NO: 2 or SEQ ID NO: 5;

(d) a fragment of the amino acid sequence set forth in either SEQ ID NO: 2 or SEQ ID NO: 5 comprising at least about 25 amino acid residues, wherein the fragment has an activity of the polypeptide set forth in either SEQ ID NO: 2 or SEQ ID NO: 5, or is antigenic; and (e) an amino acid sequence for an allelic variant or splice variant of the amino acid sequence as set forth in either SEQ ID NO: 2 or SEQ ID NO: 5, the amino acid sequence encoded by the DNA insert in ATCC Deposit No. PTA-1062, or any of (a)-(c).

The invention further provides for an isolated polypeptide comprising the amino acid sequence selected from the group consisting of:

(a) the amino acid sequence as set forth in either SEQ ID NO: 2 or SEQ ID NO: 5 with at least one conservative amino acid substitution, wherein the polypeptide has an activity of the polypeptide set forth in either SEQ ID NO: 2 or SEQ ID NO: 5;

(b) the amino acid sequence as set forth in either SEQ ID NO: 2 or SEQ ID NO: 5 with at least one amino acid insertion, wherein the polypeptide has an activity of the polypeptide set forth in either SEQ ID NO: 2 or SEQ ID NO: 5;

(c) the amino acid sequence as set forth in either SEQ ID NO: 2 or SEQ ID NO: 5 with at least one amino acid deletion, wherein the polypeptide has an activity of the polypeptide set forth in either SEQ ID NO: 2 or SEQ ID NO: 5;

(d) the amino acid sequence as set forth in either SEQ ID NO: 2 or SEQ ID NO: 5 which has a C- and/or N-terminal truncation, wherein the polypeptide has an activity of the polypeptide set forth in either SEQ ID NO: 2 or SEQ ID NO: 5; and (e) the amino acid sequence as set forth in either SEQ ID NO: 2 or SEQ ID NO: 5 with at least one modification selected from the group consisting of amino acid substitutions, amino acid insertions, amino acid deletions, C-terminal truncation, and N-terminal truncation, wherein the polypeptide has an activity of the polypeptide set forth in either SEQ ID NO: 2 or SEQ ID NO: 5.

Also provided are fusion polypeptides comprising FGFR-L amino acid sequences.

The present invention also provides for an expression vector comprising the isolated nucleic acid molecules as set forth herein, recombinant host cells comprising the recombinant nucleic acid molecules as set forth herein, and a method of producing an FGFR-L polypeptide comprising culturing the host cells and optionally isolating the polypeptide so produced.

A transgenic non-human animal comprising a nucleic acid molecule encoding an FGFR-L polypeptide is also encompassed by the invention. The FGFR-L nucleic acid molecules are introduced into the animal in a manner that allows expression and increased levels of an FGFR-L polypeptide, which may include increased circulating levels. Alternatively, the FGFR-L nucleic acid molecules are introduced into the animal in a manner that prevents expression of endogenous FGFR-L polypeptide (i.e., generates a transgenic animal possessing an FGFR-L polypeptide gene knockout). The transgenic non-human animal is preferably a mammal, and more preferably a rodent, such as a rat or a mouse.

Also provided are derivatives of the FGFR-L polypeptides of the present invention.

Additionally provided are selective binding agents such as antibodies and peptides capable of specifically binding the FGFR-L polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The FGFR-L polypeptides and nucleic acid molecules of the present invention may be used to treat, prevent, ameliorate, and/or detect diseases and disorders, including those recited herein.

The present invention also provides a method of assaying test molecules to identify a test molecule that binds to an FGFR-L polypeptide. The method comprises contacting an FGFR-L polypeptide with a test molecule to determine the extent of binding of the test molecule to the polypeptide. The method further comprises determining whether such test molecules are agonists or antagonists of an FGFR-L polypeptide. The present invention further provides a method of testing the impact of molecules on the expression of FGFR-L polypeptide or on the activity of FGFR-L polypeptide.

Methods of regulating expression and modulating (i.e., increasing or decreasing) levels of an FGFR-L polypeptide are also encompassed by the invention. One method comprises administering to an animal a nucleic acid molecule encoding an FGFR-L polypeptide. In another method, a nucleic acid molecule comprising elements that regulate or modulate the expression of an FGFR-L polypeptide may be administered. Examples of these methods include gene therapy, cell therapy, and anti-sense therapy as further described herein.

The FGFR-L polypeptide can be used for identifying ligands thereof. Various forms of "expression cloning" have been used for cloning ligands for receptors (e.g., Davis et al., 1996, Cell, 87:1161-69). These and other FGFR-L polypeptide ligand cloning experiments are described in greater detail herein. Isolation of an FGFR-L polypeptide ligand allows for the identification or development of novel agonists or antagonists of the FGFR-L polypeptide signaling pathway. Such agonists and antagonists include FGFR-L polypeptide ligands, anti-FGFR-L polypeptide ligand antibodies and derivatives thereof, small molecules, or antisense oligonucleotides, any of which can be used for potentially treating one or more diseases or disorders, including those recited herein.

BRIEF DESCRIPTION OF THE FIGURES

FIGS. 1A-1C illustrate the nucleotide sequence of the murine FGFR-L gene (SEQ ID NO: 1) and the deduced amino acid sequence of murine FGFR-L polypeptide (SEQ ID NO: 2). The predicted signal peptide (underline) and transmembrane domain (double-underline) are indicated;

FIGS. 2A-2C illustrate nucleotide sequence of a cDNA clone encoding the N-terminal portion of the human FGFR-L gene (SEQ ID NO: 4) and the deduced amino acid sequence of the N-terminal portion of the human FGFR-L polypeptide (SEQ ID NO: 5). The predicted signal peptide (underline) and transmembrane domain (double-underline) are indicated;

FIGS. 3A-3B illustrate the amino acid sequence alignment of murine FGFR-L polypeptide (Smaf2-00017-f4; SEQ ID NO: 2) and Iberian ribbed newt (*Pleurodeles waltlii*) Fibroblast Growth Factor Receptor-4 (PJR:B49151: SEQ ID NO: 7);

FIG. 4 illustrates the amino acid sequence alignment of murine FGFR-L polypeptide (SEQ ID NO: 2) and a virtual human FGFR-L polypeptide sequence (SEQ ID NO: 8) constructed from residues 1-472 of SEQ ID NO: 5 and residues 473-504 of GenBank Accession No. AJ277437. The predicted signal peptide (underline), transmembrane domain (double-underline), and N-linked glycosylation sites (bold) are indicated;

FIG. 18 illustrates the results of Western blot analysis of *E. coli*-derived Des7-FGFR-L/ECD and CHO-derived FGFR-L/ECD-Fc proteins using FGFR-L polypeptide antiserum;

DETAILED DESCRIPTION OF THE INVENTION

Figure 5:
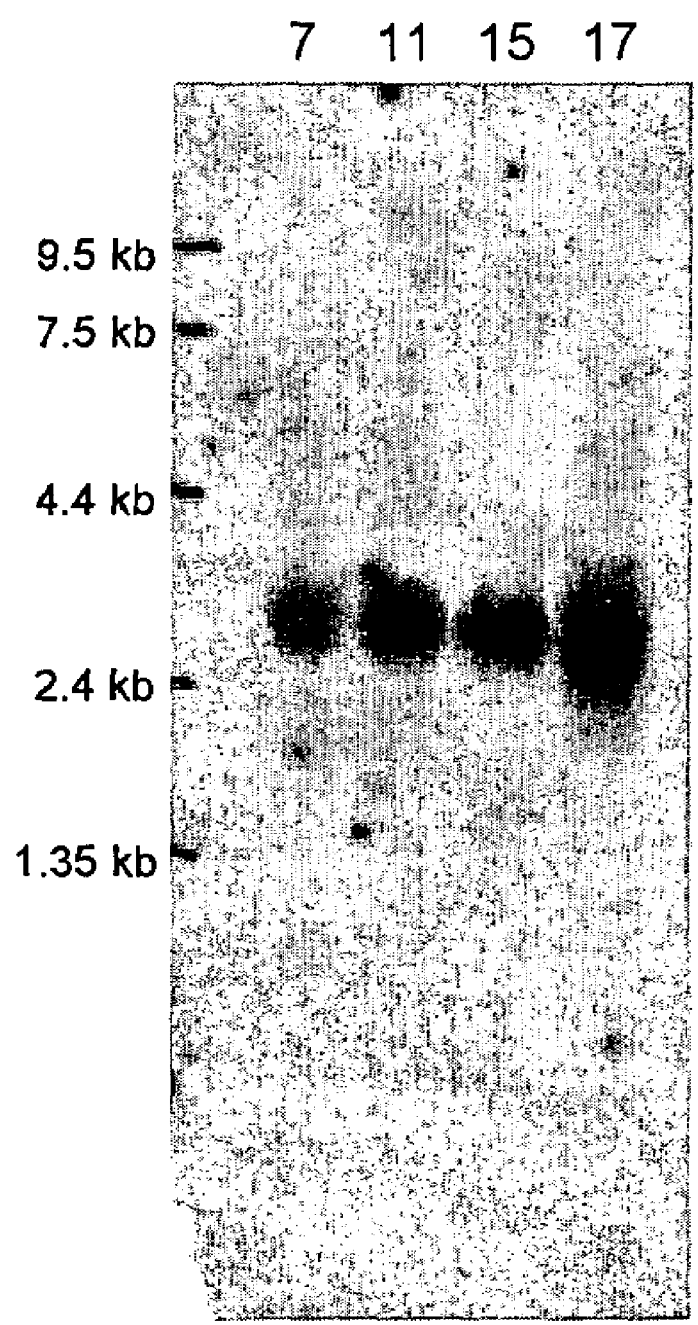
FIG. 5 illustrates the expression of FGFR-L mRNA as detected by Northern blot analysis in day 7, 11, 15, and 17 mouse embryos.

The section headings used herein are for organizational purposes only and are not to be construed as limiting the subject matter described. All references cited in this application are expressly incorporated by reference herein.

Definitions

The terms "FGFR-L gene" or "FGFR-L nucleic acid molecule" or "FGFR-L polynucleotide" refer to a nucleic acid molecule comprising or consisting of a nucleotide sequence as set forth in either SEQ ID NO: 1 or SEQ ID NO: 4, a nucleotide sequence encoding the polypeptide as set forth in either SEQ ID NO: 2 or SEQ ID NO: 5, a nucleotide sequence of the DNA insert in ATCC Deposit No. PTA-1062, and nucleic acid molecules as defined herein.

The term "FGFR-L polypeptide allelic variant" refers to one of several possible naturally occurring alternate forms of a gene occupying a given locus on a chromosome of an organism or a population of organisms.

The term "FGFR-L polypeptide splice variant" refers to a nucleic acid molecule, usually RNA, which is generated by alternative processing of intron sequences in an RNA transcript of FGFR-L polypeptide amino acid sequence as set forth in either SEQ ID NO: 2 or SEQ ID NO: 5.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "FGFR-L polypeptide" refers to a polypeptide comprising the amino acid sequence of either SEQ ID NO: 2 or SEQ ID NO: 5 and related polypeptides. Related polypeptides include FGFR-L polypeptide fragments, FGFR-L polypeptide orthologs, FGFR-L polypeptide variants, and FGFR-L polypeptide derivatives, which possess at least one activity of the polypeptide as set forth in either SEQ ID NO: 2 or SEQ ID NO: 5. FGFR-L polypeptides may be mature polypeptides, as defined herein, and may or may not have an amino-terminal methionine residue, depending on the method by which they are prepared.

The term "FGFR-L polypeptide fragment" refers to a polypeptide that comprises a truncation at the amino-terminus (with or without a leader sequence) and/or a truncation at the carboxyl-terminus of the polypeptide as set forth in either SEQ ID NO: 2 or SEQ ID NO: 5. The term "FGFR-L polypeptide fragment" also refers to amino-terminal and/or carboxyl-terminal truncations of FGFR-L polypeptide orthologs, FGFR-L polypeptide derivatives, or FGFR-L polypeptide variants, or to amino-terminal and/or carboxyl-terminal truncations of the polypeptides encoded by FGFR-L polypeptide allelic variants or FGFR-L polypeptide splice variants. FGFR-L polypeptide fragments may result from alternative RNA splicing or from in vivo protease activity. Membrane-bound forms of an FGFR-L polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids, or more than about 200 amino acids. Such FGFR-L polypeptide fragments may optionally comprise an amino-terminal methionine residue. It will be appreciated that such fragments can be used, for example, to generate antibodies to FGFR-L polypeptides.

The term "FGFR-L polypeptide ortholog" refers to a polypeptide from another species that corresponds to FGFR-L polypeptide amino acid sequence as set forth in either SEQ ID NO: 2 or SEQ ID NO: 5. For example, mouse and human FGFR-L polypeptides are considered orthologs of each other.

The term "FGFR-L polypeptide variants" refers to FGFR-L polypeptides comprising amino acid sequences having one or more amino acid sequence substitutions, deletions (such as internal deletions and/or FGFR-L polypeptide fragments), and/or additions (such as internal additions and/or FGFR-L fusion polypeptides) as compared to the FGFR-L polypeptide amino acid sequence set forth in either SEQ ID NO: 2 or SEQ ID NO: 5 (with or without a leader sequence). Variants may be naturally occurring (e.g., FGFR-L polypeptide allelic variants, FGFR-L polypeptide orthologs, and FGFR-L polypeptide splice variants) or artificially constructed. Such FGFR-L polypeptide variants may be prepared from the corresponding nucleic acid molecules having a DNA sequence that varies accordingly from the DNA sequence as set forth in either SEQ ID NO: 1 or SEQ ID NO: 4. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "FGFR-L polypeptide derivatives" refers to the polypeptide as set forth in either SEQ ID NO: 2 or SEQ ID NO: 5, FGFR-L polypeptide fragments, FGFR-L polypeptide orthologs, or FGFR-L polypeptide variants, as defined herein, that have been chemically modified. The term "FGFR-L polypeptide derivatives" also refers to the polypeptides encoded by FGFR-L polypeptide allelic variants or FGFR-L polypeptide splice variants, as defined herein, that have been chemically modified.

The term "mature FGFR-L polypeptide" refers to an FGFR-L polypeptide lacking a leader sequence. A mature FGFR-L polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like. An exemplary mature FGFR-L polypeptide is depicted by the amino acid sequence of either SEQ ID NO: 3 or SEQ ID NO: 6.

The term "FGFR-L fusion polypeptide" refers to a fusion of one or more amino acids (such as a heterologous protein or peptide) at the amino- or carboxyl-terminus of the polypeptide as set forth in either SEQ ID NO: 2 or SEQ ID NO: 5, FGFR-L polypeptide fragments, FGFR-L polypeptide orthologs, FGFR-L polypeptide variants, or FGFR-L derivatives, as defined herein. The term "FGFR-L fusion polypeptide" also refers to a fusion of one or more amino acids at the amino- or carboxyl-terminus of the polypeptide encoded by FGFR-L polypeptide allelic variants or FGFR-L polypeptide splice variants, as defined herein.

The term "biologically active FGFR-L polypeptides" refers to FGFR-L polypeptides having at least one activity characteristic of the polypeptide comprising the amino acid sequence of either SEQ ID NO: 2 or SEQ ID NO: 5. In addition, an FGFR-L polypeptide may be active as an immunogen; that is, the FGFR-L polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of an FGFR-L polypeptide or FGFR-L nucleic acid molecule used to support an observable level of one or more biological activities of the FGFR-L polypeptides as set forth herein.

The term "pharmaceutically acceptable carrier" or "physiologically acceptable carrier" as used herein refers to one or more formulation materials suitable for accomplishing or enhancing the delivery of the FGFR-L polypeptide, FGFR-L nucleic acid molecule, or FGFR-L selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for an FGFR-L polypeptide. As used herein, the terms, "specific" and "specificity" refer to the ability of the selective binding agents to bind to human FGFR-L polypeptides and not to bind to human non-FGFR-L polypeptides. It will be appreciated, however, that the selective binding agents may also bind orthologs of the polypeptide as set forth in either SEQ ID NO: 2 or SEQ ID NO: 5, that is, interspecies versions thereof, such as mouse and rat FGFR-L polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al, *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of either SEQ ID NO: 1 or SEQ ID NO: 4, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in either SEQ ID NO: 2 or SEQ ID NO: 5. Such related FGFR-L polypeptides may comprise, for example, an addition and/or a deletion of one or more N-linked or O-linked glycosylation sites or an addition and/or a deletion of one or more cysteine residues.

Related nucleic acid molecules also include fragments of FGFR-L nucleic acid molecules which encode a polypeptide of at least about 25 contiguous amino acids, or about 50 amino acids, or about 75 amino acids, or about 100 amino acids, or about 150 amino acids, or about 200 amino acids, or more than about 200 amino acid residues of the FGFR-L polypeptide of either SEQ ID NO: 2 or SEQ ID NO: 5.

In addition, related FGFR-L nucleic acid molecules also include those molecules which comprise nucleotide sequences which hybridize under moderately or highly stringent conditions as defined herein with the fully complementary sequence of the FGFR-L nucleic acid molecule of either SEQ ID NO: 1 or SEQ ID NO: 4, or of a molecule encoding a polypeptide, which polypeptide comprises the amino acid sequence as shown in either SEQ ID NO: 2 or SEQ ID NO: 5, or of a nucleic acid fragment as defined herein, or of a nucleic acid fragment encoding a polypeptide as defined herein. Hybridization probes may be prepared using the FGFR-L sequences provided herein to screen cDNA, genomic or synthetic DNA libraries for related sequences. Regions of the DNA and/or amino acid sequence of FGFR-L polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementaiy, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log[Na+])+0.41(\% \ G+C)-600/N-0.72(\% \ \text{formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$Tm=2°$ C. per A-T base pair+4° C. per G-C base pair

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in either SEQ ID NO: 1 or SEQ ID NO: 4, or comprise or consist essentially of a nucleotide sequence encoding a polypeptide that is at least about 70 percent identical to the polypeptide as set forth in either SEQ ID NO: 2 or SEQ ID NO: 5. In preferred embodiments, the nucleotide sequences are about 75 percent, or about 80 percent, or about 85 percent, or about 90 percent, or about 95, 96, 97, 98, or 99 percent identical to the nucleotide sequence as shown in either SEQ ID NO: 1 or SEQ ID NO: 4, or the nucleotide sequences encode a polypeptide that is about 75 percent, or about 80 percent, or about 85 percent, or about 90 percent, or about 95, 96, 97, 98, or 99 percent identical to the polypeptide sequence as set forth in either SEQ ID NO: 2 or SEQ ID NO: 5. Related nucleic acid molecules encode polypeptides possessing at least one activity of the polypeptide set forth in either SEQ ID NO: 2 or SEQ ID NO: 5.

Differences in the nucleic acid sequence may result in conservative and/or non-conservative modifications of the amino acid sequence relative to the amino acid sequence of either SEQ ID NO: 2 or SEQ ID NO: 5.

Conservative modifications to the amino acid sequence of either SEQ ID NO: 2 or SEQ ID NO: 5 (and the corresponding modifications to the encoding nucleotides) will produce a polypeptide having functional and chemical characteristics similar to those of FGFR-L polypeptides. In contrast, substantial modifications in the functional and/or chemical characteristics of FGFR-L polypeptides may be accomplished by selecting substitutions in the amino acid sequence of either SEQ ID NO: 2 or SEQ ID NO: 5 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human FGFR-L polypeptide that are homologous with non-human FGFR-L polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the FGFR-L polypeptide, or to increase or decrease the affinity of the FGFR-L polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in either SEQ ID NO: 2 or SEQ ID NO: 5 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of an FGFR-L polypeptide to such similar polypeptides. With such a comparison, one can identify residues and portions of the molecules that are conserved among similar polypeptides. It will be appreciated that changes in areas of the FGFR-L molecule that are not conserved relative to such similar polypeptides would be less likely to adversely affect the biological activity and/or structure of an FGFR-L polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an FGFR-L polypeptide that correspond to amino acid residues that are important for activity or structure in similar polypeptides. One skilled in the art may opt for chemically similar amino acid substitutions for such predicted important amino acid residues of FGFR-L polypeptides.

One skilled in the art can also analyze the three-dimensional structure and amino acid sequence in relation to that structure in similar polypeptides. In view of such information, one skilled in the art may predict the alignment of amino acid residues of FGFR-L polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al, 1979, *Biophys. J.* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred FGFR-L polypeptide variants include glycosylation variants wherein the number and/or type of glycosylation sites have been altered compared to the amino acid sequence set forth in either SEQ ID NO: 2 or SEQ ID NO: 5. In one embodiment, FGFR-L polypeptide variants comprise a greater or a lesser number of N-linked glycosylation sites than the amino acid sequence set forth in either SEQ ID NO: 2 or SEQ ID NO: 5. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred FGFR-L variants include cysteine variants, wherein one or more cysteine residues are deleted or substituted with another amino acid (e.g., serine) as compared to the amino acid sequence set forth in either SEQ ID NO: 2 or SEQ ID NO: 5. Cysteine variants are useful when FGFR-L polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in either SEQ ID NO: 2 or SEQ ID NO: 5 with at least one amino acid insertion and wherein the polypeptide has an activity of the polypeptide set forth in either SEQ ID NO: 2 or SEQ ID NO: 5, or a nucleotide sequence encoding a polypeptide as set forth in either SEQ ID NO: 2 or SEQ ID NO: 5 with at least one amino acid deletion and wherein the polypeptide has an activity of the polypeptide set forth in either SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 wherein the polypeptide has a carboxyl- and/or amino-terminal truncation and further wherein the polypeptide has an activity of the polypeptide set forth in either SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 with at least one modification selected from the group consisting of amino acid substitutions, amino acid insertions, amino acid deletions, carboxyl-terminal truncations, and amino-terminal truncations and wherein the polypeptide has an activity of the polypeptide set forth in either SEQ ID NO: 2 or SEQ ID NO: 5.

In addition, the polypeptide comprising the amino acid sequence of either SEQ ID NO: 2 or SEQ ID NO: 5, or other FGFR-L polypeptide, may be fused to a homologous polypeptide to form a homodimer or to a heterologous polypeptide to form a heterodimer. Heterologous peptides and polypeptides include, but are not limited to: an epitope to allow for the detection and/or isolation of an FGFR-L fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in either SEQ ID NO: 2 or SEQ ID NO: 5, or other FGFR-L polypeptide.

Fusions can be made either at the amino-terminus or at the carboxyl-terminus of the polypeptide comprising the amino acid sequence set forth in either SEQ ID NO: 2 or SEQ ID NO: 5, or other FGFR-L polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of either SEQ ID NO: 2 or SEQ ID NO: 5, or other FGFR-L polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, Nature 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
| --- | --- | --- | --- |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154:5590-600 |
| IgG1 | TNF receptor | septic shock | Fisher et al., 1996, N. Engl. J. Med. 334:1697-1702; Van Zee et al., 1996, J. Immunol. 156:2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337:525-31 |
| IgG1, IgG3 | N-terminus of IL-2 | anti-cancer, antiviral | Harvill et al., 1995, Immunotech. 1:95-105 |
| IgG1 | C-terminus of OPG | osteoarthritis; bone density | WO 97/23614 |

TABLE II-continued

Fc Fusion with Therapeutic Proteins

| Form of Fc | Fusion partner | Therapeutic implications | Reference |
|---|---|---|---|
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174:561-69 |

In one example, a human IgG hinge, CH2, and CH3 region may be fused at either the amino-terminus or carboxyl-terminus of the FGFR-L polypeptides using methods known to the skilled artisan. In another example, a human IgG hinge, CH2, and CH3 region may be fused at either the amino-terminus or carboxyl-terminus of an FGFR-L polypeptide fragment (e.g., the predicted extracellular portion of FGFR-L polypeptide).

The resulting FGFR-L fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/ multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;

Comparison matrix: BLOSUM 62 (Henikoff et al, supra);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, supra;

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of an FGFR-L polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of an FGFR-L polypeptide has been identified from one species, all or a portion of that gene may be used as a probe to identify orthologs or related genes from the same species. The probes or primers may be used to screen cDNA libraries from various tissue sources believed to express the FGFR-L polypeptide. In addition, part or all of a nucleic acid molecule having the sequence as set forth in either SEQ ID NO: 1 or SEQ ID NO: 4 may be used to screen a genomic library to identify and isolate a gene encoding the amino acid sequence of an FGFR-L polypeptide. Typically, conditions of moderate or high stringency will be employed for screening to minimize the number of false positives obtained from the screening.

Nucleic acid molecules encoding the amino acid sequence of FGFR-L polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of an FGFR-L polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an FGFR-L polypeptide can be inserted into an expression vector. By introducing the expression vector into an appropriate host, the encoded FGFR-L polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of an FGFR-L polypeptide, are then added to the cDNA along with a polymerase such as Taq polymerase, and the polymerase amplifies the cDNA region between the two primers.

Another means of preparing a nucleic acid molecule encoding the amino acid sequence of an FGFR-L polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of an FGFR-L polypeptide will be several hundred nucleotides in length. Nucleic acids larger than about 100 nucleotides can be synthesized as several fragments using these methods. The fragments can then be ligated together to form the full-length nucleotide sequence of an FGFR-L gene. Usually, the DNA fragment encoding the amino-terminus of the polypeptide will have an ATG, which encodes a methionine residue. This methionine may or may not be present on the mature form of the FGFR-L polypeptide, depending on whether the polypeptide produced in the host cell is designed to be secreted from that cell. Other methods known to the skilled artisan may be used as well.

In certain embodiments, nucleic acid variants contain codons which have been altered for optimal expression of an FGFR-L polypeptide in a given host cell. Particular codon alterations will depend upon the FGFR-L polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

In some cases, it may be desirable to prepare nucleic acid molecules encoding FGFR-L polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of an FGFR-L polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an FGFR-L polypeptide may be amplified/expressed in prokaryotic, yeast, insect (baculovirus systems) and/or eukaryotic host cells. Selection of the host cell will depend in part on whether an FGFR-L polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the FGFR-L polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the FGFR-L polypeptide from the host cell. Affinity purification can be accomplished, for example, by column chromatography using antibodies against the tag as an affinity matrix. Optionally, the tag can subsequently be removed from the purified FGFR-L polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate FGFR-L polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the FGFR-L gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an FGFR-L polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an FGFR-L polypeptide. As a result, increased quantities of FGFR-L polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of an FGFR-L polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct an FGFR-L polypeptide out of the host cell. Typically, a nucleotide sequence encoding the signal sequence is positioned in the coding region of an FGFR-L nucleic acid molecule, or directly at the 5' end of an FGFR-L polypeptide coding region. Many signal sequences have been identified, and any of those that are functional in the selected host cell may be used in conjunction with an FGFR-L nucleic acid molecule.

Therefore, a signal sequence may be homologous (naturally occurring) or heterologous to the FGFR-L nucleic acid molecule. Additionally, a signal sequence may be chemically synthesized using methods described herein. In most cases, the secretion of an FGFR-L polypeptide from the host cell via the presence of a signal peptide will result in the removal of the signal peptide from the secreted FGFR-L polypeptide. The signal sequence may be a component of the vector, or it may be a part of an FGFR-L nucleic acid molecule that is inserted into the vector.

Included within the scope of this invention is the use of either a nucleotide sequence encoding a native FGFR-L polypeptide signal sequence joined to an FGFR-L polypeptide coding region or a nucleotide sequence encoding a heterologous signal sequence joined to an FGFR-L polypeptide coding region. The heterologous signal sequence selected should be one that is recognized and processed, i.e., cleaved by a signal peptidase, by the host cell. For prokaryotic host cells that do not recognize and process the native FGFR-L polypeptide signal sequence, the signal sequence is substituted by a prokaryotic signal sequence selected, for example, from the group of the alkaline phosphatase, penicillinase, or heat-stable enterotoxin II leaders. For yeast secretion, the native FGFR-L polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired FGFR-L polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the FGFR-L gene especially where the gene used is a full-length genomic sequence or a fragment thereof. Where the intron is not naturally occurring within the gene (as for most cDNAs), the intron may be obtained from another source. The position of the intron with respect to flanking sequences and the FGFR-L gene is generally important, as the intron must be transcribed to be effective. Thus, when an FGFR-L cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the FGFR-L polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding FGFR-L polypeptide by removing the promoter from the source DNA by restriction enzyme digestion and inserting the desired promoter sequence into the vector. The native FGFR-L promoter sequence may be used to direct amplification and/or expression of an FGFR-L nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling FGFR-L gene expression include, but are not limited to: the SV40 early promoter region (Bemoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al, 1982, *Nature* 296: 39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Omitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.,* 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding an FGFR-L polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an FGFR-L nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding an FGFR-L polypeptide has been inserted into the proper site of the vector, the completed vector may be inserted into a suitable host cell for amplification and/or polypeptide expression. The transformation of an expression vector for an FGFR-L polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes an FGFR-L polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(-) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris.*

Additionally, where desired, insect cell systems may be utilized in the methods of the present invention. Such systems are described, for example, in Kitts et al., 1993,

*Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated FGFR-L polypeptides. For example, one may use a transgenic milk-producing animal (a cow or goat, for example) and obtain the present glycosylated polypeptide in the animal milk. One may also use plants to produce FGFR-L polypeptides, however, in general, the glycosylation occurring in plants is different from that produced in mammalian cells, and may result in a glycosylated product which is not suitable for human therapeutic use.

Polypeptide Production

Host cells comprising an FGFR-L polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of an FGFR-L polypeptide produced by a host cell can be evaluated using standard methods known in the art. Such methods include, without limitation, Western blot analysis, SDS-polyacrylamide gel electrophoresis, nondenaturing gel electrophoresis, High Performance Liquid Chromatography (HPLC) separation, immunoprecipitation, and/or activity assays such as DNA binding gel shift assays.

If an FGFR-L polypeptide has been designed to be secreted from the host cells, the majority of polypeptide may be found in the cell culture medium. If however, the FGFR-L polypeptide is not secreted from the host cells, it will be present in the cytoplasm and/or the nucleus (for eukaryotic host cells) or in the cytosol (for gram-negative bacteria host cells).

For an FGFR-L polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an FGFR-L polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized FGFR-L polypeptide can then be analyzed using gel electrophoresis, immunoprecipitation, or the like. If it is desired to isolate the FGFR-L polypeptide, isolation may be accomplished using standard methods such as those described herein and in Marston et al., 1990, *Meth. Enz.*, 182:264-75.

In some cases, an FGFR-L polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b (ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of an FGFR-L polypeptide, then the polypeptide will be found primarily in the supernatant after centrifugation of the cell homogenate. The polypeptide may be further isolated from the supernatant using methods such as those described herein.

The purification of an FGFR-L polypeptide from solution can be accomplished using a variety of techniques. If the polypeptide has been synthesized such that it contains a tag such as Hexahistidine (FGFR-L polypeptide/hexaHis) or other small peptide such as FLAG (Eastman Kodak Co., New Haven, Conn.) or myc (Invitrogen, Carlsbad, Calif.) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiage® nickel columns) can be used for purification of FGFR-L polypeptide/polyHis. See, e.g., *Current Protocols in Molecular Biology* § 10.11.8 (Ausubel et al., eds., Green Publishers Inc. and Wiley and Sons 1993).

Additionally, FGFR-L polypeptides may be purified through the use of a monoclonal antibody that is capable of specifically recognizing and binding to an FGFR-L polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

FGFR-L polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized FGFR-L polypeptides may be oxidized using methods set forth in these references to form disulfide bridges. Chemically synthesized FGFR-L polypeptides are expected to have comparable biological activity to the corresponding FGFR-L polypeptides produced recombinantly or purified from natural sources, and thus may be used interchangeably with a recombinant or natural FGFR-L polypeptide.

Another means of obtaining FGFR-L polypeptide is via purification from biological samples such as source tissues and/or fluids in which the FGFR-L polypeptide is naturally found. Such purification can be conducted using methods for protein purification as described herein. The presence of the FGFR-L polypeptide during purification may be monitored, for example, using an antibody prepared against recombinantly produced FGFR-L polypeptide or peptide fragments thereof.

A number of additional methods for producing nucleic acids and polypeptides are known in the art, and the methods can be used to produce polypeptides having specificity for FGFR-L polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive FGFR-L polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more FGFR-L polypeptides. Suitable selective binding agents include, but are not limited to, antibodies and derivatives thereof, polypeptides, and small molecules. Suitable selective binding agents may be prepared using methods known in the art. An exemplary FGFR-L polypeptide selective binding agent of the present invention is capable of binding a certain portion of the FGFR-L polypeptide thereby inhibiting the binding of the FGFR-L polypeptide to an FGFR-L polypeptide receptor.

Selective binding agents such as antibodies and antibody fragments that bind FGFR-L polypeptides are within the scope of the present invention. The antibodies may be polyclonal including monospecific polyclonal; monoclonal (MAbs); recombinant; chimeric; humanized, such as CDR-grafted; human; single chain; and/or bispecific; as well as fragments; variants; or derivatives thereof. Antibody fragments include those portions of the antibody that bind to an epitope on the FGFR-L polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an FGFR-L polypeptide generally are produced in animals (e.g., rabbits or mice) by means of multiple subcutaneous or intraperitoneal injections of FGFR-L polypeptide and an adjuvant. It may be useful to conjugate an FGFR-L polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-FGFR-L antibody titer.

Monoclonal antibodies directed toward FGFR-L polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with FGFR-L polypeptides.

Monoclonal antibodies of the invention may be modified for use as therapeutics. One embodiment is a "chimeric" antibody in which a portion of the heavy (H) and/or light (L)

chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region (CDR) for the corresponding regions of a human antibody.

Also encompassed by the invention are human antibodies that bind FGFR-L polypeptides. Using transgenic animals (e.g., mice) that are capable of producing a repertoire of human antibodies in the absence of endogenous immunoglobulin production such antibodies are produced by immunization with an FGFR-L polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-FGFR-L antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of FGFR-L polypeptides. The antibodies will bind FGFR-L polypeptides with an affinity that is appropriate for the assay method being employed.

For diagnostic applications, in certain embodiments, anti-FGFR-L antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., an FGFR-L polypeptide, or an immunologically reactive portion thereof) to compete with the test sample analyte (an FGFR-L polypeptide) for binding with a limited amount of anti-FGFR-L antibody. The amount of an FGFR-L polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-FGFR-L antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of an FGFR-L polypeptide. In one embodiment, antagonist antibodies of the invention are antibodies or binding fragments thereof which are capable of specifically binding to an FGFR-L polypeptide and which are capable of inhibiting or eliminating the functional activity of an FGFR-L polypeptide in vivo or in vitro. In preferred embodiments, the selective binding agent, e.g., an antagonist antibody, will inhibit the functional activity of an FGFR-L polypeptide by at least about 50%, and preferably by at least about 80%. In another embodiment, the selective binding agent may be an anti-FGFR-L polypeptide antibody that is capable of interacting with an FGFR-L polypeptide binding partner (a ligand or receptor) thereby inhibiting or eliminating FGFR-L polypeptide activity in vitro or in vivo. Selective binding agents, including agonist and antagonist anti-FGFR-L polypeptide antibodies, are identified by screening assays that are well known in the art.

The invention also relates to a kit comprising FGFR-L selective binding agents (such as antibodies) and other reagents useful for detecting FGFR-L polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the FGFR-L molecules of the invention, including, but not limited to: the identification and validation of FGFR-L disease-related genes as targets for therapeutics; molecular toxicology of related FGFR-L molecules and inhibitors thereof; stratification of populations and generation of surrogate markers for clinical trials; and enhancing related FGFR-L polypeptide small molecule drug discovery by aiding in the identification of selective compounds in high throughput screens.

Chemical Derivatives

Chemically modified derivatives of FGFR-L polypeptides may be prepared by one skilled in the art, given the disclosures described herein. FGFR-L polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of either SEQ ID NO: 2 or SEQ ID NO: 5, or other FGFR-L polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached FGFR-L polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of either SEQ ID NO: 2 or SEQ ID NO: 5, or other FGFR-L polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the FGFR-L polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, FGFR-L polypeptides may be chemically coupled to biotin. The biotin/FGFR-L polypeptide molecules are then allowed to bind to avidin, resulting in tetravalent avidin/biotin/FGFR-L polypeptide molecules. FGFR-L polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present FGFR-L polypeptide derivatives include those described herein for FGFR-L polypeptides. However, the FGFR-L polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native FGFR-L polypeptide have been disrupted (i.e., "knocked out") such that the level of expression of FGFR-L polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of an FGFR-L gene for that animal or a heterologous FGFR-L gene is over-expressed by the animal, thereby creating a "transgenic" animal. Such transgenic animals may be prepared using well known methods such as those described in U.S. Pat. No 5,489,743 and PCT Pub. No. WO 94/28122.

The present invention further includes non-human animals in which the promoter for one or more of the FGFR-L polypeptides of the present invention is either activated or inactivated (e.g., by using homologous recombination methods) to alter the level of expression of one or more of the native FGFR-L polypeptides.

These non-human animals may be used for drug candidate screening. In such screening, the impact of a drug candidate on the animal may be measured. For example, drug candidates may decrease or increase the expression of the FGFR-L gene. In certain embodiments, the amount of FGFR-L polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for other Modulators of FGFR-L Polypeptide Activity

In some situations, it may be desirable to identify molecules that are modulators, i.e., agonists or antagonists, of the activity of FGFR-L polypeptide. Natural or synthetic molecules that modulate FGFR-L polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of an FGFR-L polypeptide. Most commonly, a test molecule will interact directly with an FGFR-L polypeptide. However, it is also contemplated that a test molecule may also modulate FGFR-L polypeptide activity indirectly, such as by affecting FGFR-L gene expression, or by binding to an FGFR-L polypeptide binding partner (e.g., receptor or ligand). In one embodiment, a test molecule will bind to an FGFR-L polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with FGFR-L polypeptides are encompassed by the present invention. In certain embodiments, an FGFR-L polypeptide is incubated with a test molecule under conditions that permit the interaction of the test molecule with an FGFR-L polypeptide, and the extent of the interaction is measured. The test molecule can be screened in a substantially purified form or in a crude mixture.

In certain embodiments, an FGFR-L polypeptide agonist or antagonist may be a protein, peptide, carbohydrate, lipid, or small molecular weight molecule that interacts with FGFR-L polypeptide to regulate its activity. Molecules which regulate FGFR-L polypeptide expression include nucleic acids which are complementary to nucleic acids encoding an FGFR-L polypeptide, or are complementary to nucleic acids sequences which direct or control the expression of FGFR-L polypeptide, and which act as anti-sense regulators of expression.

Once a test molecule has been identified as interacting with an FGFR-L polypeptide, the molecule may be further evaluated for its ability to increase or decrease FGFR-L polypeptide activity. The measurement of the interaction of a test molecule with FGFR-L polypeptide may be carried out in several formats, including cell-based binding assays, membrane binding assays, solution-phase assays, and immunoassays. In general, a test molecule is incubated with an FGFR-L polypeptide for a specified period of time, and FGFR-L polypeptide activity is determined by one or more assays for measuring biological activity.

The interaction of test molecules with FGFR-L polypeptides may also be assayed directly using polyclonal or monoclonal antibodies in an immunoassay. Alternatively, modified forms of FGFR-L polypeptides containing epitope tags as described herein may be used in solution and immunoassays.

In the event that FGFR-L polypeptides display biological activity through an interaction with a binding partner (e.g., a receptor or a ligand), a variety of in vitro assays may be used to measure the binding of an FGFR-L polypeptide to the corresponding binding partner (such as a selective binding agent, receptor, or ligand). These assays may be used to screen test molecules for their ability to increase or decrease the rate and/or the extent of binding of an FGFR-L polypeptide to its binding partner. In one assay, an FGFR-L polypeptide is immobilized in the wells of a microtiter plate. Radiolabeled FGFR-L polypeptide binding partner (for example, iodinated FGFR-L polypeptide binding partner) and a test molecule can then be added either one at a time (in either order) or simultaneously to the wells. After incubation, the wells can be washed and counted for radioactivity, using a scintillation counter, to determine the extent to which the binding partner bound to the FGFR-L polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing FGFR-L polypeptide binding partner to the microtiter plate wells, incubating with the test molecule and radiolabeled FGFR-L polypeptide, and determining the extent of FGFR-L polypeptide binding. See, e.g., *Current Protocols in Molecular Biology*, chap. 18 (Ausubel et al., eds., Green Publishers Inc. and Wiley and Sons 1995).

As an alternative to radiolabeling, an FGFR-L polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to an FGFR-L polypeptide or to an FGFR-L polypeptide binding partner, and which is conjugated to biotin, may also be used for purposes of detection following incubation of the complex with enzyme-linked streptavidin linked to AP or HRP.

A FGFR-L polypeptide or an FGFR-L polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between an FGFR-L polypeptide and its binding partner can be assessed using the methods described herein. Alternatively, the substrate-protein complex can be immobilized in a column with the test molecule and complementary protein passing through the column. The formation of a complex between an FGFR-L polypeptide and its binding partner can then be assessed using any of the techniques described herein (e.g., radiolabelling or antibody binding).

Another in vitro assay that is useful for identifying a test molecule which increases or decreases the formation of a complex between an FGFR-L polypeptide binding protein and an FGFR-L polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either FGFR-L polypeptide or an FGFR-L polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between an FGFR-L polypeptide and an FGFR-L polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between an FGFR-L polypeptide and FGFR-L polypeptide binding partner. The assays may be automated to screen compounds generated in phage display, synthetic peptide, and chemical synthesis libraries.

Compounds which increase or decrease the formation of a complex between an FGFR-L polypeptide and an FGFR-L polypeptide binding partner may also be screened in cell culture using cells and cell lines expressing either FGFR-L polypeptide or FGFR-L polypeptide binding partner. Cells and cell lines may be obtained from any mammal, but preferably will be from human or other primate, canine, or rodent sources. The binding of an FGFR-L polypeptide to cells expressing FGFR-L polypeptide binding partner at the surface is evaluated in the presence or absence of test molecules, and the extent of binding may be determined by, for example, flow cytometry using a biotinylated antibody to an FGFR-L polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the FGFR-L gene. In certain embodiments, the amount of FGFR-L polypeptide or an FGFR-L polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al, 1994, *Proc. Natl. Acad. Sci. U.S.A.* 91:664-68. For example, an 11 amino acid sequence (Y-G-R-K-K-R-R-Q-R-R-R; SEQ ID NO: 9) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 10), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, an FGFR-L antagonist (such as an anti-FGFR-L selective binding agent, small molecule, soluble receptor, or antisense oligonucleotide) can be administered intracellularly to inhibit the activity of an FGFR-L molecule. As used herein, the term "FGFR-L molecule" refers to both FGFR-L nucleic acid molecules and FGFR-L polypeptides as defined herein. Where desired, the FGFR-L protein itself may also be internally administered to a cell using these procedures. See also, Straus, 1999, *Science* 285:1466-67.

Cell Source Identification Using FGFR-L Polypeptide

In accordance with certain embodiments of the invention, it may be useful to be able to determine the source of a certain cell type associated with an FGFR-L polypeptide. For example, it may be useful to determine the origin of a disease or pathological condition as an aid in selecting an appropriate therapy. In certain embodiments, nucleic acids encoding an FGFR-L polypeptide can be used as a probe to identify cells described herein by screening the nucleic acids of the cells with such a probe. In other embodiments, one may use anti-FGFR-L polypeptide antibodies to test for the presence of FGFR-L polypeptide in cells, and thus, determine if such cells are of the types described herein.

FGFR-L Polypeptide Compositions and Administration

Therapeutic compositions are within the scope of the present invention. Such FGFR-L polypeptide pharmaceutical compositions may comprise a therapeutically effective amount of an FGFR-L polypeptide or an FGFR-L nucleic acid molecule in admixture with a pharmaceutically or physiologically acceptable formulation agent selected for suitability with the mode of administration. Pharmaceutical compositions may comprise a therapeutically effective amount of one or more FGFR-L polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the FGFR-L molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, FGFR-L polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the FGFR-L polypeptide product may be formulated as a lyophilizate using appropriate excipients such as sucrose.

The FGFR-L polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired FGFR-L molecule in a pharmaceutically acceptable vehicle. A particularly suitable vehicle for parenteral injection is sterile distilled water in which an FGFR-L molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, FGFR-L polypeptide may be formulated as a dry powder for inhalation. FGFR-L polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, FGFR-L polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the FGFR-L polypeptide. Diluents, flavorings, low melting point waxes, vegetable oils, lubricants, suspending agents, tablet disintegrating agents, and binders may also be employed.

Another pharmaceutical composition may involve an effective quantity of FGFR-L polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional FGFR-L polypeptide pharmaceutical compositions will be evident to those skilled in the art, including formulations involving FGFR-L polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethylmethacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The FGFR-L pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of an FGFR-L pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the FGFR-L molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the FGFR-L molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use FGFR-L polypeptide pharmaceutical compositions in an ex vivo manner. In such instances, cells, tissues, or organs that have been removed from the patient are exposed to FGFR-L polypeptide pharmaceutical compositions after which the cells, tissues, or organs are subsequently implanted back into the patient.

In other cases, an FGFR-L polypeptide can be delivered by implanting certain cells that have been genetically engineered, using methods such as those described herein, to express and secrete the FGFR-L polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more FGFR-L polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent FGFR-L gene, or an underexpressed gene, and thereby produce a cell which expresses therapeutically efficacious amounts of FGFR-L polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of an FGFR-L polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired FGFR-L polypeptide. The control element controls a portion of the DNA present in the host cell genome. Thus, the expression of the desired FGFR-L polypeptide may be achieved not by transfection of DNA that encodes the FGFR-L gene itself, but rather by the use of targeting DNA (containing regions of homology with the endogenous gene of interest) coupled with DNA regulatory segments that provide the endogenous gene sequence with recognizable signals for transcription of an FGFR-L gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, FGFR-L polypeptide production from a cell's endogenous FGFR-L gene involves first using homologous recombination to place a recombination sequence from a site-specific recombination system (e.g., Cre/loxP, FLP/FRT) (Sauer, 1994, *Curr. Opin. Biotechnol.,* 5:521-27; Sauer, 1993, *Methods Enzymol.,* 225:890-900) upstream of (i.e., 5' to) the cell's endogenous genomic FGFR-L polypeptide coding region. A plasmid containing a recombination site homologous to the site that was placed just upstream of the genomic FGFR-L polypeptide coding region is introduced into the modified cell line along with the appropriate recombinase enzyme. This recombinase causes the plasmid to integrate, via the plasmid's recombination site, into the recombination site located just upstream of the genomic FGFR-L polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased FGFR-L polypeptide production from the cell's endogenous FGFR-L gene.

A further method to use the cell line in which the site specific recombination sequence had been placed just upstream of the cell's endogenous genomic FGFR-L polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.,* 5:521-27; Sauer, 1993, *Methods Enzymol.,* 225:890-900) that would create a new or modified transcriptional unit resulting in de novo or increased FGFR-L polypeptide production from the cell's endogenous FGFR-L gene.

An additional approach for increasing, or causing, the expression of FGFR-L polypeptide from a cell's endogenous FGFR-L gene involves increasing, or causing, the expression of a gene or genes (e.g., transcription factors) and/or decreasing the expression of a gene or genes (e.g., transcriptional repressors) in a manner which results in de novo or increased FGFR-L polypeptide production from the cell's endogenous FGFR-L gene. This method includes the introduction of a non-naturally occurring polypeptide (e.g., a polypeptide comprising a site specific DNA binding domain fused to a transcriptional factor domain) into the cell such that de novo or increased FGFR-L polypeptide production from the cell's endogenous FGFR-L gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of FGFR-L polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding an FGFR-L polypeptide, which nucleotides may be used as targeting sequences.

FGFR-L polypeptide cell therapy, e.g., the implantation of cells producing FGFR-L polypeptides, is also contemplated. This embodiment involves implanting cells capable of synthesizing and secreting a biologically active form of FGFR-L polypeptide. Such FGFR-L polypeptide-producing cells can be cells that are natural producers of FGFR-L polypeptides or may be recombinant cells whose ability to produce FGFR-L polypeptides has been augmented by transformation with a gene encoding the desired FGFR-L polypeptide or with a gene augmenting the expression of FGFR-L polypeptide. Such a modification may be accomplished by means of a vector suitable for delivering the gene as well as promoting its expression and secretion. In order to minimize a potential immunological reaction in patients being administered an FGFR-L polypeptide, as may occur with the administration of a polypeptide of a foreign species, it is preferred that the natural cells producing FGFR-L polypeptide be of human origin and produce human FGFR-L polypeptide. Likewise, it is preferred that the recombinant cells producing FGFR-L polypeptide be transformed with an expression vector containing a gene encoding a human FGFR-L polypeptide.

Implanted cells may be encapsulated to avoid the infiltration of surrounding tissue. Human or non-human animal cells may be implanted in patients in biocompatible, semipermeable polymeric enclosures or membranes that allow the release of FGFR-L polypeptide, but that prevent the destruction of the cells by the patient's immune system or by other detrimental factors from the surrounding tissue. Alternatively, the patient's own cells, transformed to produce FGFR-L polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of FGFR-L polypeptides is also envisioned. One example of a gene therapy technique is to use the FGFR-L gene (either genomic DNA, cDNA, and/or synthetic DNA) encoding an FGFR-L polypeptide which may be operably linked to a constitutive or inducible promoter to form a "gene therapy DNA construct." The promoter may be homologous or heterologous to the endogenous FGFR-L gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the FGFR-L gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al, 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding FGFR-L polypeptide into cells via local injection of an FGFR-L nucleic acid molecule or by other appropriate viral or non-viral delivery vectors. Hefti 1994, *Neurobiology* 25:1418-35. For example, a nucleic acid molecule encoding an FGFR-L polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding an FGFR-L polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that FGFR-L gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous FGFR-L polypeptide expression in a cell via gene therapy is to insert one or more enhancer elements into the FGFR-L polypeptide promoter, where the enhancer elements can serve to increase transcriptional activity of the FGFR-L gene. The enhancer elements used will be selected based on the tissue in which one desires to activate the gene—enhancer elements known to confer promoter activation in that tissue will be selected. For example, if a gene encoding an FGFR-L polypeptide is to be "turned on" in T-cells, the lck promoter enhancer element may be used. Here, the functional portion of the transcriptional element to be added may be inserted into a fragment of DNA containing the FGFR-L polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease FGFR-L polypeptide expression by modifying the nucleotide sequence of the endogenous promoter. Such modification is typically accomplished via homologous recombination methods. For example, a DNA molecule containing all or a portion of the promoter of the FGFR-L gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding FGFR-L gene. The deletion of the TATA box or the transcription activator binding site in the promoter may be accomplished by generating a DNA construct comprising all or the relevant portion of the FGFR-L polypeptide promoter (from the same or a related species as the FGFR-L gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

FGFR-L nucleic acid molecules, polypeptides, and agonists and antagonists thereof can be used to treat, diagnose, ameliorate, or prevent a number of diseases, disorders, or conditions, including those recited herein.

FGFR-L polypeptide agonists and antagonists include those molecules which regulate FGFR-L polypeptide activity and either increase or decrease at least one activity of the mature form of the FGFR-L polypeptide. Agonists or antagonists may be co-factors, such as a protein, peptide, carbohydrate, lipid, or small molecular weight molecule, which interact with FGFR-L polypeptide and thereby regulate its activity. Potential polypeptide agonists or antagonists include antibodies that react with either soluble or membrane-bound forms of FGFR-L polypeptides that comprise part or all of the extracellular domains of the said proteins. Molecules that regulate FGFR-L polypeptide expression typically include nucleic acids encoding FGFR-L polypeptide that can act as anti-sense regulators of expression.

The extra-cellular domain of FGFR-L polypeptide was found to share sequence identity with the Fibroblast Growth Factor (FGF) Receptor family of genes, FGFR-L nucleic acid molecules, polypeptides, and agonists and antagonists thereof (including, but not limited to, anti-FGFR-L selective binding agents) may be useful in the identification of novel growth factors.

The sequence identity between FGFR-L polypeptide and the FGF Receptor family also suggests that FGFR-L polypeptides may play a role in mitogenesis in fibroblasts, endothelial cells, and epithelial cells. Such epithelial cells include pancreatic ductal cells, which have been shown to differentiate in response to an FGF to form insulin producing beta islet cells. In addition to a 3-4 kb FGFR-L transcript, pancreas also expresses a 6 kb transcript which may encode a FGFR-L polypeptide variant. This potential FGFR-L polypeptide variant may have activities that differ from those of the FGFR-L transcript. Accordingly, FGFR-L nucleic acid molecules, polypeptides, and agonists and antagonists thereof may be useful in tissue repair, wound healing, the modulation of angiogenesis, and the diagnosis and treatment of diabetes.

In several tumor cell lines, the extra-cellular domain of FGFR-L polypeptide is shed into the culture medium. This suggests that the FGFR-L polypeptide extra-cellular domain may play a role in the growth and/or differentiation of tumor cells. Accordingly, FGFR-L nucleic acid molecules, polypeptides, and agonists and antagonists thereof may be useful in the diagnosis and treatment of cancer.

The FGFR-L gene was found to be up-regulated in bone marrow stromal cell lines that support the maintenance of hematopoietic stem cells. Accordingly, FGFR-L nucleic acid molecules and polypeptides may be useful for ex vivo expansion of stem cells, gene therapy protocols, or treatment of hematopoietic disorders.

The FGFR-L gene was also found to be up-regulated under conditions of osteoclastogenesis. Accordingly, FGFR-L nucleic acid molecules, polypeptides, and agonists and antagonists thereof may be useful in the diagnosis and treatment of bone disorders including, but not limited to, osteoporosis, osteopetrosis, osteogenesis imperfecta, Paget's disease, periodontal disease, and hypercalcemia.

FGFR-L polypeptide expression was detected in kidney. Accordingly, FGFR-L nucleic acid molecules, polypeptides, and agonists and antagonists thereof may be useful for the diagnosis and/or treatment of diseases involving the kidney. Examples of such diseases include, but are not limited to, acute and chronic glomerulonephritis. Other diseases associated with the kidney are encompassed within the scope of this invention.

The FGFR-L gene is most abundantly expressed in adipose tissue as determined by in situ hybridization. Based on this expression pattern, FGFR-L polypeptides may play a role in adipogenesis or in adipocyte function, including but not limited to, energy balance control and lipolysis. Accordingly, FGFR-L nucleic acid molecules, polypeptides, and agonists and antagonists thereof may be useful for achieving dietary weight loss, weight gain, or treating cachexia.

Agonists or antagonists of FGFR-L polypeptide function may be used (simultaneously or sequentially) in combination with one or more cytokines, growth factors, antibiotics, anti-inflammatories, and/or chemotherapeutic agents as is appropriate for the condition being treated.

Other diseases caused by or mediated by undesirable levels of FGFR-L polypeptides are encompassed within the scope of the invention. Undesirable levels include excessive levels of FGFR-L polypeptides and sub-normal levels of FGFR-L polypeptides.

Uses of FGFR-L Nucleic Acids and Polypeptides

Nucleic acid molecules of the invention (including those that do not themselves encode biologically active polypeptides) may be used to map the locations of the FGFR-L gene and related genes on chromosomes. Mapping may be done by techniques known in the art, such as PCR amplification and in situ hybridization.

FGFR-L nucleic acid molecules (including those that do not themselves encode biologically active polypeptides), may be useful as hybridization probes in diagnostic assays to test, either qualitatively or quantitatively, for the presence of an FGFR-L nucleic acid molecule in mammalian tissue or bodily fluid samples.

Other methods may also be employed where it is desirable to inhibit the activity of one or more FGFR-L polypeptides. Such inhibition may be effected by nucleic acid molecules that are complementary to and hybridize to expression control sequences (triple helix formation) or to FGFR-L mRNA. For example, antisense DNA or RNA molecules, which have a sequence that is complementary to at least a portion of an FGFR-L gene can be introduced into the cell. Anti-sense probes may be designed by available techniques using the sequence of the FGFR-L gene disclosed herein. Typically, each such antisense molecule will be complementary to the start site (5' end) of each selected FGFR-L gene. When the antisense molecule then hybridizes to the corresponding FGFR-L mRNA, translation of this mRNA is prevented or reduced. Anti-sense inhibitors provide information relating to the decrease or absence of an FGFR-L polypeptide in a cell or organism.

Alternatively, gene therapy may be employed to create a dominant-negative inhibitor of one or more FGFR-L polypeptides. In this situation, the DNA encoding a mutant polypeptide of each selected FGFR-L polypeptide can be prepared and introduced into the cells of a patient using either viral or non-viral methods as described herein. Each such mutant is typically designed to compete with endogenous polypeptide in its biological role.

In addition, an FGFR-L polypeptide, whether biologically active or not, may be used as an immunogen, that is, the polypeptide contains at least one epitope to which antibodies may be raised. Selective binding agents that bind to an FGFR-L polypeptide (as described herein) may be used for in vivo and in vitro diagnostic purposes, including, but not limited to, use in labeled form to detect the presence of FGFR-L polypeptide in a body fluid or cell sample. The antibodies may also be used to prevent, treat, or diagnose a number of diseases and disorders, including those recited herein. The antibodies may bind to an FGFR-L polypeptide so as to diminish or block at least one activity characteristic of an FGFR-L polypeptide, or may bind to a polypeptide to increase at least one activity characteristic of an FGFR-L polypeptide (including by increasing the pharmacokinetics of the FGFR-L polypeptide).

FGFR-L polypeptides can be used to clone FGFR-L polypeptide ligands using an "expression cloning" strategy. Radiolabeled ($^{125}$Iodine) FGFR-L polypeptide or "affinity/activity-tagged" FGFR-L polypeptide (such as an Fc fusion or an alkaline phosphatase fusion) can be used in binding assays to identify a cell type, cell line, or tissue that expresses FGFR-L polypeptide ligands. RNA isolated from such cells or tissues can then be converted to cDNA, cloned into a mammalian expression vector, and transfected into mammalian cells (e.g., COS or 293) to create an expression library. Radiolabeled or tagged FGFR-L polypeptide can then be used as an affinity reagent to identify and isolate the subset of cells in this library expressing FGFR-L polypeptide ligands. DNA is then isolated from these cells and transfected into mammalian cells to create a secondary expression library in which the fraction of cells expressing FGFR-L polypeptide ligands would be many-fold higher than in the original library. This enrichment process can be repeated iteratively until a single recombinant clone containing an FGFR-L polypeptide ligand is isolated. Isolation of FGFR-L polypeptide ligands is useful for identifying or developing novel agonists and antagonists of the FGFR-L polypeptide signaling pathway. Such agonists and antagonists include FGFR-L polypeptide ligands, anti-FGFR-L polypeptide ligand antibodies, small molecules, or antisense oligonucleotides.

The murine and human FGFR-L nucleic acids of the present invention are also useful tools for isolating the corresponding chromosomal FGFR-L polypeptide genes. For example, mouse chromosomal DNA containing FGFR-L sequences can be used to construct knockout mice, thereby permitting an examination of the in vivo role for FGFR-L polypeptide. The human FGFR-L genomic DNA can be used to identify heritable tissue-degenerating diseases.

A deposit of cDNA encoding murine FGFR-L polypeptide, having Accession No. PTA-1062, was made with the American Type Culture Collection, 10801 University Boulevard, Manassas, Va. 20110-2209 on Dec. 15, 1999.

EXAMPLE 1

Cloning of the Murine FGFR-L Polypeptide Gene

Generally, materials and methods as described in Sambrook et al. supra were used to clone and analyze the gene encoding rat FGFR-L polypeptide.

Sequences encoding the murine FGFR-L polypeptide were isolated from a mouse cDNA library derived from a mixture of two hematopoietic stem cell supportive bone marrow stromal cell lines (F4 and F10). Murine bone marrow stromal cell lines D3, F4, and F10 were obtained from Dr. R. Ploemacher (Erasmus University, Rotterdam, The Netherlands) and cultured at 32° C. and 5% $CO_2$ in IMDM supplemented with 10% fetal bovine serum, 5% horse serum, 2 mM glutamine, 0.1 mM β-mercaptoethanol and 1 µM hydrocortisone (Na Succinate salt). A mouse bone marrow stromal cDNA library was prepared by isolating RNA from F4 and F10 cells using the Trizol method (LTI). Poly-A RNA was purified using oligo-dT magnetic beads (Dynal) and equal amounts of poly-A RNA (1.5 ug each of F4 and F10 RNA) were mixed. An oligo-dT primed full-length cDNA library was constructed from the F4/F10 RNA mixture using the Superscript Plasmid System for cDNA Synthesis and Plasmid Cloning (LTI).

The mouse bone marrow stromal cDNA library, containing $6 \times 10^6$ transformants, was plated, and $3.4 \times 10^4$ colonies were selected and transferred in parallel into 96-well plates and spotted onto filters. The filters were then probed with $^{32}$P-dCTP-labeled first strand cDNA generated from poly-A mRNA isolated from the bone marrow stromal D3 cell line. Of the $3.4 \times 10^4$ colonies spotted onto filters, 11,232 failed to hybridize with the D3 probe. Plasmid was isolated from these non-hybridizing colonies and the 5' end of their cDNA inserts sequenced.

One clone (smsf2-00017-f4), showing homology with various members of the FGF receptor family, was identified in the sequence analysis. A full-length clone (smsf2-00017-f4-41.6) was obtained by screening a Southern blot of 56 mouse bone marrow stromal cDNA pools—each pool comprising $1 \times 10^4$ clones from the mouse bone marrow stromal cDNA library. The pool possessing the longest insert was subsequently plated and rescreened.

Sequence analysis of the full-length cDNA for murine FGFR-L polypeptide indicated that the gene encodes a type I transmembrane protein (FIG. 1B, predicted transmembrane domain: L-P-W-P-V-V-I-G-I-P-A-G-A-V-F-I-L-G-T-V-L-L-W-L-C; SEQ ID NO: 12). The murine FGFR-L polypeptide gene comprises a 1587 bp open reading frame encoding a protein of 529 amino acids and possessing a potential signal peptide at its amino terminus (FIG. 1A, predicted signal peptide: M-T-R-S-P-A-L-L-L-L-L-G-A-L-P-S-A-E-A; SEQ ID NO: 11). FIGS. 1A-1C illustrate the nucleotide sequence of the murine FGFR-L nucleic acid sequence and the deduced amino acid sequence of murine FGFR-L polypeptide. A murine extracellular domain-Fc fusion protein has an apparent Molecular Weight, as determined by SDS-PAGE, of approximately 55 kD.

While the extracellular domain of FGFR-L polypeptide is most closely related to the FGF receptor family, the protein's cytoplasmic domain does not contain a kinase domain or other recognizable domain. FIGS. 3A-3B illustrate the amino acid sequence alignment of murine FGFR-L polypeptide and the known protein for which FGFR-L polypeptide shares the closest homology, Iberian ribbed newt (*Pleurodeles waltlii*) FGF receptor-4. Computer analysis using the BLAST program, also indicated that murine FGFR-L polypeptide was closely related to a single, 486 bp human EST (GenBank accession number AI245701) isolated from human kidney. A 379 bp stretch of this EST showed an 87% identity with FGFR-L polypeptide, suggesting the existence of a human ortholog.

EXAMPLE 2

Cloning of the Human FGFR-L Polypeptide Gene

Generally, materials and methods as described in Sambrook et al. supra are used to clone and analyze the gene encoding human FGFR-L polypeptide.

A human spleen and mixed tissue cDNA library was prepared as follows. Total RNA was extracted from human tissues using Trizol extraction procedures (Gibco-BRL, Rockville, Md.) and poly-A$^+$ RNA was selected from this total RNA using Dynabeads (Dynal, Oslo, Norway) according to the manufacturer's recommended protocol. Random primed or oligo(dT) primed cDNA was synthesized from this poly-A$^+$ RNA using the the Superscript Plasmid System for cDNA Synthesis and Plasmid Cloning kit (Gibco-BRL, Rockville, Md.) according to the manfacturer's recommended protocol. The resulting cDNA was digested with appropriate restriction enzymes and cloned into the pSPORT 1 vector. Ligation products were transformed into *E. coli* using standard techniques known in the art and transformants were selected on bacterial media plates containing an appropriate antibotic. The cDNA library consisted of all, or a subset, of these transformants.

Plasmid DNA isolated from pools of $1\times10^4$ colonies was used as a template in PCR amplifications performed with the primers 5'-C-G-C-T-G-A-C-C-A-T-G-T-G-G-A-C-C-A-A-G-G-A-T-G-3' (SEQ ID NO: 13) and 5'-C-T-T-G-A-C-C-C-C-A-G-A-A-G-G-A-G-C-T-G-T-C-G-G-3' (SEQ ID NO: 14). The PCR primers were designed on the basis of the human EST sequence AI245701 described in Example 1. Several pools yielded a 234 bp fragment which was subcloned and determined to have a nucleic acid sequence corresponding to positions 208-441 of the human FGFR-L nucleic acid sequence shown in FIG. 2A.

Plasmid pools that yielded the 234 bp PCR product in the amplification reactions above were then plated for colony hybridization analysis. Plated colonies were screened using the 234 bp PCR fragment generated above as a probe following radiolabeling with the Rediprime II random prime labeling kit (Amersham, Piscataway, N.J.). A 1333 bp cDNA insert was determined to have a sequence corresponding to positions 118-1450 of the human FGFR-L nucleic acid sequence shown in FIGS. 2A-2C. Assembly of this 1333 bp sequence and the 234 bp sequence of AI245701 yielded the human FGFR-L nucleic acid sequence shown in FIGS. 2A-2C.

Baker et al. (PCT Pub. No. WO 99/63088) teach a polypeptide sequence of 504 amino acids (SEQ ID NO: 15) which they call PRO943 that shares sequence identity with human FGFR-L polypeptide. Ruben and Young (PCT Pub. No. WO 00/24756) teach a nucleic acid sequence of 3112 bp (SEQ ID NO: 16) encoding a polypeptide of 504 amino acids (SEQ ID NO: 17) which they call Fibroblast Growth Factor Receptor-5 (FGFR5) that shares sequence identity with human FGFR-L polypeptide. Finally, Wiedemann and Trueb, 2000, *Genomics* 69:275-79, teach a nucleic acid sequence of 3080 bp (SEQ ID NO: 18) encoding a polypeptide 504 amino acids (SEQ ID NO: 19) which they call Fibroblast Growth Factor Receptor-Like Protein 1 (FG-FRL1) that shares sequence identity with human FGFR-L polypeptide.

EXAMPLE 3

FGFR-L mRNA Expression

The expression of FGFR-L mRNA was examined by Northern blot analysis. Multiple murine and human tissue northern blots (Clontech) were probed with a $^{32}$P-dCTP labeled, 234 bp PCR fragment corresponding to a portion of the human FGFR-L gene (see Example 2). Additional blots containing RNA isolated from a variety of cell lines were also screened with this probe.

Northern blots were prehybridized for 2 hours at 42° C. in 5×SSC, 35% deionized formamide, 0.05% (w/v) sodium pyrophosphate, 20 mM sodium phosphate pH 6.8, 5 mM EDTA, 5×Denhardt's solution, 0.2% SDS, and 94 µg/mL denatured salmon sperm DNA, and then were hybridized at 42° C. overnight in fresh prehybridization buffer containing approximately 1 ng/mL of the labeled probe. Following hybridization, the filters were washed once in prehybridization buffer for 5 minutes at room temperature, once for 5 minutes at room temperature in 2×SSC and 0.1% SDS, and then twice for 20 minutes at 42° C. in 2×SSC and 0.1% SDS. The blots were then exposed to autoradiography.

Analysis of the Northern blots (FIGS. 5-7) indicated that a single transcript having a molecular mass of 2.9 kb was highly expressed in murine liver, kidney, F4 and F10 bone marrow stromal cells, NIH-3T3 cells, and ST2 bone marrow stromal cells (following exposure with vitamin D3 and dexamethasone). The detection of a single transcript in the positive samples suggests that, in these tisues, there is no obvious splice variant encoding a longer cytoplasmic domain that could contain a kinase domain or other recognizable domain. Weak expression of the transcript was detected in murine heart, brain, lung, skeletal muscle, testis, F10 bone marrow stromal cells, and ST2 cells (prior to exposure with Vitamin D3 and Dexamethasone).

Figure 8:
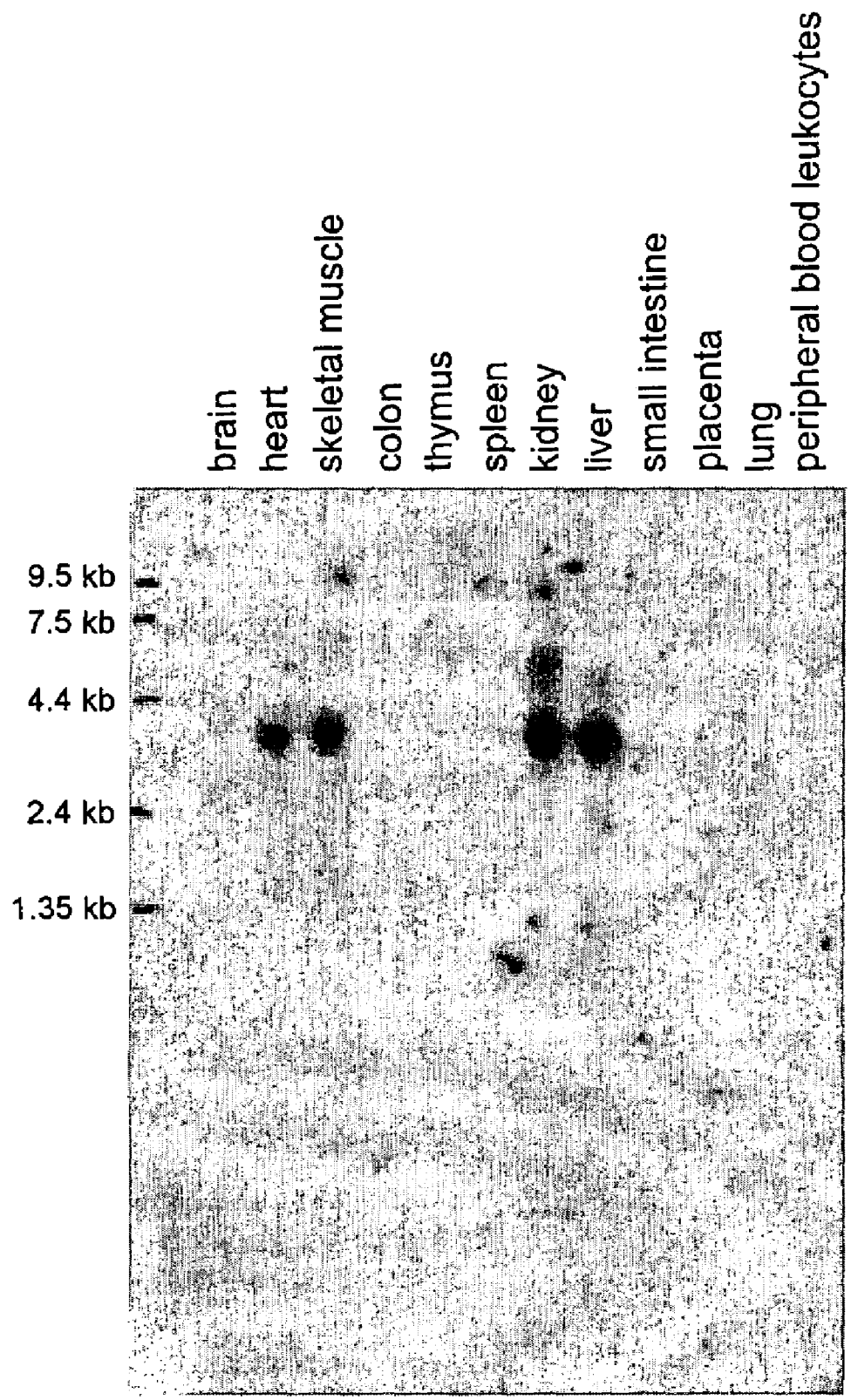
FIG. 8 illustrates the expression of FGFR-L mRNA as detected by Northern blot analysis in human brain, heart, skeletal muscle, colon, thymus, spleen, kidney, liver, small intestine, placenta, lung, and peripheral blood leukocytes.
Figure 9:
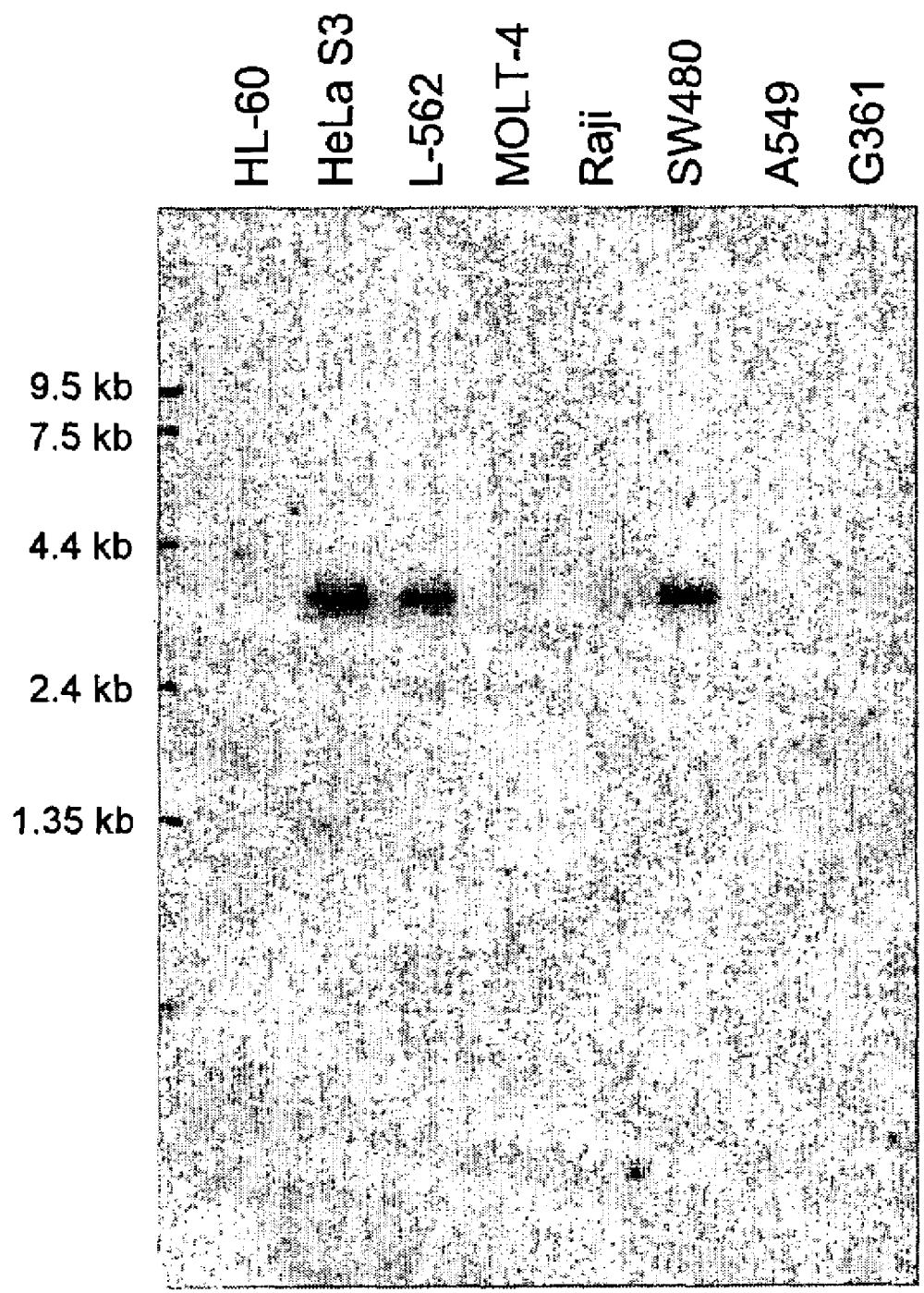
FIG. 9 illustrates the expression of FGFR-L mRNA as detected by Northern blot analysis in promyelocytic leukemia HL-60 cells, HeLa S3 cells, chronic myelogenous leukemia L-562 cells, lymphoblastic leukemia MOLT-4 cells, Burkitt's lymphoma Raji cells, colorectal adenocarcinoma SW480 cells, lung carcinoma A549 cells, and melanoma G361 cells.
Figure 10:
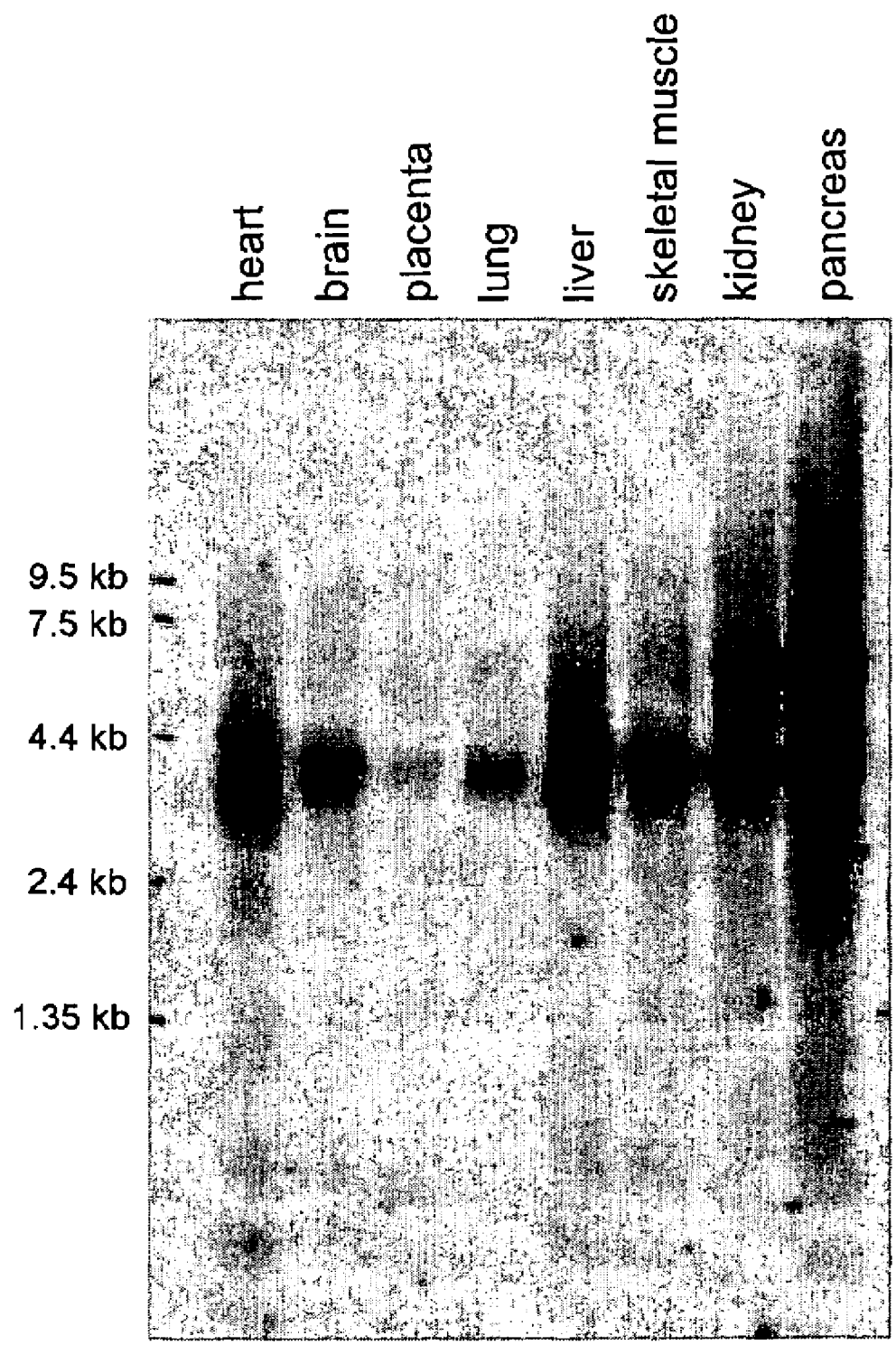
FIG. 10 illustrates the expression of FGFR-L mRNA as detected by Northern blot analysis in human heart, brain, placenta, lung, liver, skeletal muscle, kidney, and pancreas.

Northern blot analysis (FIGS. 8-10) also indicated that a transcript having a molecular mass of 3.2 kb was highly expressed among human tissues and that a transcript having a molecular mass of 6.0 kb was expressed in human pancreas. The existance of the 6.0 kb transcript suggests that a functionally distinct FGFR-L protein variant may exist. Lower expression of the 3.2 kb transcript was seen in liver, kidney, heart, skeletal muscle, brain, and the cell lines HeLa, K562, SW480, Molt4, and Raji.

Figure 11:
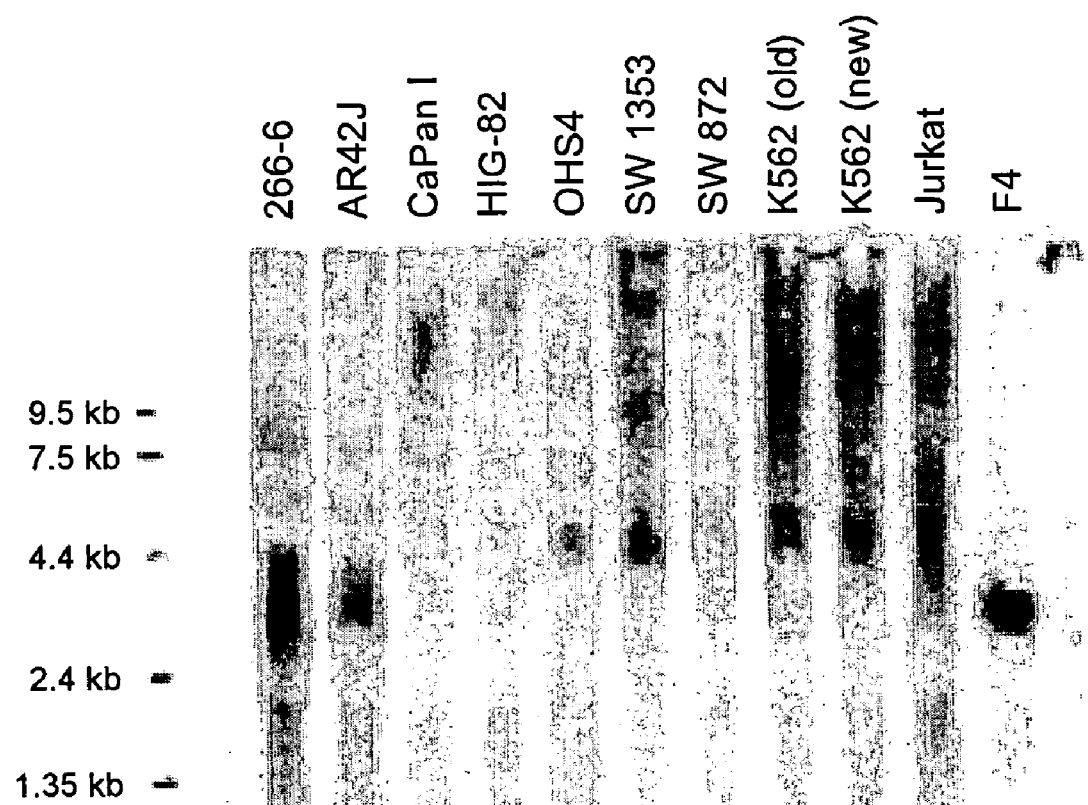
FIG. 11 illustrates the expression of FGFR-L mRNA as detected by Northern blot analysis in 266-6 cells, AR42J cells, CaPan I cells, HIG-82 cells, OHS4 cells, SW 1353 cells, SW 872 cells, K562 (old, i.e., later passage) cells, K562 (new, i.e., earlier passage) cells, Jurkat cells, and F4 cells.
Figure 12:
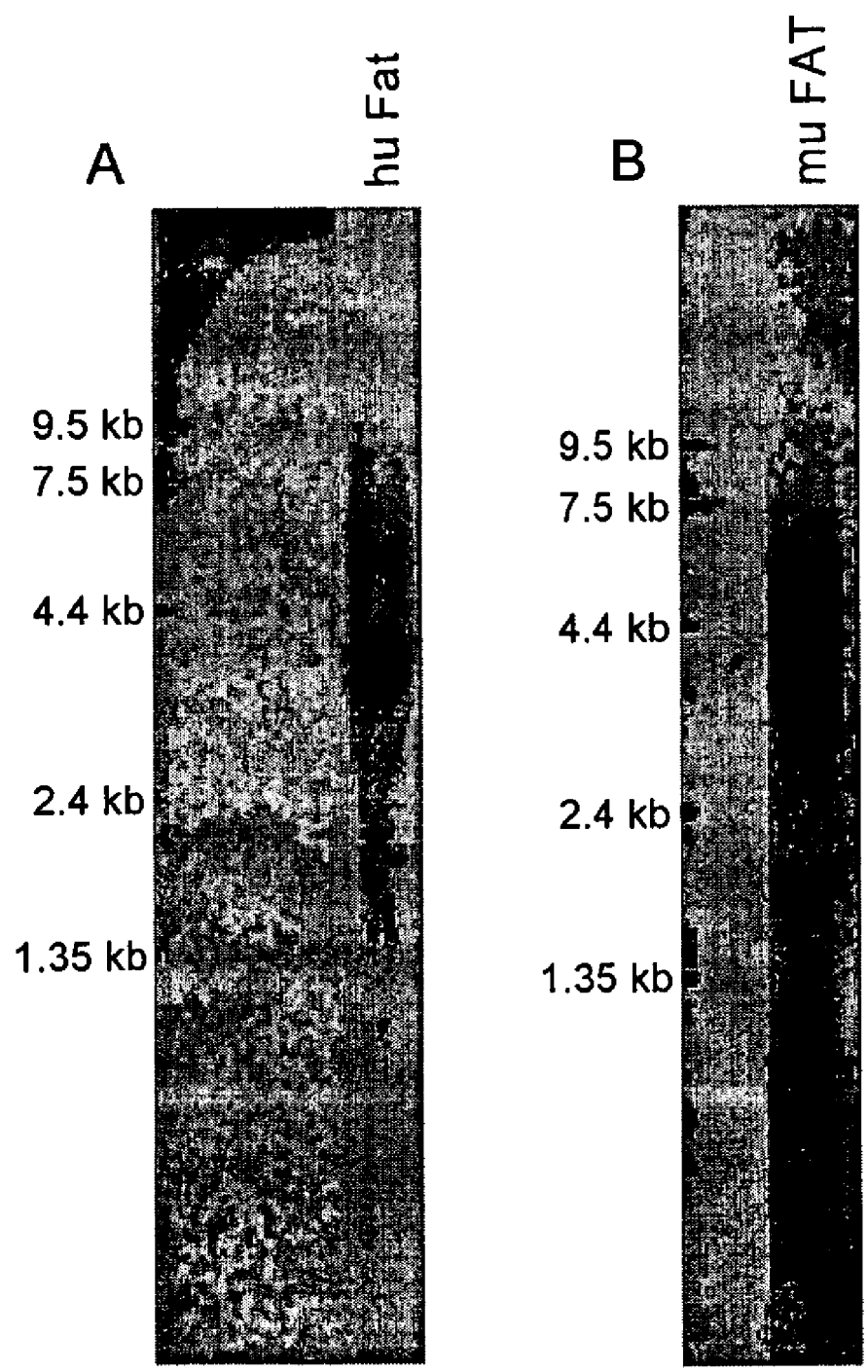
FIGS. 12A-12B illustrate the expression of FGFR-L mRNA as detected by Northern blot analysis in human adipose tissue (using a human FGFR-L-derived probe) and murine adipose tissue (using a murine FGFR-L-derived probe)

Northern blot analysis (FIG. 11) also indicated that single transcript could be detected in the following cell lines: 266-6 (mouse acinar pancreatic tumor), AR42J (rat pancreas tumor, exocrine), CaPan I (human pancreatic adenocarcinoma), HIG-82 (rabbit synoviocyte), OHS4 (human osteoblast), SW 1353 (human chondrosarcoma, humerous), SW 872 (human liposarcoma), K562 (old, i.e., later passage; chronic myelogenous leukemia; later passage), K562 (new, i.e., earlier passage), Jurkat (human T cell line), and F4 (murine bone marrow derived stromal cell line). Probes derived from human and murine FGFR-L cDNA were also capable of detecting FGFR-L mRNA in human and murine adipose tissue, respectively (FIGS. 12A-12B).

Figure 13:
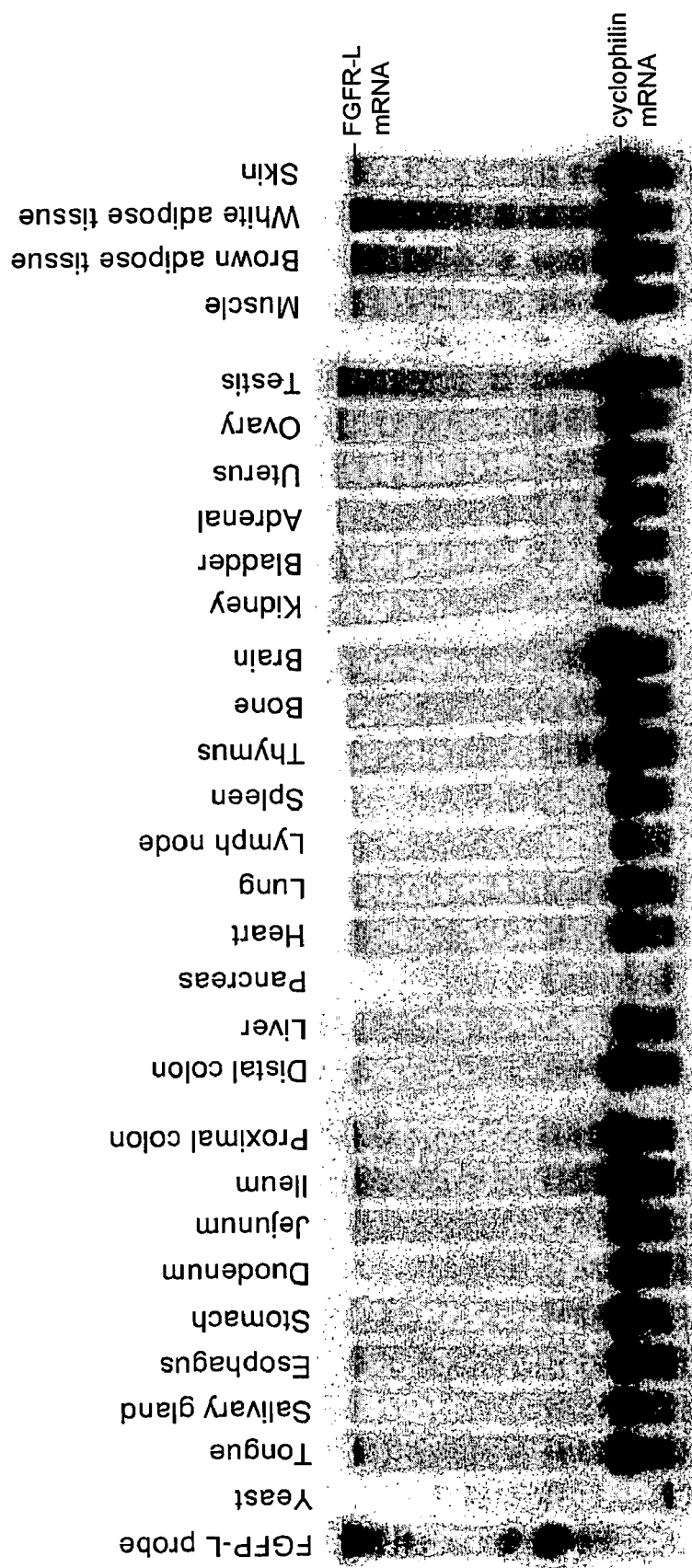
FIG. 13 illustrates the expression of FGFR-L mRNA in a number of murine tissues as detected in an RNAse protection assay. The absence of the cyclophilin band in the pancreas RNA sample suggests that thi sample was degraded.

The expression of FGFR-L mRNA was also examined in RNAse protection assays (FIG. 13). A signal was detected in most of the tissues that were examined, with the strongest signal being detected in brown adipose tissue, white adipose tissue, and testis.

Figure 14:
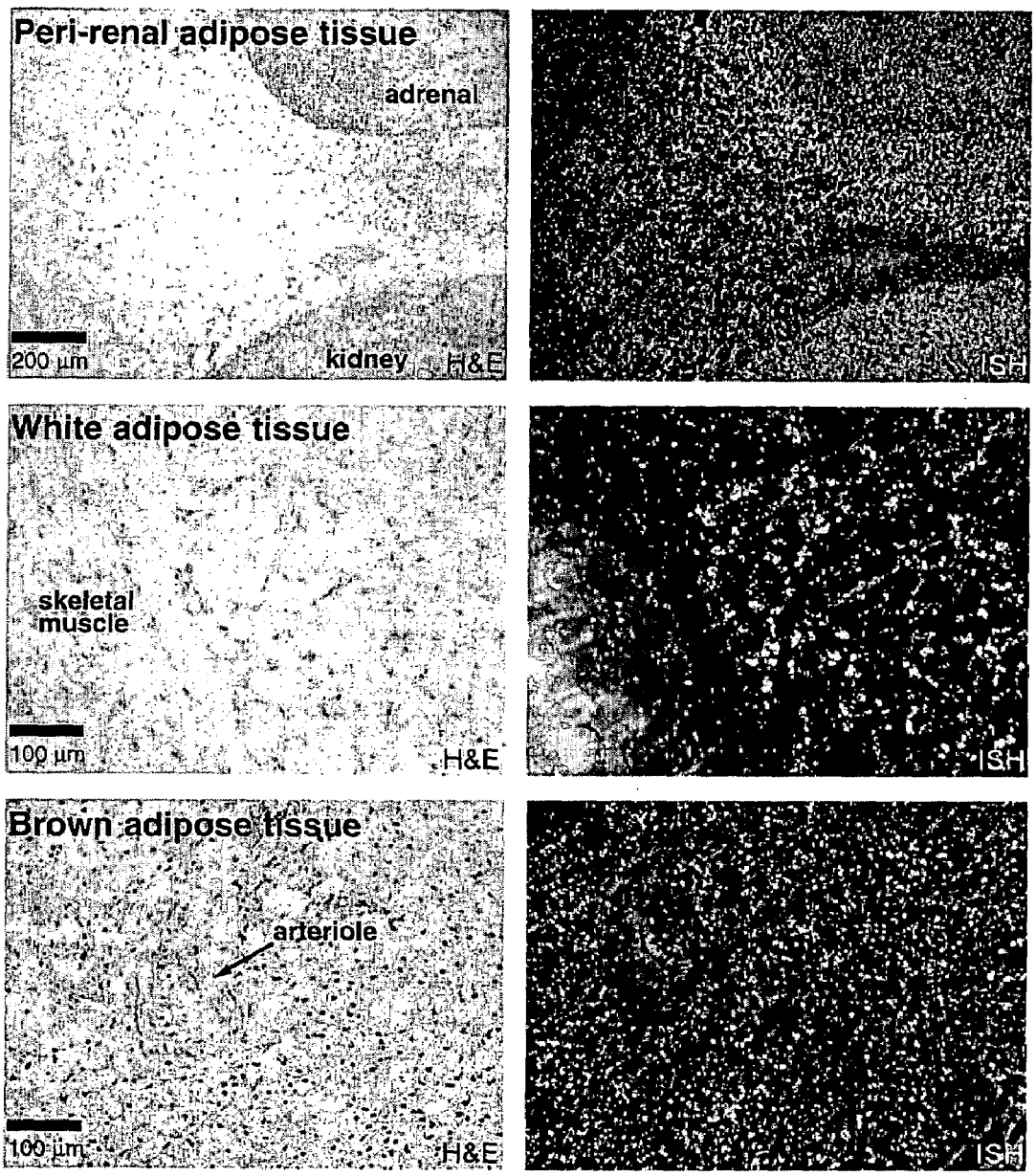
FIG. 14 illustrates the expression of FGFR-L mRNA as detected by in situ hybridization in the peri-renal, white, and brown adipose tissue of a normal adult mouse (H&E=hematoxylin and eosin counterstaining; ISH=in situ hybridization)
Figure 15:
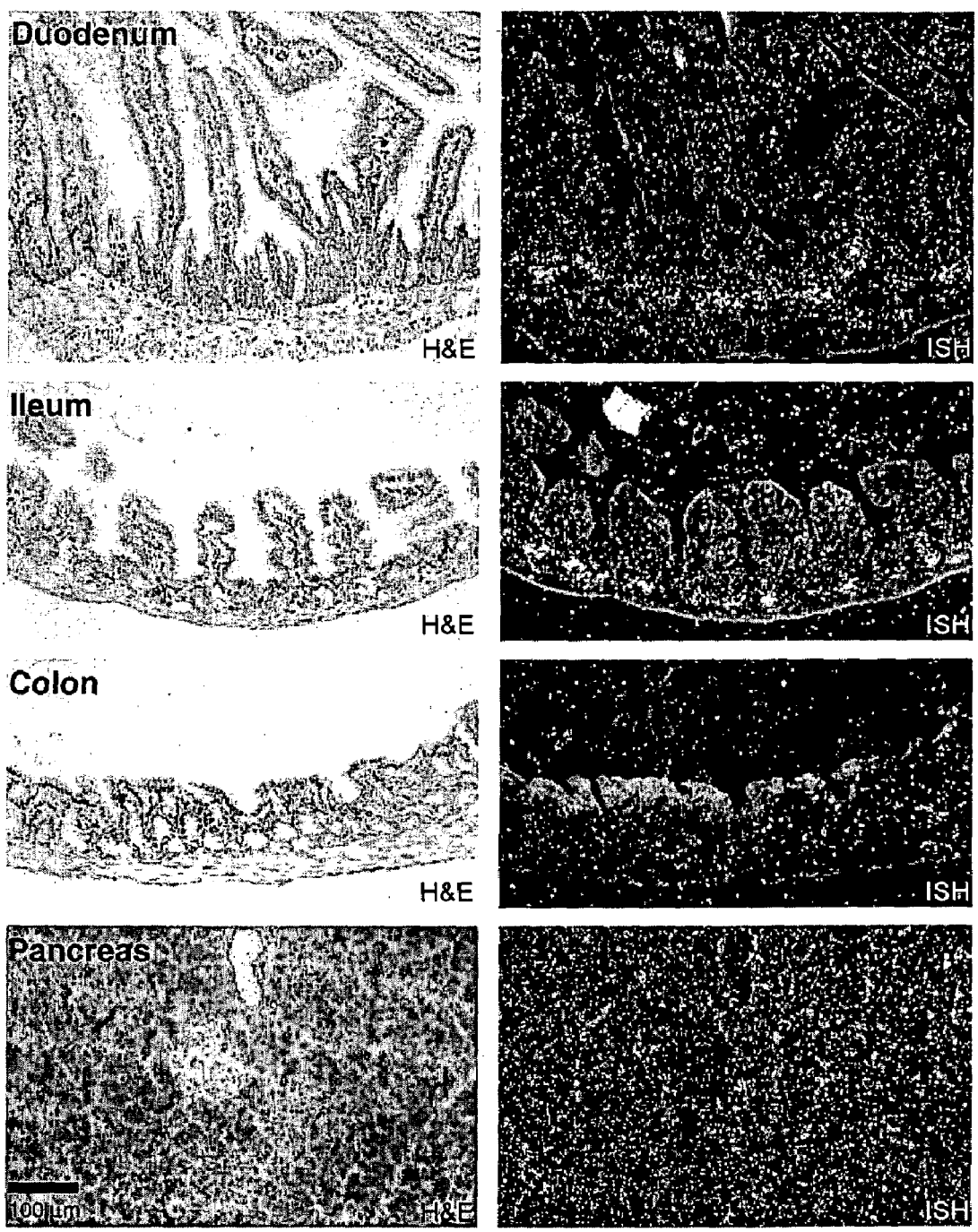
FIG. 15 illustrates the expression of FGFR-L mRNA as detected by in situ hybridization in the duodenum, ileum, colon, and pancreas of a normal adult mouse (H&E=hematoxylin and eosin counterstaining; ISH=in situ hybridization)
Figure 16:
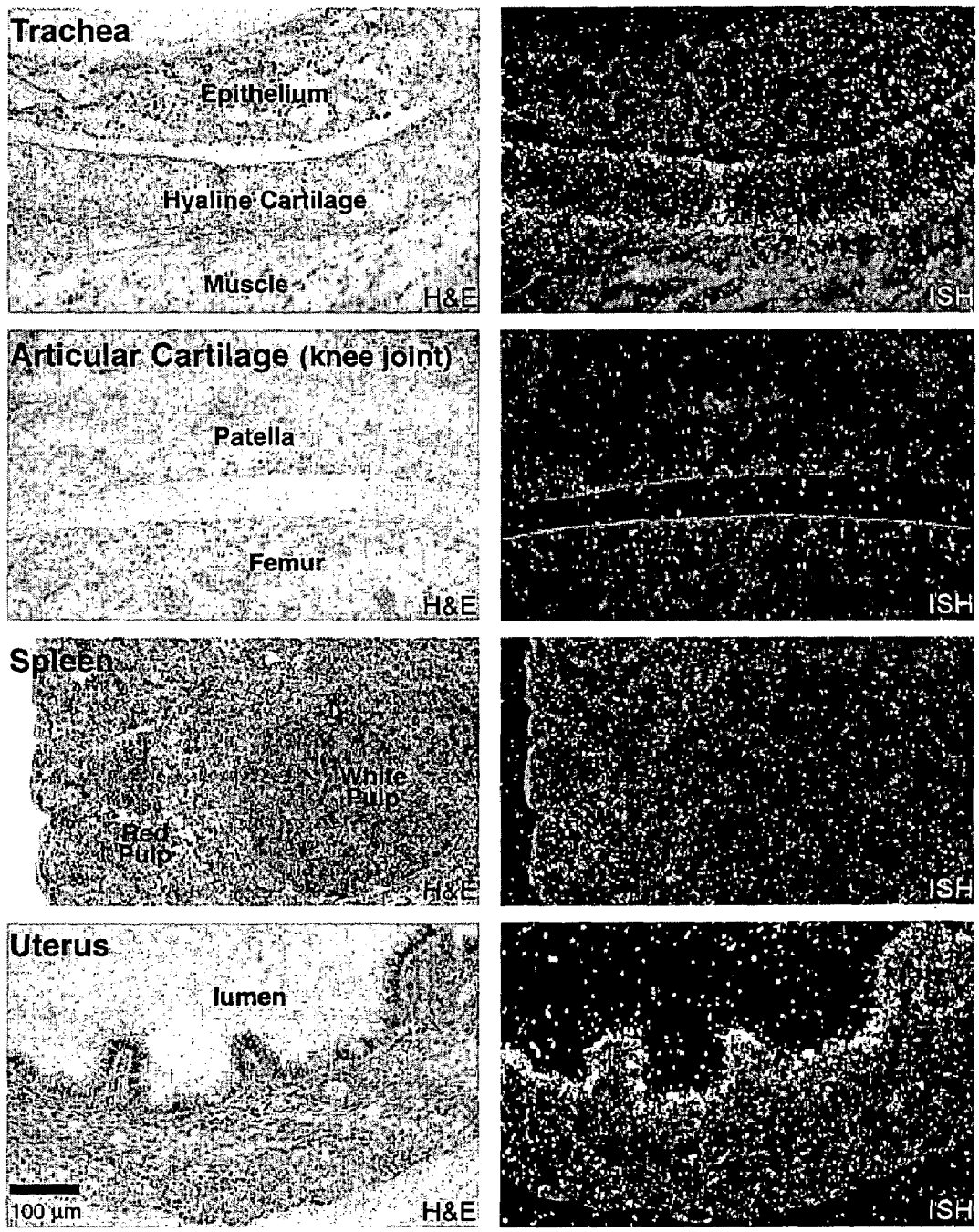
FIG. 16 illustrates the expression of FGFR-L mRNA as detected by in situ hybridization in the trachea, articular cartilage of the knee joint, spleen, and uterus of a normal adult mouse (H&E=hematoxylin and eosin counterstaining; ISH=in situ hybridization)

The expression of FGFR-L mRNA was localized by in situ hybridization, using standard techniques. The highest levels of FGFR-L mRNA were found in both white and brown adipose tissue; FGFR-L mRNA expression was detected in a peri-renal adipose depot adjacent to the adrenal gland and kidney (FIG. 14). In the digestive tissues, signal corresponding to FGFR-L mRNA was found in the small intestine (duodenum and ileum), but not in the large intestine (FIG. 15). Specifically, FGFR-L mRNA was found to be expressed at the base of the crypts, most likely the Paneth cells. FGFR-L mRNA expression was also detected in the trachea (a signal was detected over the perichondral cells adjacent to the ring of hyaline cartilage surrounding the trachea) and in the uterus (a strong signal was detected over the epithelial cells lining the uterine lumen; FIG. 16). The high expression levels of FGFR-L polypeptide detected in hyaline cartilage suggests possible clinical utility for FGFR-L polypeptide in the modulation of osteoarthritis since fibro-cartilage, characteristically present in osteoarthritic joints, resembles hyaline cartilage. Lower levels of FGFR-L mRNA expression were also detected in the articular cartilage at the knee joint and in the spleen—over the red pulp (hematopoietic) as opposed to the white pulp (lymphocytes; FIG. 16). Lower levels of expression were detected in ovary, testis, and small intestine. The high level of FGFR-L mRNA expression in adipose tissue warrents caution in the interpretation of the Northern blot data as a result of the contamination of some tissues with adipose tissue. This may be true in particular for the high level of expression observed in human pancreas.

Figure 7:
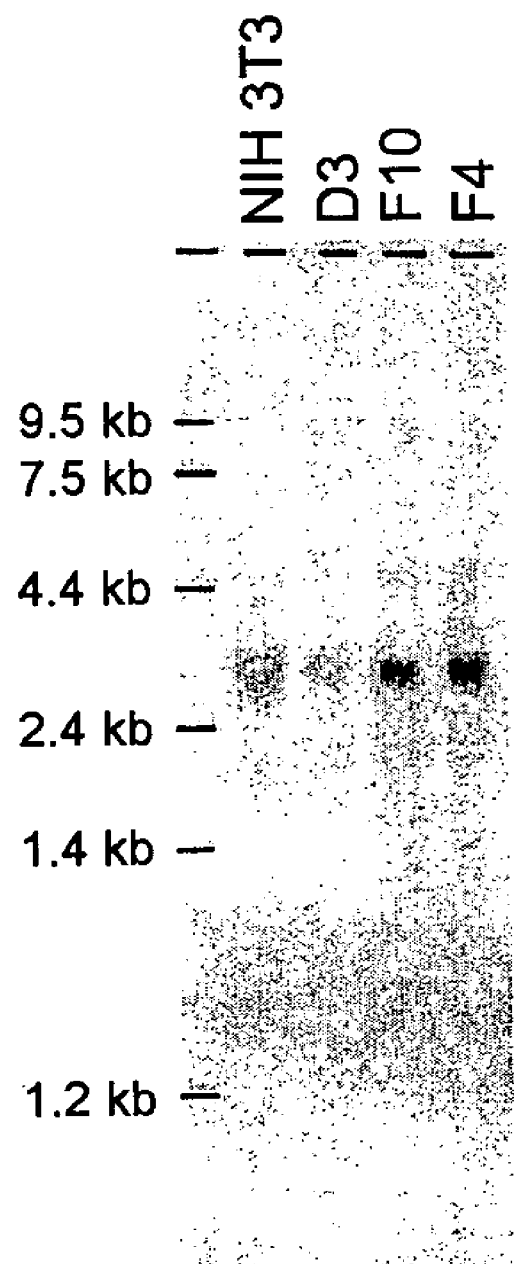
FIG. 7 illustrates the expression of FGFR-L mRNA as detected by Northern blot analysis in NIH 3T3 cells and F10, F4, and D3 mouse bone marrow-derived stromal cell lines.
Figure 17:
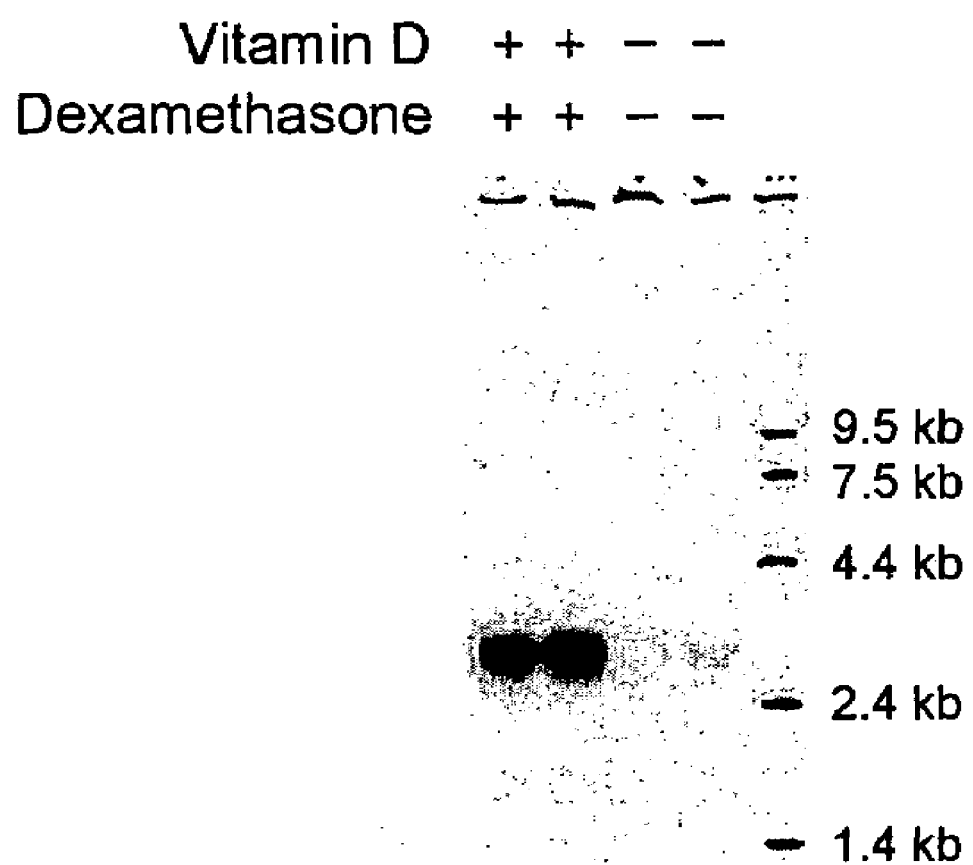
FIG. 17 illustrates the induction of FGFR-L mRNA in osteoblastic ST2 cells under conditions of osteoclastogenesis (i.e., 5-day exposure to vitamin D3 and dexamethasone)

The expression levels of murine FGFR-L mRNA detected in three bone marrow stromal cell lines (i.e., D3, F4, and F10) correlate with the ability of these cell lines to support hematopoietic stem cells. The highest expression of murine FGFR-L mRNA was detected in the stromal cell lines providing the best support (F4 and F10; FIG. 7), while much lower levels were seen in the cell line incapable of supporting hematopoietic stem cells (D3). Murine FGFR-L mRNA was also upregulated in osteoblastic ST2 cells under conditions of osteoclastogenesis (i.e., in response to vitamin D3 and dexamethasone; FIG. 17), a process which is known to be inhibited by bFGF (Jimi et al, 1996, *J. Cell. Physiol.* 168:395-402).

Figure 6:
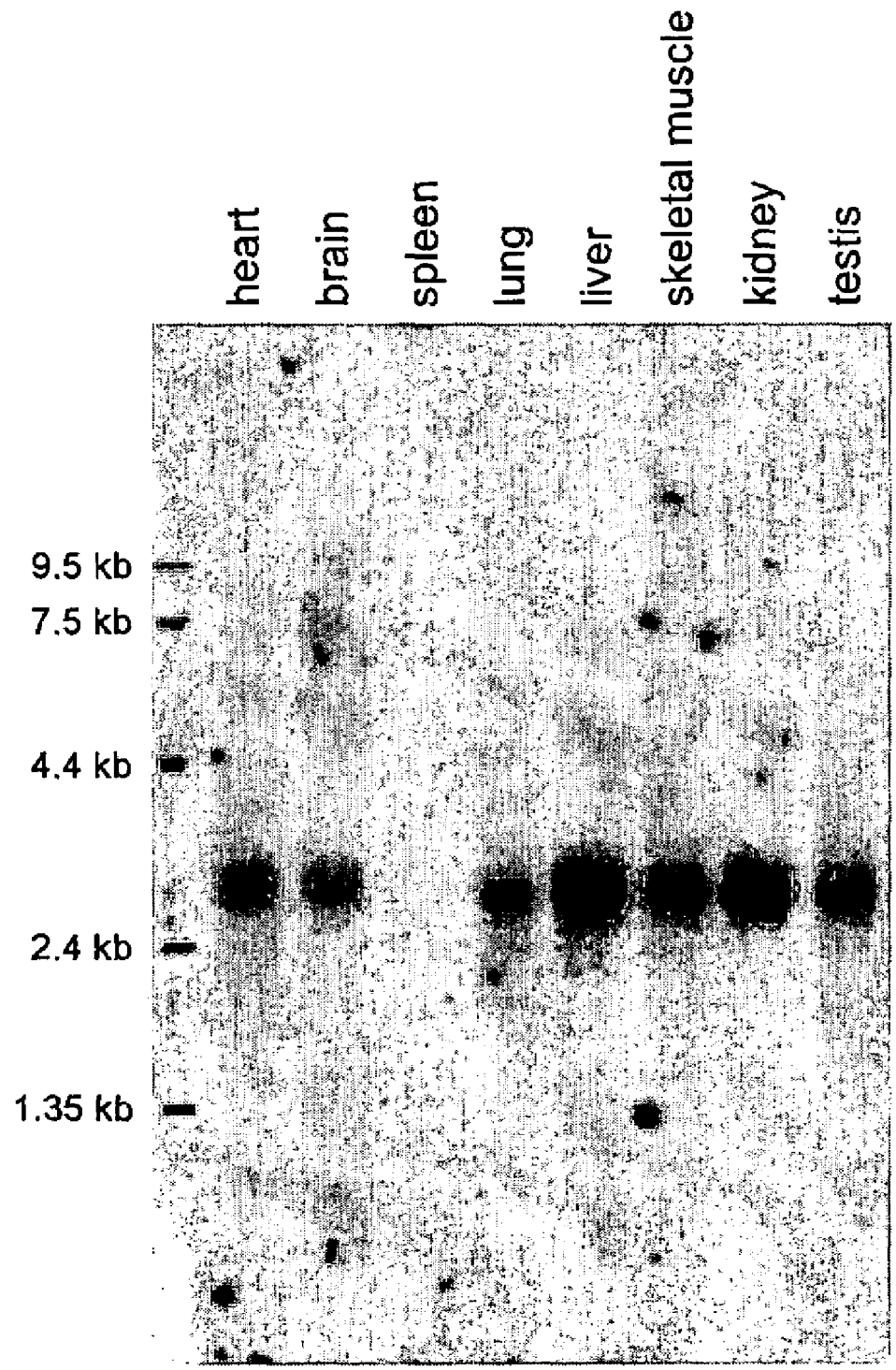
FIG. 6 illustrates the expression of FGFR-L mRNA as detected by Northern blot analysis in murine heart, brain, spleen, lung, liver, skeletal muscle, kidney, and testis.

Furthermore, expression analysis showed that the level of mRNA expression for murine FGFR-L polypeptide increased during fetal development with the lowest expression being detected at the earliest time point analyzed (i.e., day 7) and the highest expression being detected at the latest time point analyzed (i.e., day 17) (FIG. 5).

Finally, proteomic analysis showed that a peptide with a sequence identical to that of murine and human FGFR-L polypeptide was secreted from K562 cells and SV40 transformed AG2804 cells (human fibroblast). In this approach, protein mixtures were isolated from culture media that was conditioned by any one of a variety of cell lines and subjected to Mass Spectrometric analysis to identify the presence of individual peptide sequences. Proteomic analysis also showed N-linked glycosylation at residues 231 (Asp) and 293 (Asp) in the human FGFR-L polypeptide.

EXAMPLE 4

Production of Anti-FGFR-L Polypeptide Antibodies

FGFR-L polypeptide antibodies were obtained by immunizing rabbits with a polypeptide corresponding to a portion of the extracellular domain (ECD) of murine FGFR-L polypeptide (Des7-FGFR-L/ECD; SEQ ID NO: 20; comprising residues 28-368 of FGFR-L polypeptide). An FGFR-L polypeptide-Fc fusion construct was also prepared using residues 1-366 of the extracellular domain (SEQ ID NO: 21 and SEQ ID NO: 22). Suitable procedures for generating antibodies were used (see, e.g., Hudson and Bay, *Practical Immunology* (2nd ed., Blackwell Scientific Publications)).

Figure 19:
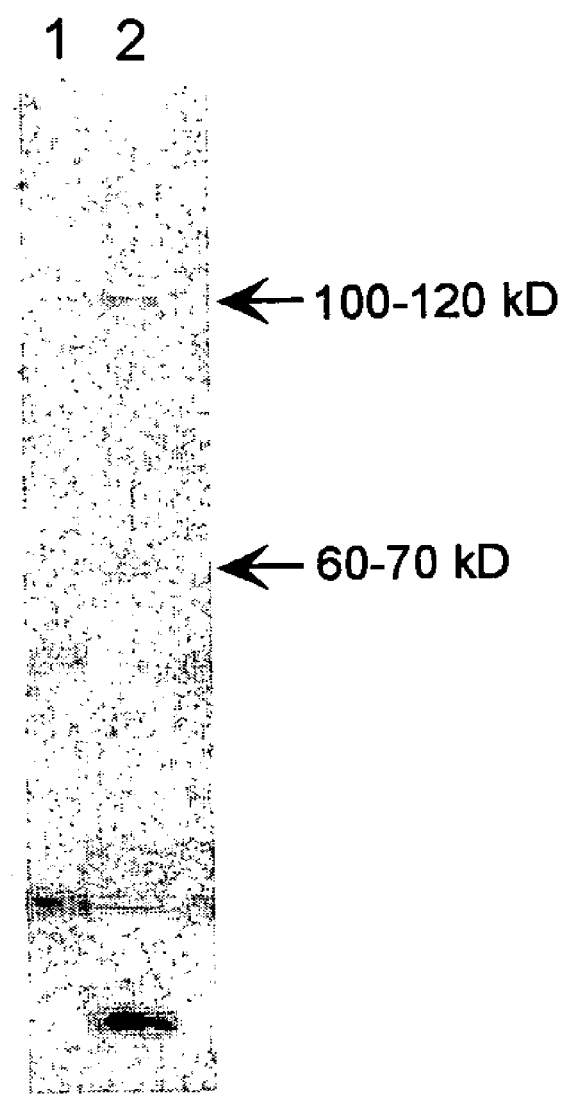
FIG. 19 illustrates the results of Western blot analysis of murine eye (lane 1) and adipose tissue (lane 2) using FGFR-L polypeptide antiserum.
Figure 20A:
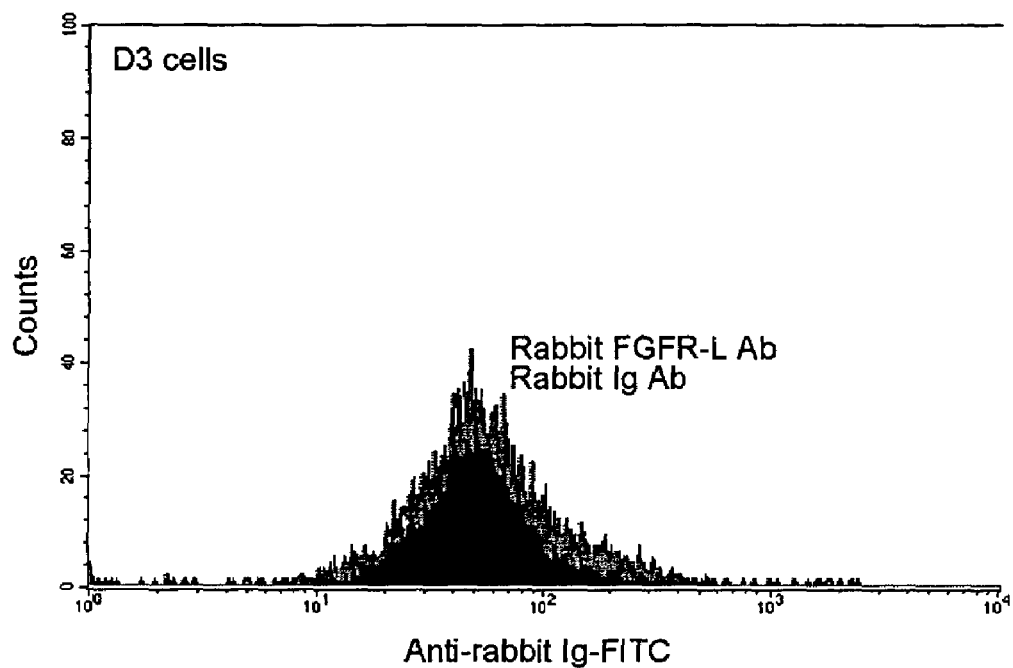
FIGS. 20A-20B illustrate the results of FACS analysis on F4 and D3 bone marrow stromal cells using FGFR-L polypeptide antiserum.
Figure 20B:
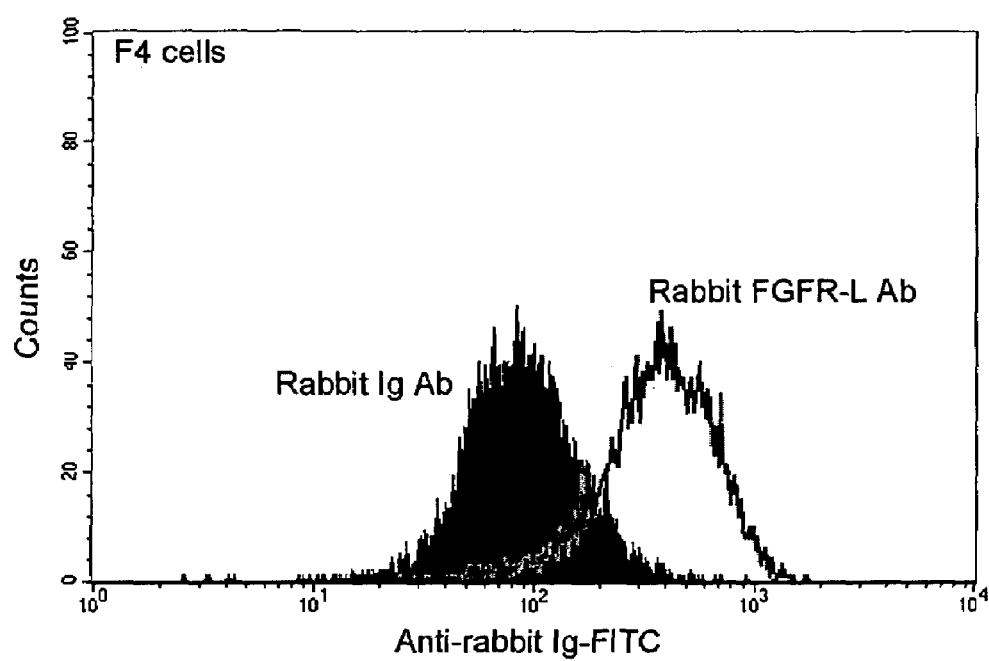
Figure 21A:
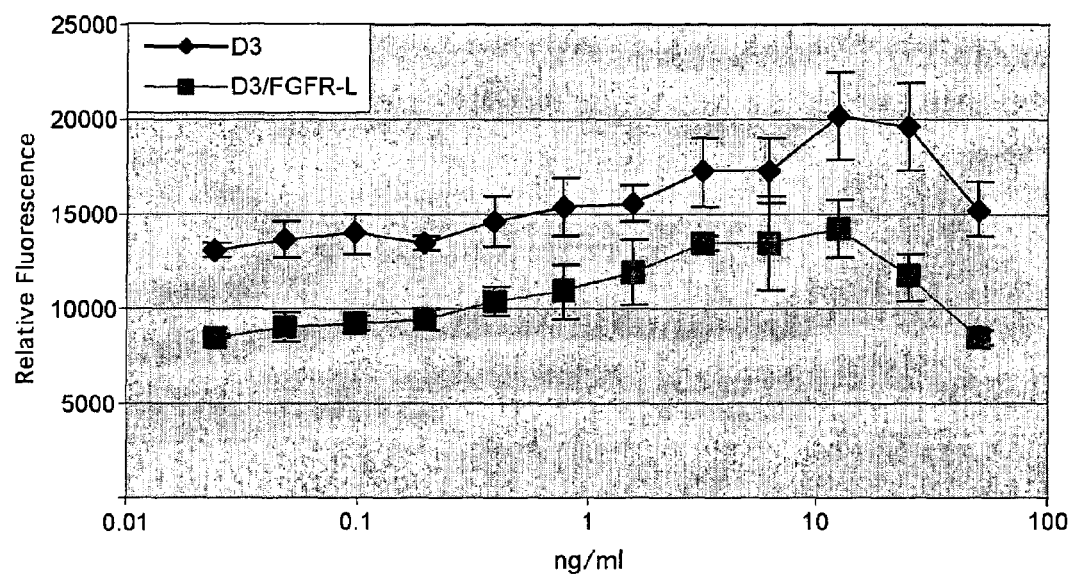
FIGS. 21A-21D illustrate the results of proliferation assays using D3 bone marrow stromal cells (either untransduced or transduced with a construct encoding FGFR-L polypeptide) following 72 hour exposure to rhuPDGF (panel A), rhuFGF-2 (panel B), rhuFGF-4 (panel C), or rhuFGF-6 (panel D)
Figure 21B:
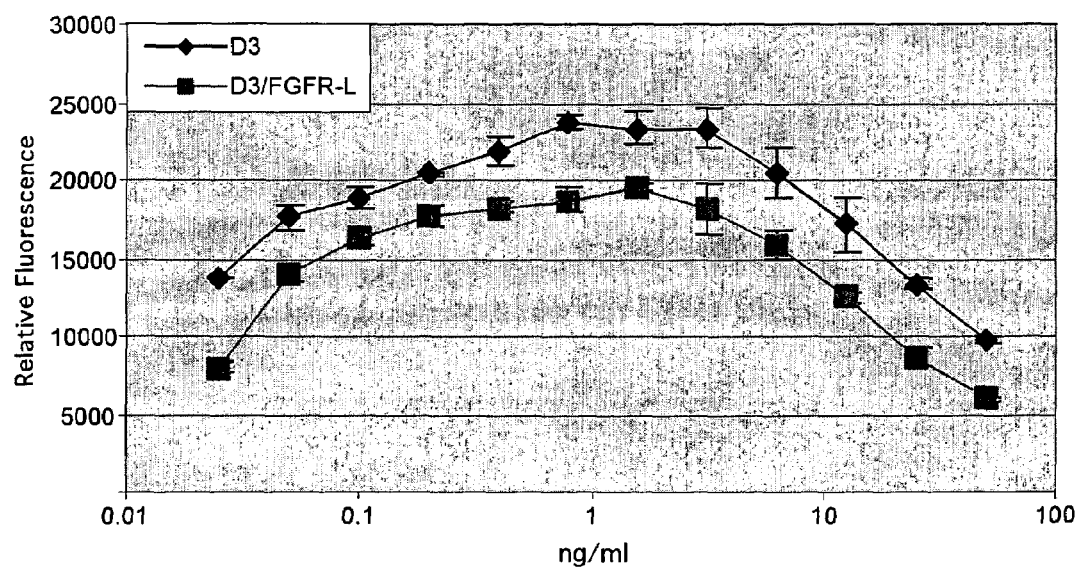
Figure 21C:
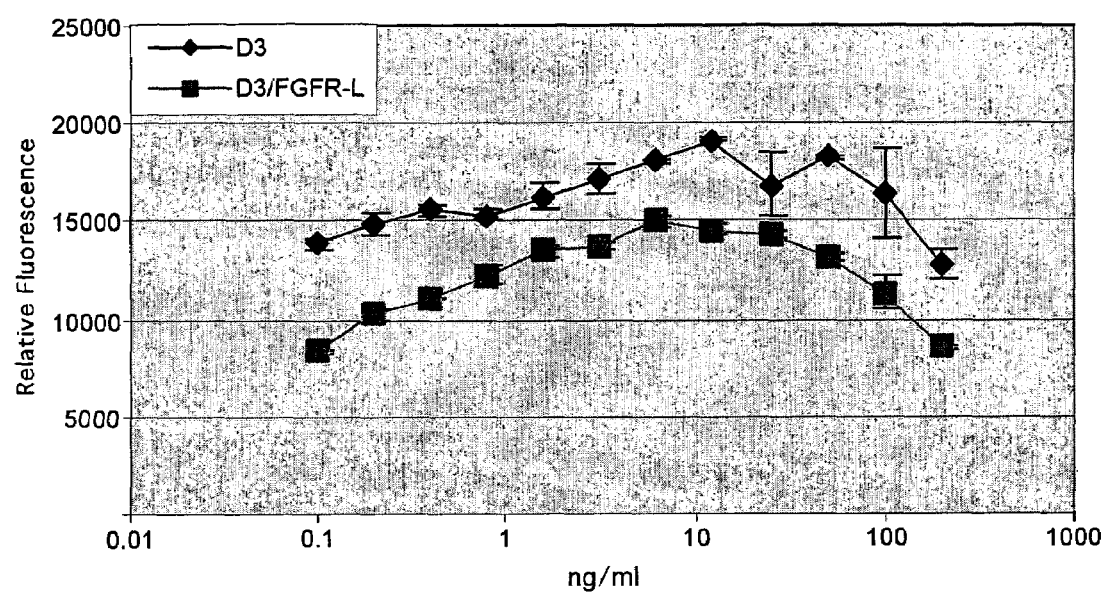
Figure 21D:
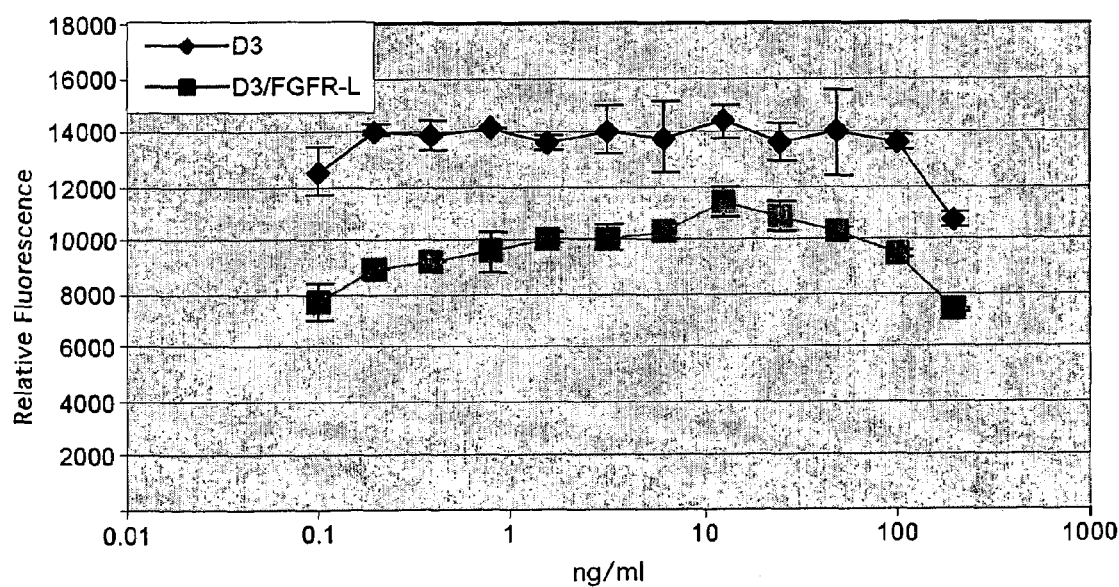

FGFR-L polypeptide antiserum was used in Western blot analysis of SDS-PAGE separated *E. coli*-derived Des7-FGFR-L/ECD and CHO-derived FGFR-L/ECD-Fc proteins. Immunoreactive bands of 95-100 kD and of 40-45 kD were detected in the CHO- and *E. coli*-derived samples, respectively (FIG. 18). A immunoreactive band of 60-70 kD was also detected in murine adipose tissue (FIG. 19), 266-6 cells (mouse acinar pancreatic tumor), AR42J cells (rat pancreas exocrine tumor), MRC5 cells (human diploid lung fibroblasts), OHS4 cells (human osteoblast), SW1353 cells (human chondrosarcoma), and K562 cells (chronic myelogenous sarcoma) following immunoprecipitation and Western blot analysis of cell lysates and conditioned media collected from these tissues and cell lines. An additional band of 100-120 kD was detected in adipose tissue, OHS4 cells and K562 cells. The crude antiserum could also be used to immunoprecipitate both proteins. Using the crude antiserum in FACS analysis, FGFR-L polypeptide cell surface staining was detected on F4 bone marrow stromal cells (shown to express high levels of FGFR-L RNA), but not on D3 bone marrow stromal cells (shown to express low levels of FGFR-L RNA; FIGS. 20A-20B).

EXAMPLE 5

In vitro Characterization of FGFR-L Polypeptides

Figure 22:
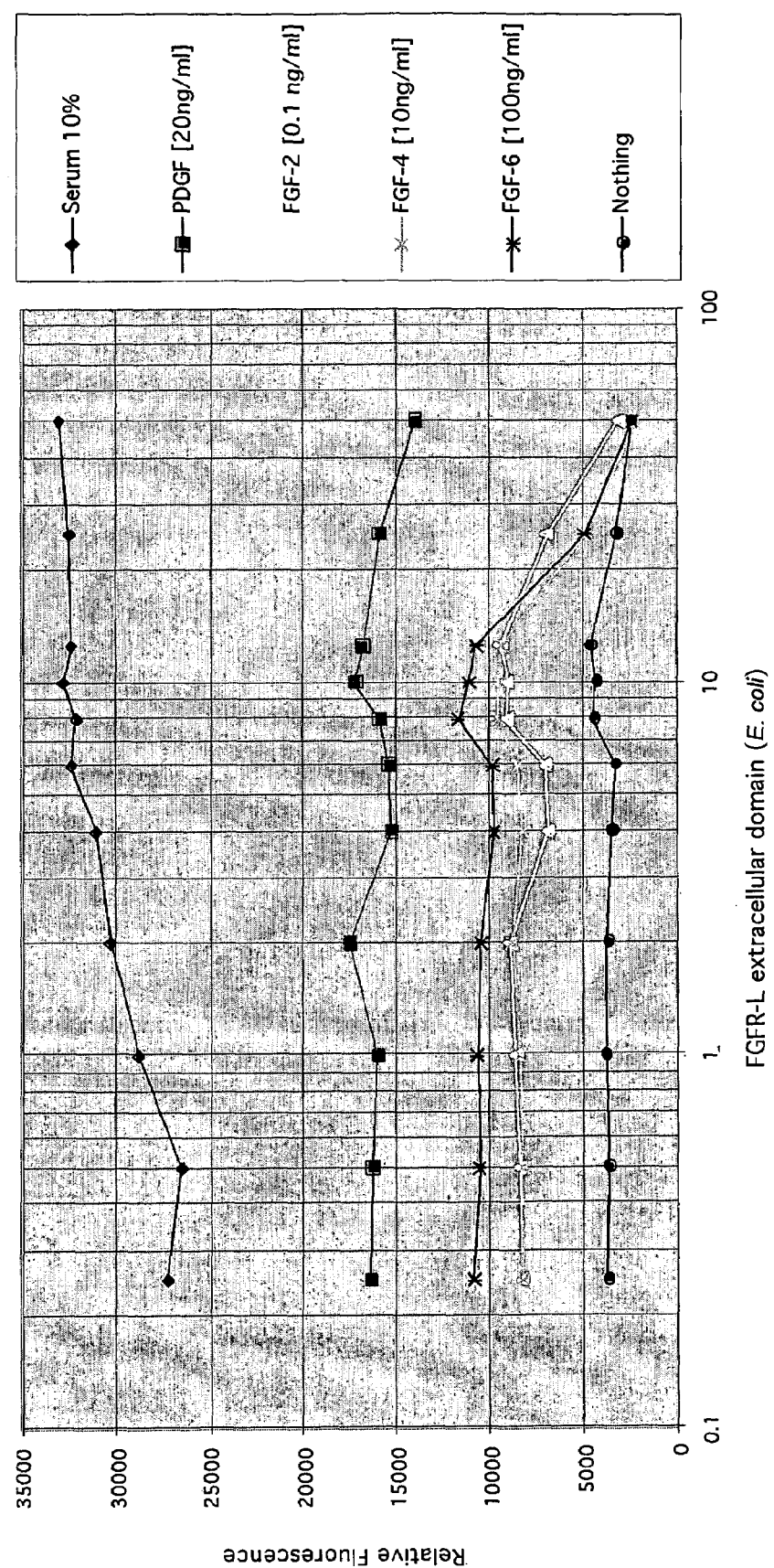
FIG. 22 illustrates the results of proliferation assays using A5-F bone marrow stromal cells following exposure to *E. coli*-derived Des7-FGFR-L/ECD protein and serum, PDGF, FGF-2, FGF-4, or FGF-6.
Figure 23:
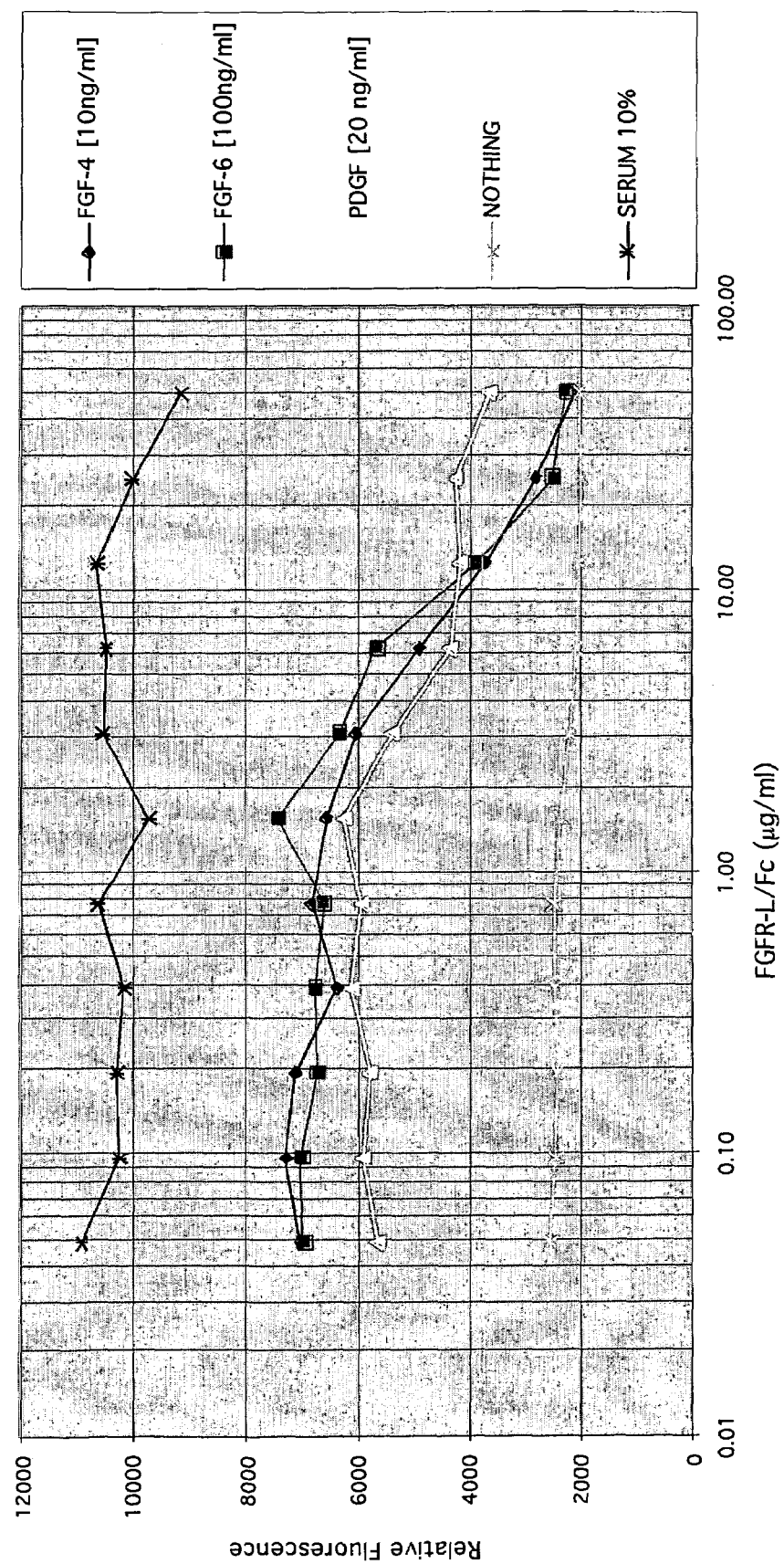
FIG. 23 illustrates the results of proliferation assays using A5-F bone marrow stromal cells following exposure to CHO-derived FGFR-L/ECD-Fc protein and serum, PDGF, FGF-4, or FGF-6.

Contructs encoding full-length FGFR-L polypeptide or the extracellular domain of FGFR-L polypeptide have proven to be poorly tolerated by transfected cells (e.g., CHO, 329 HEK, and stomal cell lines), as measured by the lower number and decreased growth rate of stable transfectants versus untransfected cells (FIGS. 21A-21D) or cells transfected with a construct encoding an FGFR-L polypeptide point mutant. When *E. coli*-derived Des7-FGFR-L/ECD was added to bone marrow stromal cell cultures, FGF-mediated, but not serum-mediated growth, was inhibited (FIG. 22). The observation that soluble FGFR-L/ECD inhibits growth induced by FGF proteins, but has less of an inhibitory effect on growth induced by PDGF or serum, suggests that FGFR-L polypeptide may interact, alone or with a co-receptor, with a natural ligand that has homology to the FGF family. Surprisingly, this effect was not observed when CHO-derived FGFR-L/ECD-Fc fusion protein was used in place of *E. coli*-derived Des7-FGFR-L/ECD (FIG. 23). Similar results were obtained for FGF and VEGF-mediated growth of human vascular endothelial cells (HU-VEC). The difference in activity between the CHO-derived and *E. coli*-derived FGFR-L polypeptides may be due to the amino acid sequence differences at their C- and/or N-terminus.

EXAMPLE 6

In vivo Characterization of FGFR-L Polypeptides

Murine bone marrow cells, transduced with a retroviral vector carrying a bicistronic message encoding full-length murine FGFR-L and the neomycin resistance gene (or the neomycin resistance gene alone) were used to transplant 10 lethally irradiated recipients as decribed previously (Yan et al., 1999, *Exp. Hematol.* 27:1409-17).

In five of the mice (randomly selected for evaluation), the overexpression of FGFR-L polypeptide over a four month period caused a 15% decrease in total body weight, a 14% decrease in serum cholesterol and 35% decrease in serum triglyceride levels. However, three weeks later the five remaining mice were weighed and bled, and the similar changes were not observed.

In vitro characterization (Example 5) of FGFR-L polypeptide indicated that the protein is poorly tolerated by a variety of cell types such that selection against FGFR-L polypeptide expression is not unexpected. As the retroviral construct described above carries both the FGFR-L gene and the neomycin resistance gene on one bicistronic message, selection against FGFR-L polypeptide expression would result in a corresponding selection against neo expression as well, either by downregulation of transcription or by removal of the transduced cells.

Figure 24:
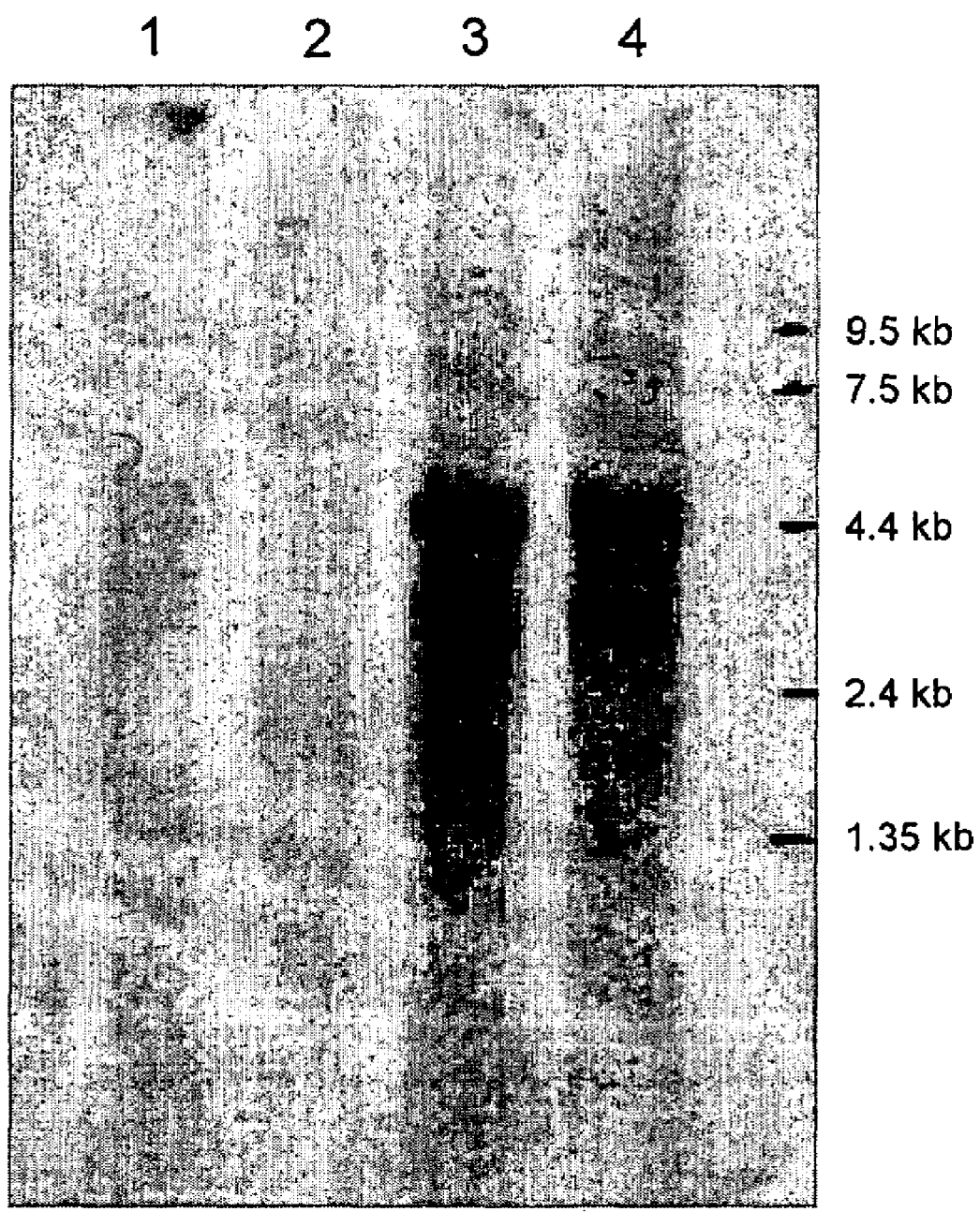
FIG. 24 illustrates the expression of the neomycin resistance gene as detected by Northern blot analysis of peripheral blood mononuclear cell (PBMN) RNA from two FGFR-L/neo-transduced mice (lanes 1 and 2) and two neo-transduced control mice (lanes 3 and 4).

Northern blot analysis of peripheral blood mononuclear cell (PBMN) RNA from two FGFR-L/neo-transduced mice exhibiting the phenotype and two neo-transduced control mice indicated that the control mice show abundant expression of neo transcripts of the expected size and the FGFR-L/neo-transduced mice do not (FIG. 24). This suggests that FGFR-L polypeptide expression is actively selected against and precedes the ultimate disappearance of a transient phenotype.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated nucleic acid molecule comprising a nucleotide sequence:
   (a) as set forth in SEQ ID NO: 1;
   (b) of the DNA insert in ATCC Deposit No. PTA-1062;
   (c) encoding the polypeptide as set forth in SEQ ID NO: 2; or
   (d) that hybridizes to the complement of the nucleotide sequence of (c) at 65° C. in a hybridization and wash buffer comprising 0.015 M sodium chloride and 0.0015

M sodium citrate or at 42° C. in a hybridization and wash buffer comprising 0.015 M sodium chloride, 0.0015 M sodium citrate, and 50% formamide, and encoding a polypeptide that inhibits FGF-mediated growth in bone marrow stromal cells; or (e) that is complementary to the nucleotide sequence of any of (a)-(d).

2. An isolated nucleic acid molecule comprising:
(a) a region of the nucleotide sequence of SEQ ID NO: 1 or the DNA insert in ATCC Deposit No. PTA 1062 encoding a polypeptide fragment of at least 25 amino acid residues of SEQ ID NO: 2;
(b) a region of the nucleotide sequence of SEQ ID NO: 1 or the DNA insert in ATCC Deposit No. PTA-1062 comprising a fragment of at least 75 nucleotides, wherein the fragment encodes a portion of the polypeptide as set forth in SEQ ID NO: 2;
(c) a nucleotide sequence that hybridizes to the complement of the nucleotide sequence of either (a) or (b) at 65° C. in a hybridization and wash buffer comprising 0.015 M sodium chloride and 0.0015 M sodium citrate or at 42° C. in a hybridization and wash buffer comprising 0.015 M sodium chloride, 0.0015 M sodium citrate, and 50% formamide, and encoding a polypeptide that inhibits FGF-mediated growth in bone marrow stromal cells; or
(d) a nucleotide sequence that is complementary to the nucleotide sequence of any of (a)-(c).

3. An isolated nucleic acid molecule comprising a nucleotide sequence:
(a) encoding a polypeptide as set forth in SEQ ID NO: 2 which has a C- and/or N-terminal truncation, wherein the polypeptide having a C- and/or N-terminal truncation inhibits FGF-mediated growth in bone marrow stromal cells;
(b) that hybridizes to the complement of the nucleotide sequence of (a) at 65° C. in a hybridization and wash buffer comprising 0.015 M sodium chloride and 0.0015 M sodium citrate or at 42° C. in a hybridization and wash buffer comprising 0:015 M sodium chloride, 0.0015 M sodium citrate, and 50% formamide, and encoding a polypeptide that inhibits FGF-mediated growth in bone marrow stromal cells; or
(c) that is complementary to the nucleotide sequence of either (a) or (b).

4. A vector comprising the nucleic acid molecule of any of claims 1, 2, or 3.

5. An isolated host cell comprising the vector of claim 4.

6. The isolated host cell of claim 5 that is a eukaryotic cell.

7. The isolated host cell of claim 5 that is a prokaryotic cell.

8. A process of producing a polypeptide encoded by the nucleic acid molecule of any of claims 1(a), 1(b), 1(c), or 1(d), comprising culturing a host cell comprising the nucleic acidmolecule of any of claims 1(a), 1(b), 1(c), or 1(d) under suitable conditions to express the polypeptide, and optionally isolating the polypeptide from the culture.

9. A process of producing a polypeptide encoded by the nucleic acid molecule of any of claims 2(a), 2(b), or 2(c), comprising culturing a host cell comprising the nucleic acid molecule of any of claims 2(a), 2(b), or 2(c) under suitable conditions to express the polypeptide, and optionally isolating the polypeptide from the culture.

10. A process of producing a polypeptide encoded by the nucleic acid molecule of either claim 3(a) or 3(b), comprising culturing a host cell comprising the nucleic acid molecule of either claim 3(a) or 3(b) under suitable conditions to express the polypeptide, and optionally isolating the polypeptide from the culture.

11. The process of any of claims 8, 9, or 10, wherein the nucleic acid molecule comprises promoter DNA other than the promoter DNA for the native Fibroblast Growth Factor Receptor-Like gene operatively linked to the nucleic acid molecule.

* * * * *